US010080750B2

(12) United States Patent
Lan et al.

(10) Patent No.: US 10,080,750 B2
(45) Date of Patent: Sep. 25, 2018

(54) AMINOPYRIMIDINE DERIVATIVES FOR USE AS MODULATORS OF KINASE ACTIVITY

(71) Applicant: Merck Patent GmbH, Darmstadt (DE)

(72) Inventors: Ruoxi Lan, Waltham, MA (US); Bayard R. Huck, Sudbury, MA (US); Xiaoling Chen, Chestnut Hill, MA (US); Lizbeth C. Deselm, Melrose, MA (US); Hui Qiu, Acton, MA (US); Yufang Xiao, Lexington, MA (US); Constantin Neagu, Belmont, MA (US); Igor Mochalkin, Westford, MA (US); Theresa L. Johnson, Salem, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/490,370

(22) Filed: Apr. 18, 2017

(65) Prior Publication Data

US 2017/0217905 A1   Aug. 3, 2017

Related U.S. Application Data

(60) Continuation of application No. 15/060,050, filed on Mar. 3, 2016, now Pat. No. 9,662,330, which is a division of application No. 14/236,405, filed as application No. PCT/US2012/054877 on Sep. 12, 2012, now Pat. No. 9,321,760.

(60) Provisional application No. 61/533,606, filed on Sep. 12, 2011.

(51) Int. Cl.
| *A61K 31/506* | (2006.01) |
| *C07D 403/12* | (2006.01) |
| *C07D 401/14* | (2006.01) |
| *C07D 405/14* | (2006.01) |
| *C07D 413/14* | (2006.01) |
| *C07D 401/04* | (2006.01) |
| *C07D 401/12* | (2006.01) |
| *C07D 403/04* | (2006.01) |
| *C07D 403/06* | (2006.01) |
| *C07D 239/48* | (2006.01) |
| *C07D 413/04* | (2006.01) |
| *C07D 417/14* | (2006.01) |
| *C07D 405/12* | (2006.01) |
| *C07D 417/12* | (2006.01) |
| *C07D 239/49* | (2006.01) |
| *C07D 413/06* | (2006.01) |

(52) U.S. Cl.
CPC .......... *A61K 31/506* (2013.01); *C07D 239/48* (2013.01); *C07D 239/49* (2013.01); *C07D 401/04* (2013.01); *C07D 401/12* (2013.01); *C07D 401/14* (2013.01); *C07D 403/04* (2013.01); *C07D 403/06* (2013.01); *C07D 403/12* (2013.01); *C07D 405/12* (2013.01); *C07D 405/14* (2013.01); *C07D 413/04* (2013.01); *C07D 413/06* (2013.01); *C07D 413/14* (2013.01); *C07D 417/12* (2013.01); *C07D 417/14* (2013.01)

(58) Field of Classification Search
CPC .. C07D 403/12; C07D 401/12; C07D 417/14; C07D 401/14; C07D 405/14; C07D 413/14; C07D 401/04; C07D 417/12; C07D 403/06; C07D 239/48; C07D 413/04; C07D 405/12; C07D 403/04; A61K 31/506
See application file for complete search history.

(56) References Cited

U.S. PATENT DOCUMENTS

| 7,115,597 | B2 | 10/2006 | Bilodeau et al. |
| 8,349,836 | B2 | 1/2013 | Araldi et al. |
| 2005/0130954 | A1 | 6/2005 | Mitchell et al. |
| 2008/0146569 | A1* | 6/2008 | Blake ............... C07D 213/82 514/235.5 |
| 2014/0343029 | A1 | 11/2014 | Lan et al. |
| 2015/0225371 | A1 | 8/2015 | Lan et al. |
| 2015/0239902 | A1 | 8/2015 | Lan et al. |

FOREIGN PATENT DOCUMENTS

| WO | 03064397 A1 | 8/2003 |
| WO | 04092154 A1 | 10/2004 |
| WO | 05033086 A1 | 4/2005 |
| WO | 05039506 A2 | 5/2005 |
| WO | 05051304 A2 | 6/2005 |
| WO | 05054237 A1 | 6/2005 |
| WO | 05056014 A1 | 6/2005 |
| WO | 05117909 A2 | 12/2005 |
| WO | 06071819 A1 | 7/2006 |
| WO | 06078992 A2 | 7/2006 |
| WO | 06120573 A2 | 11/2006 |
| WO | 06131835 A2 | 12/2006 |
| WO | 06136821 A1 | 12/2006 |
| WO | 08075172 A2 | 6/2008 |
| WO | 08140947 A1 | 11/2008 |

(Continued)

OTHER PUBLICATIONS

Goodman & Gilman's: The Pharmacological Basis of Therapeutics 853-908 (L.L. Brunton et al., eds., 11th ed., 2008).*

(Continued)

*Primary Examiner* — Alexander R Pagano
(74) *Attorney, Agent, or Firm* — Dwight D. Kim; EMD Serono Research and Development Institute

(57) ABSTRACT

The invention provides novel heterocyclic amine compounds according to Formula (I) and their manufacture and use for the treatment of hyperproliferative diseases, such as cancer.

10 Claims, No Drawings
Specification includes a Sequence Listing.

(56) References Cited

FOREIGN PATENT DOCUMENTS

| WO | 10056563 A1 | 5/2010 |
| WO | 10093419 A1 | 8/2010 |
| WO | 11029043 A1 | 3/2011 |
| WO | 12013282 A1 | 2/2012 |
| WO | 12016001 A1 | 2/2012 |
| WO | 12069146 A1 | 5/2012 |

OTHER PUBLICATIONS

C. Barillari et al., 24 European Journal of Organic Chemistry,4737-4741 (2001).*
S. Zikolova et al., 31 Nauchnoissled. Khim.-Farm. Inst., Sofia, Bulg. Farmatsiya (Sofia, Bulgaria), 1-7 (1981).*
CAS Abstract and Indexed Compounds: S, Zikolova et al., Synthesis of piperazinylpyrimidines, Nauchnoissled. Khim.-Farm. Inst., Sofia, Bulg. Farmatsiya (Sofia, Bulgaria), 1-7 (1981).*
CAS Compound Registry No. 1269373-66-1 (Mar. 21, 2011).*
Barillari C et al., Solid Phase Synthesis of Diamino-Substituted Pyrimidines, Eur. J. Org. Chem, 2001, 4737-4741.
Barlund et al., Multiple Genes at 17q23 Undergo Amplification and Overexpression in Breast Cancer, Cancer Res., 2000, 60:5340-5346.
Couch et al., Localization of PS6K to Chromosomal Region 17q23 and Determination of Its Amplification in Breast Cancer, Cancer Res., 1999, 59:1408-11.
Garcia-Bustos J. et al., PIK1, an essential phosphatidylinositol 4-kinase associated with the yeast nucleus, EMBO J., 1994, 13(10):2352-2361.
Hanks, S.K. and Hunter T., The eukaryotic protein kinase superfamily: Kinase (catalytic) domain structure and classification, FASEB J., 1995, 9:576-596.
Hardie and Hanks, The Protein Kinase Facts Book. I and II, 1995, Academic Press, San Diego, CA.
Hiles I. et al., Phosphatidylinositol 3-Kinase: Structure and Expression of the 110 kd Catalytic Subunit, Cell, 1992, 70:419-429.
Knighton D. et al., Crystal Structure of the Catalytic Subunit of Cyclic Adenosine Monophosphate-Dependent Protein Kinase, Science, 1991, 253:407-414.
Kunz J. et al., Target of Rapamycin in Yeast, TOR2, Is an Essential Phosphatidylinositol Kinase Homolog Required for G1 Progression, Cell, 1993, 73:585-596.
Wu et al., 17q23 Amplifications in Breast Cancer Involve the PAT1, RAD51C, PS6K, and SIGMA1B Genes, Cancer Res. (2000): 60:5371-5375.
Preliminary Report on Patentability, dated Mar. 12, 2014, pp. 1-8.
S. Zikolova et al., 31 Farmatsiya, 1981, 1-7.
J. Luo et al., 36 Cell, 823-837 (2009).
T. Soussi 60 Cancer Research, 1777-1788 (2000).
P. Lissoni et al, 7 Cancer Research, 397-401 (2009).
National Cancer Institute (http://www.cancer.gov/) (Downloaded May 29, 2014).
F. Bunz, Principles of Cancer Genetics 1-47, 1 (2008).
P.K. Kuppen et al., 115 Histochemistry and Cell Biology, 67-72 (2001).
D. Scheinberg et al., Management of Acute Leukemias, in 2 Cancer Principles & Practice of Oncology 2088, 2092 (V.T. DeVita, Jr. et al. eds., 7th ed., 2005).
D. Druker et al., Chronic Myelogenous Leukema, in 2 Cancer Principles & Practice of Oncology 2121 (V. T. DeVita, Jr. et al. eds., 7th ed., 2005).
S. O'Brien et al., Chronic Lymphoid Leukemias, in 2 Cancer Principles & Practice of Oncology 2133 (V.T. DeVita, Jr. et al. eds., 7th ed., 2005).
H.A. Fine, Neoplasms of the Central Nervous System in, 2 Cancer Principles & Practice of Oncology 1834-1887 (V.T. DeVita, Jr. et al. eds., 5th ed., 2005).
Fabbro et al., Kinase Inhibitors, Methods in Molecular Biology (B. Kuster ed.), 2012, 795: 1-34.
T.A. Denison et al., Heterogeneity of Cancers and Its Implication for Targeted Drug Delivery in, Cancer Targeted Drug Delivery an Elusive Dream, 337-362 (Y.H. Bae et al., eds., 2013).
U. Bandarage et al., 19 Bioorganic & Medicinal Chemistry Letters, 5191-5194 (2009).
G.L. Araldi et al., 71 Cancer Research, 3540 (2011).
CAS Abstract and Indexed Compounds for CAS Accession No. 1982: 199633 (1982) (S. Zikolova et al., 31 Farmatsiya (Sofia, Bulgaria), 1-7 (1981)).

* cited by examiner

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: substrate

<400> SEQUENCE: 1

Ala Lys Arg Arg Arg Leu Ser Ser Leu Arg Ala
1               5                   10
```

AMINOPYRIMIDINE DERIVATIVES FOR USE AS MODULATORS OF KINASE ACTIVITY

RELATED APPLICATIONS

This application is a CONTINUATION application of U.S. Ser. No. 15/060,050, filed on Mar. 3, 2016, which is a DIVISIONAL application of U.S. Ser. No. 14/236,405, which is a U.S. national stage application of PCT international application PCT/US2012/054877, filed on Sep. 12, 2012, which claims the benefit of U.S. provisional application U.S. Ser. No. 61/533,606, filed on Sep. 12, 2011. The entire contents of the aforementioned applications are hereby incorporated by reference.

FIELD OF THE INVENTION

The invention relates to a series of heterocyclic amine compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

SUMMARY OF THE RELATED ART

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)). Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Protein kinase 70S6K, the 70 kDa ribosomal protein kinase p70S6K (also known as SK6, p70/p85 S6 kinase, p70/p85 ribosomal S6 kinase and pp70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKCζ. Akt directly phosphorylates and inactivates TSC2, thereby activating mTOR. In addition, studies with mutant alleles of p70S6K that inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on it participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M. Barlund, O. Monni, J. Kononen, R. Cornelison, J. Torhorst, G. Sauter, O.-P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375).

The p70S6K gene has been identified as a target of amplification and overexpression in this region, and statistically significant association between amplification and poor prognosis has been observed. Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported. In response to energy stress, the tumor suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations. P70S6K has been implicated in metabolic diseases and disorders. It was reported that the absence of p70S6K protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

Compounds described as suitable for p70S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/131835, WO 08/140947, WO 10/093419, WO 10/056563, WO 12/013282, WO 12/016001 and WO 12/069146.

DESCRIPTION OF THE INVENTION

It is the object of the present invention to provide novel compounds that modulate kinase activity. This protein kinase modulation includes, but is not limited to, p70S6K inhibition and Akt inhibition useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

As a result, this invention provides novel, heterocyclic pyrimidinyl and pyridinyl amine compounds and pharmaceutically acceptable salts, solvates or prodrugs thereof, that are kinase inhibitors and useful in the treatment of the above mentioned diseases. The compounds are defined by Formula (I):

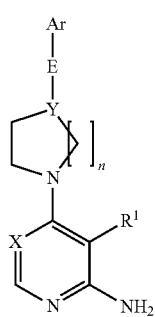

and pharmaceutically acceptable salts, solvates, solvates of salts, or prodrugs thereof, wherein:

X is N or CH;
Y is N or $CR^2$;
E is an unbranched or branched alkyl linker having 1, 2, 3, 4, 5, 6 or 7 C atoms, which may be unsubstituted or mono- or disubstituted with Hal, OH, CN or $NH_2$, in which one $CH_3$ group may be replaced by $Cyc^1$, $Cyc^2$, $CONH_2$, $CF_3$, and in which one, two or three $CH_2$ groups may be replaced by —O—, —NH—, or —CO—, and in which one CH group may be replaced by —N—;
$R^1$ is H, CN, $CONH_2$, Hal, LA, O(LA), Ar, $Cyc^1$ or $Cyc^2$;
$R^2$ is H, $NH_2$, Hal or CN;
Hal is F, Cl, Br or I;
LA is an unbranched or branched, linear saturated or partially unsaturated hydrocarbon chain having 1, 2, 3 4, 5 or 6 C atoms, wherein 1, 2 or 3 H atoms may be replaced by Hal or OH;
Ar is a mono- or bicyclic aromatic homo- or heterocycle having 0, 1, 2, 3 or 4 N, O and/or S atoms and 5, 6, 7, 8, 9, or 10 skeleton atoms, which may be unsubstituted or, independently of one another, mono- or disubstituted by Hal, LA, OH, SH, O(LA), $NH_2$, NH(LA), $N(LA)_2$, $NO_2$, CN, OCN, COOH, COO(LA), $CONH_2$, CONH(LA), $CON(LA)_2$, NHCO(LA), NHCONH(LA), $NHCONH_2$, CHO and CO(LA), and/or monosubstituted by $Cyc^2$ or O-$Cyc^2$;
$Cyc^1$ is a 3, 4, 5 or 6 membered monocyclic aliphatic homo- or heterocycle having 0-2 heteroatoms, selected from O, S and N, which may be mono- or disubstituted by Hal, LA, $NH_2$, NH(LA), $N(LA)_2$, HO(LA)-;
$Cyc^2$ is a 5 or 6 membered monocyclic aromatic homo- or heterocycle having 0-3 heteroatoms, selected from O, S and N, which may be mono- or di-substituted by Hal or LA; and
n is 1 or 2.

In a further preferred embodiment the compounds of the invention conform to Subformulae 1 to 13 of Formula (I), wherein
in Subformula 1
X is N,
in Subformula 2
Y is N or CH,
in Subformula 3
$R^1$ is Hal, LA, O(LA), $Cyc^1$ or $Cyc^2$,
in Subformula 4
Ar is phenyl or pyridyl, which is unsubstituted or mono- or disubstituted by Hal, LA or O(LA),
in Subformula 5
E is a methyl linker which is substituted by aminomethyl, wherein the amino group of the aminomethyl is unsubstituted, or mono- or disubstituted by LA, or E is a methyl linker which is substituted by (azetidin-1-yl)methyl,
in Subformula 6
Y is $CNH_2$,
E is —CH($R^3$)—NH—CO— or —CO—NH—CH($R^3$)—,
$R^3$ is H, $CH_2CONH_2$ or LA,
in Subformula 7
X is N,
Y is N or CH,
$R^1$ is Hal, LA, O(LA), $Cyc^1$ or $Cyc^2$,
in Subformula 8
X is N,
Y is N or CH,
Ar is phenyl or pyridyl, which is unsubstituted or mono- or disubstituted by Hal, LA or O(LA),
in Subformula 9
X is N,
Y is N or CH,
E is a methyl linker which is substituted by aminomethyl, wherein the amino group of the aminomethyl is unsubstituted, or mono- or disubstituted by LA, or E is a methyl linker which is substituted by (azetidin-1-yl)methyl, in Subformula 10
X is N,
Y is CNH$_2$,
E is —CH(R$^3$)—NH—CO— or —CO—NH—CH(R$^3$)—,
R$^1$ is Hal, CONH$_2$, LA, O(LA), Cyc$^1$ or Cyc$^2$,
R$^3$ is H, CH$_2$CONH$_2$ or LA,
in Subformula 11
X is N,
Y is CNH$_2$,
E is —CH(R$^3$)—NH—CO— or —CO—NH—CH(R$^3$)—,
R$^1$ is Hal, CONH$_2$, LA, O(LA), Cyc$^1$ or Cyc$^2$,
R$^3$ is H, CH$_2$CONH$_2$ or LA,
Ar is phenyl or pyridyl, which is unsubstituted or mono- or disubstituted by Hal, LA or O(LA),
in Subformula 12
X is N,
Y is CNH$_2$,
E is —CH(R$^3$)—NH—CO— or —CO—NH—CH(R$^3$)—,
R$^3$ is H, CH$_2$CONH$_2$ or LA,
Ar is phenyl or pyridyl, which is unsubstituted or mono- or disubstituted by Hal, LA or O(LA),
in Subformula 13
X is N,
Y is N or CH,
E is a methyl linker which is substituted by aminomethyl, wherein the amino group of the aminomethyl is unsubstituted, or mono- or disubstituted by LA, or E is a methyl linker which is substituted by (azetidin-1-yl)methyl,
Ar is phenyl or pyridyl, which is unsubstituted or mono- or disubstituted by Hal, LA or O(LA),
R$^1$ is Hal, LA, O(LA), Cyc$^1$ or Cyc$^2$,
and pharmaceutically acceptable salts, solvates, solvates of salts, or prodrugs thereof.

In yet further preferred embodiments the substituents designated R$^1$, in Formula (I), are set out in Table 1.

TABLE 1

Preferred substituents for R$^1$ in Formula (I):

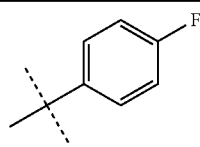

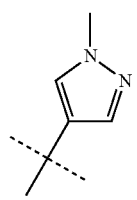

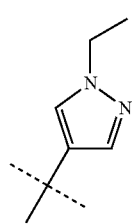

TABLE 1-continued

Preferred substituents for R$^1$ in Formula (I):

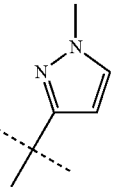

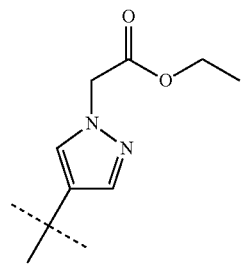

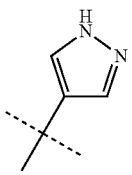

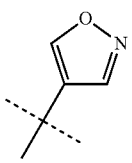

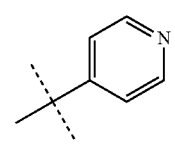

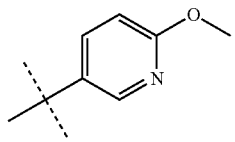

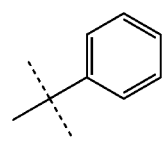

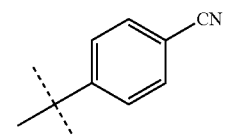

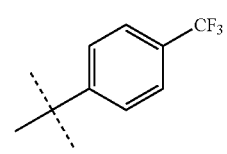

TABLE 1-continued
Preferred substituents for R¹ in Formula (I):
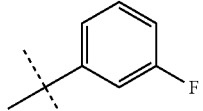
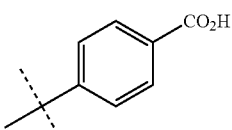
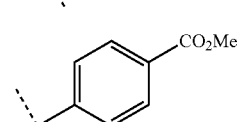
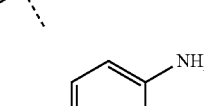
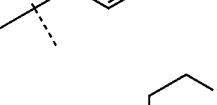
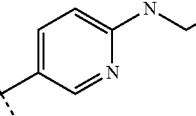
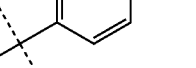
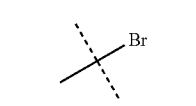
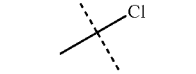
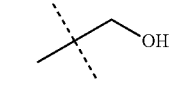
TABLE 1-continued
Preferred substituents for R¹ in Formula (I):
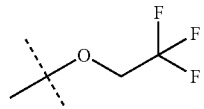
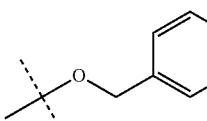
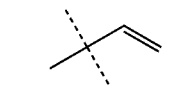
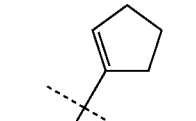
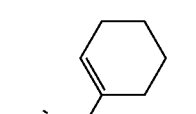
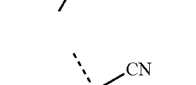
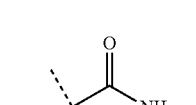
In other preferred embodiments the substituents designated Ar, in Formula (I), are set out in Table 2.

TABLE 2
Preferred substituents for Ar in Formula (I):
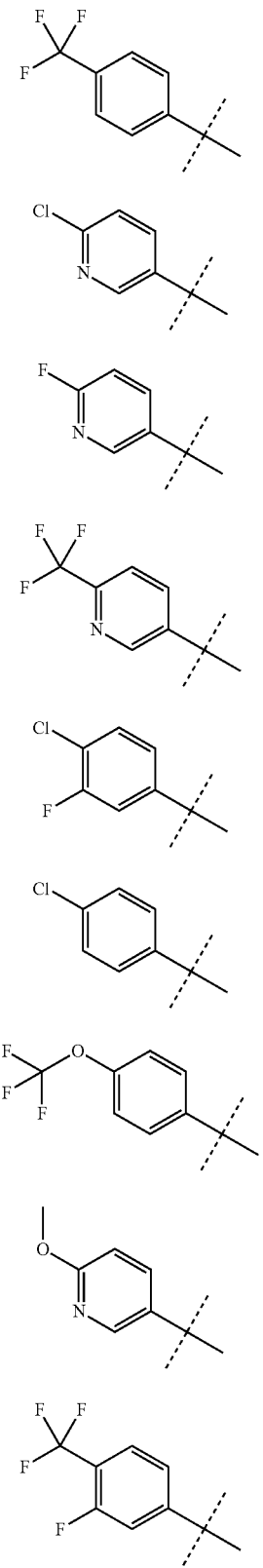
TABLE 2-continued
Preferred substituents for Ar in Formula (I):
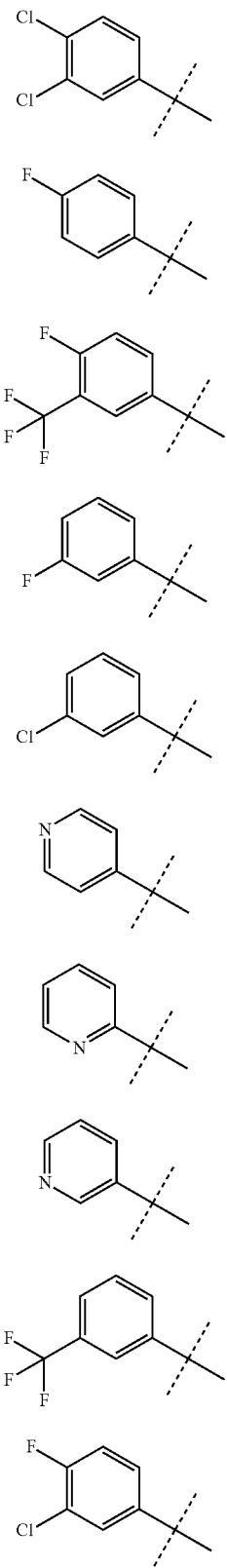

TABLE 2-continued
Preferred substituents for Ar in Formula (I):
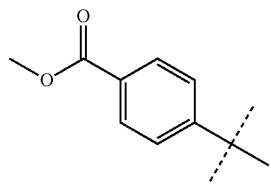
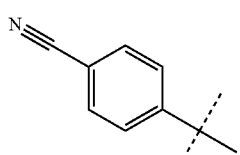
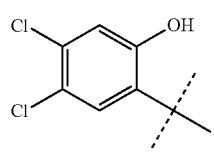
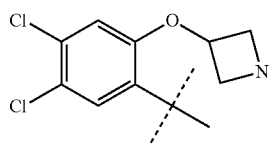
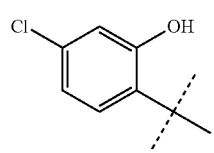
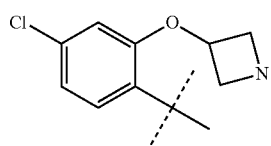
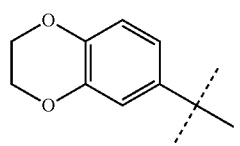
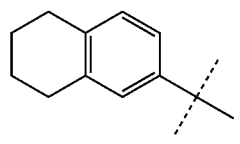
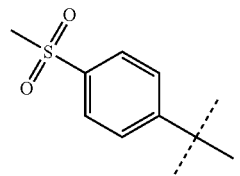
TABLE 2-continued
Preferred substituents for Ar in Formula (I):
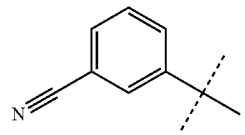
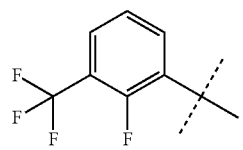
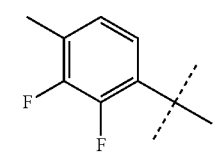
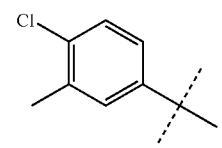
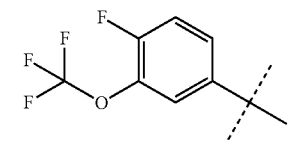
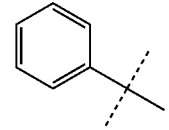
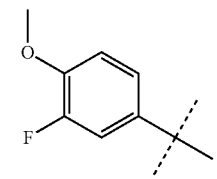
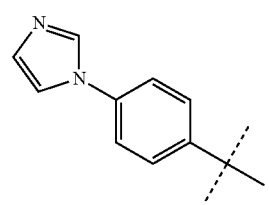
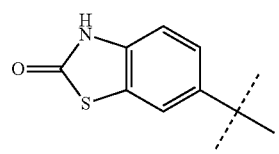

TABLE 2-continued
Preferred substituents for Ar in Formula (I):
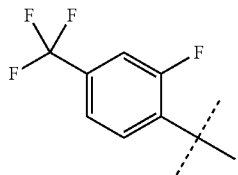
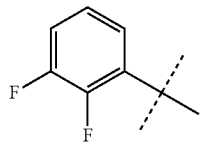
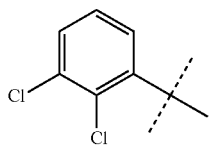
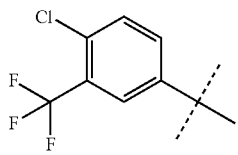
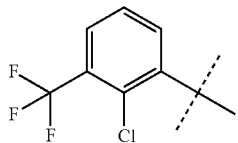
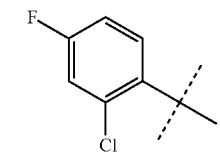
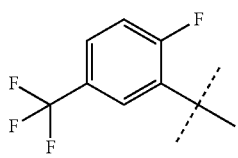
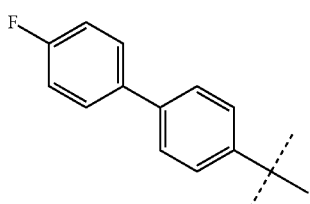
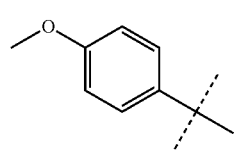
TABLE 2-continued
Preferred substituents for Ar in Formula (I):
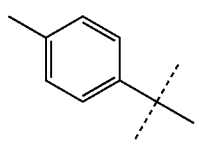
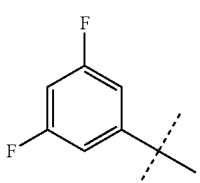
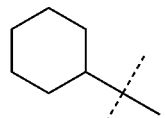
In other preferred embodiments the substituents designated E, in Formula (I), are set out in Table 3.
TABLE 3
Preferred substituents for E in Formula (I):
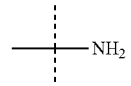
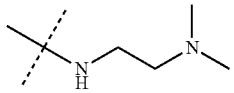
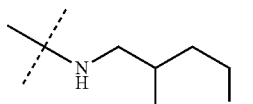
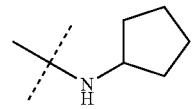
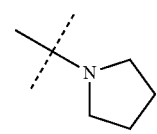

TABLE 3-continued
Preferred substituents for E in Formula (I):
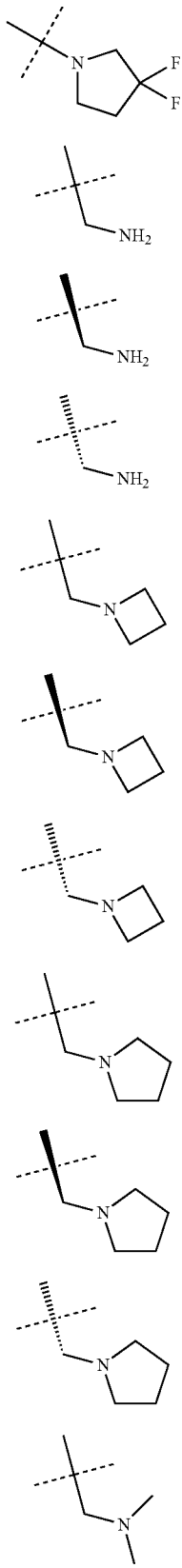
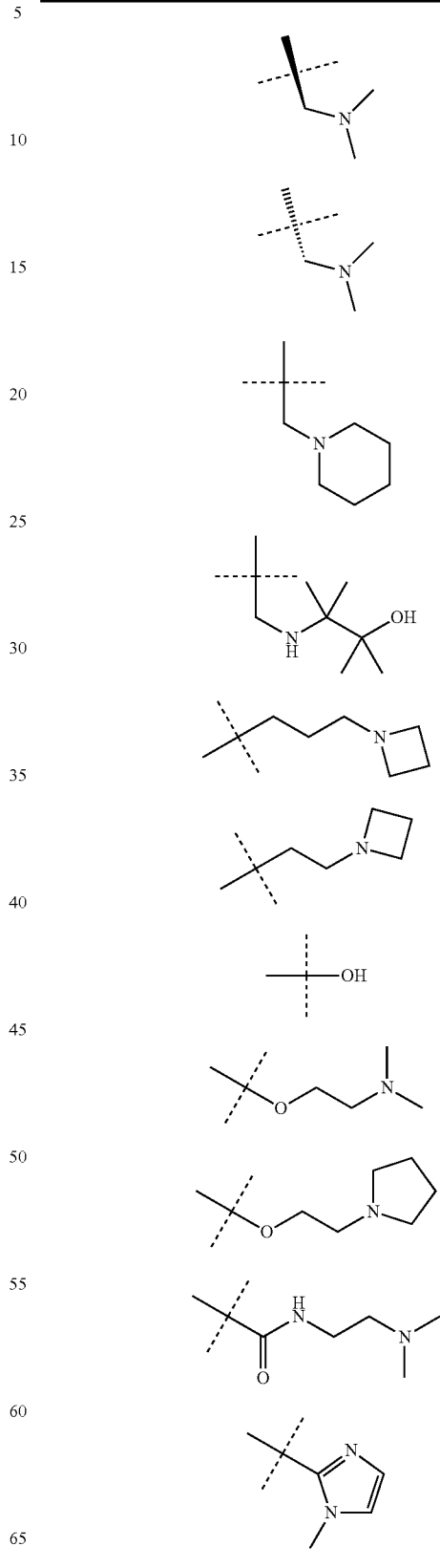

TABLE 3-continued

Preferred substituents for E in Formula (I):

————≡N

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "substituted" preferably relates to the substitution by the above-mentioned substituents, where a plurality of different degrees of substitution are possible, unless indicated otherwise.

All physiologically acceptable salts, derivatives, solvates, solvates of salts, and stereoisomers of these compounds, including mixtures thereof in all ratios, are also in accordance with the invention.

The compounds of Formula (I) may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3. A method for the resolution of racemates containing ester groups (for example acetyl esters) is the use of enzymes, in particular esterases.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other p70S6K inhibitors. The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. Preferably, the cancer to be treated is chosen from breast, colorectal, lung, prostate or pancreatic cancer or glioblastoma.

The invention also relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and sclerodema, diabetes, diabetic retinopathy, retinopathy of prematurity and age-related macular degeneration.

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, such as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.2 milligrams to about 2000 milligrams, preferably from about 0.5 milligram to about 1000 milligrams. In the case of a 70 kg adult human, the total daily dose will generally be from about 0.5 milligrams to about 1000 milligrams. These aforementioned dosage regimens may be adjusted to provide the optimal therapeutic response.

The invention also relates to a set (kit) consisting of separate packs of
a) an effective amount of a compound according to the invention or a physiologically acceptable salt, solvate or prodrug thereof, and
b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

EXPERIMENTAL SECTION

Some abbreviations that may appear in this application are as follows:

ABBREVIATIONS

| Designation | |
|---|---|
| ACN | acetonitrile |
| ATP | Adenosine triphosphate |
| b | Broad peak |
| d | Doublet |
| DMSO | dimethylsulfoxide |
| DIEA | N,N-Diisopropylethylamine |
| DTT | dithiothreitol |
| EDTA | Ethylenediaminetetraacetic acid |
| equiv. | equivalents |
| Et | ethyl |
| h | hour |
| HEPES | 4-(2-hydroxyethyl)-1-piperazineethanesulfonic acid |
| HPLC | High pressure liquid chromatography |
| LC/MS | Liquid chromatography coupled to mass spectrometry |
| m | multiplet |
| M | Molecular ion |
| m/z | Mass-to-charge ratio |
| Me | methyl |
| min | minute |

-continued

| Designation | |
|---|---|
| MS | Mass spectrometry |
| N | Normal (unit of concentration) |
| NMO | 4-methylmorpholine N-oxide |
| NMR | Nuclear Magnetic Resonance |
| PG | Protecting group |
| psi | Pounds per square inch |
| q | Quartette (or quartet) |
| Rf | Retention factor |
| RT | Room temperature |
| Rt. | Retention time |
| s | Singlet |
| Tert | Tertiary |
| TEA | Triethylamine |
| TFA | Trifluoroacetic acid |
| THAB | Tetrahexylammonium bromide |
| THF | Tetrahydrofuran |
| UV | ultraviolet |
| VIS | visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above.

Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

Analytical Methodology
Analytical LC/MS was Performed Using the Following Three Methods:
Method A:
A Discovery $C^{18}$, 5 µm, 3×30 mm column was used at a flow rate of 400 µL/min, sample loop 5 µL, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B:
A Waters Symmetry $C^{18}$, 3.5 µm, 4.6×75 mm column at a flow rate of 1 mL/min, sample loop 10 µL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+ mode with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

Method C:
Gradient: 4.2 min/Flow: 2 ml/min 99:01-0:100 Water+ 0.1% (Vol.) TFA; Acetonitril+0.1% (Vol.) TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

Analytical Chiral HPLC
Analytical chiral HPLC was performed using a ChiralPak AD-H column (250×4.6 mm) from Daicel Chemical Industries, Ltd. on an Agilent 1100 Series system. The method used a 5.0 µL injection volume, with a flow rate of 1 mL/min of 100% methanol for 15 min at 25° C., and UV-detection at 254 and 280 nm.

Preparative HPLC
Preparative HPLC was performed using either a Waters Atlantis $dC_{18}$ OBD™ 10 µM (30×250 mm) column or a Waters Sunfire Prep $C_{18}$ OBD 10 µM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

The present invention also relates to processes for manufacturing the compounds of Formula (I) according to the hereinafter described schemes and working examples.

The working examples presented below are intended to illustrate particular embodiments of the invention, and are not intended to limit the scope of the specification or the claims in any way.

Synthetic Schemes Describing Intermediates and End Product Compounds

Pyrimidine chloride intermediates were either commercially available or prepared according to the synthetic routes outlined in Scheme 1 and Scheme 2.

Scheme 1

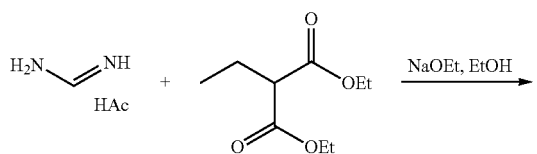

25

-continued

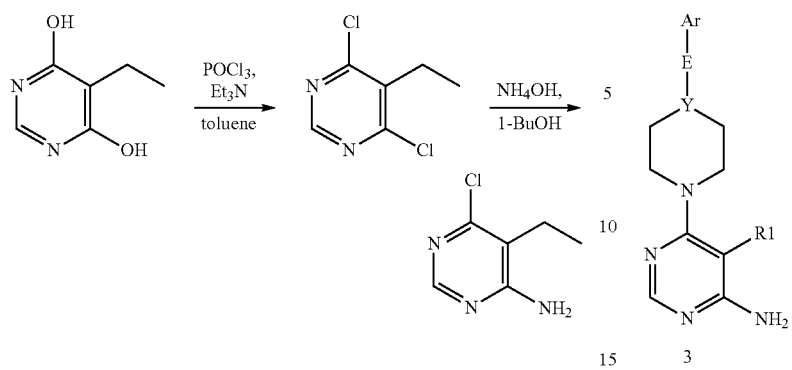

Formamidine acetate was reacted with diethyl-ethylmalonate in the presence of sodium ethoxide in dry ethanol to yield 5-ethylpyrimidine-4,6-diol, which was converted to 4,6-Dichloro-5-ethylpyrimidine by POCl3 in the presence of TEA in toluene. 4,6-Dichloro-5-ethylpyrimidine was then reacted with aqueous ammonia in n-butanol at 100° C. to afford 4-amino-5-ethyl-6-chloropyrimidine.

Scheme 2

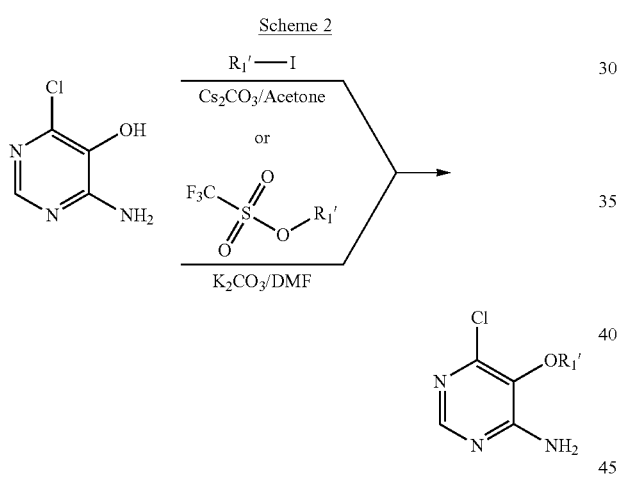

4-amino-6-chloropyrimidin-5-ol was reacted with alkylated regents to provide the desired pyrimidine chloride intermediates.

Scheme 3

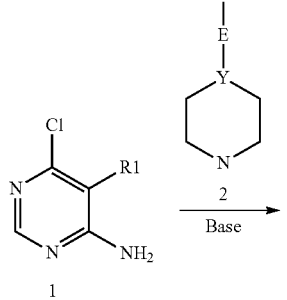

26

-continued

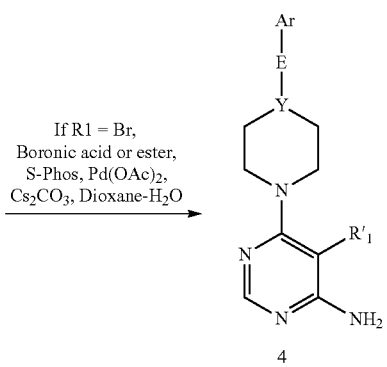

The pyrimidine chloride intermediates 1 reacted with secondary amines 2 in the presence of base to provide compounds 3. A Suzuki coupling is performed if R1 is bromo of compounds 3 to afford compounds 4.

Scheme 4

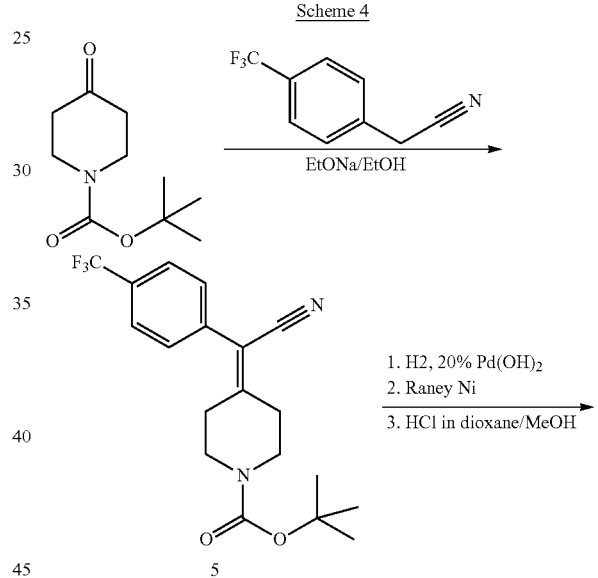

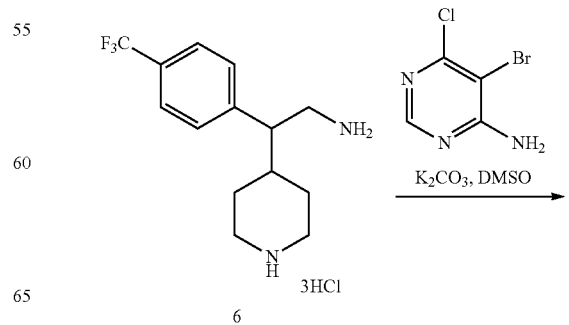

-continued

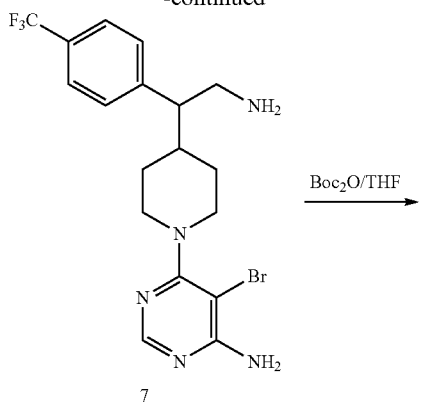

7

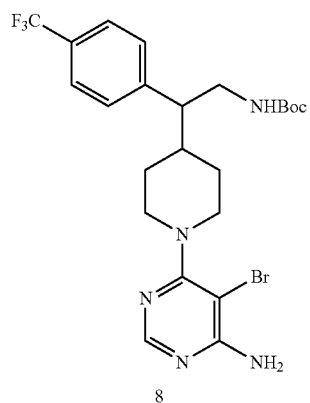

8

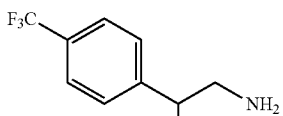
1. Suzuki coupling
2. HCl in dioxane/MeOH

9

Tert-butyl-4 oxopiperidone-1-carboxylate was treated with 2-(4-(trifluoromethyl)phenyl)acetonitrile under basic condition to form compound 5. Hydrogenation of compound 5 by using Pd(OH)2 as catalyst to reduce the double bond and Raney Ni as catalyst to convert cyanide to amine, followed by de-Boc generated intermediate 6, which was coupling with 5-bromo-6-chloropyrimidin-4-amine to yield compound 7. The primary amine 7 was protected by Boc to give intermediate 8, which was performed a Suzuki coupling, followed by Boc deprotection to affod compounds 9.

Scheme 5

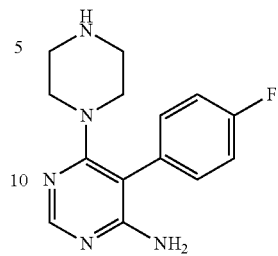
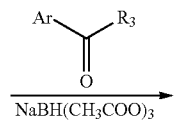

5

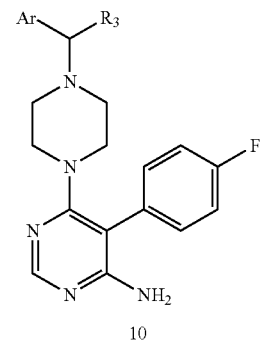

10

5-(4-fluorophenyl)-6-(piperazin-1-yl)pyrimidin-4-amine was reacted with aryl aldehydes or ketones under reductive amination condition to generate desired compounds 10.

Scheme 6

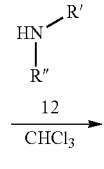

11

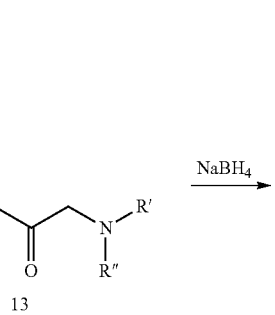

13

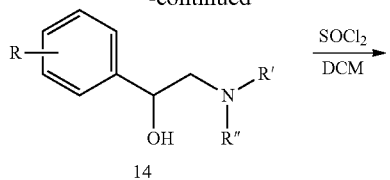
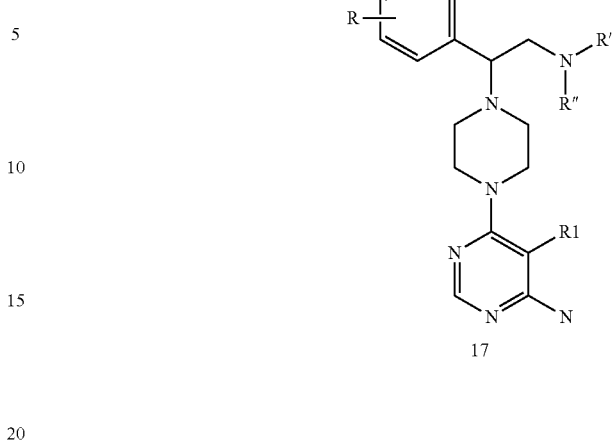
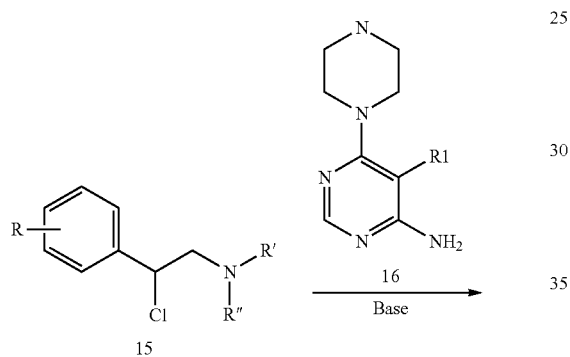
The displacement of bromides 11 with secondary amines 12 provided ketones 13, which was reduced to alcohols 14. Alcohols 14 were converted to the corresponding chlorides 15 by thionyl chloride. Chlorides 15 were reacted with piperazine intermediates 16 to afford the desired the products 17.
Scheme 7
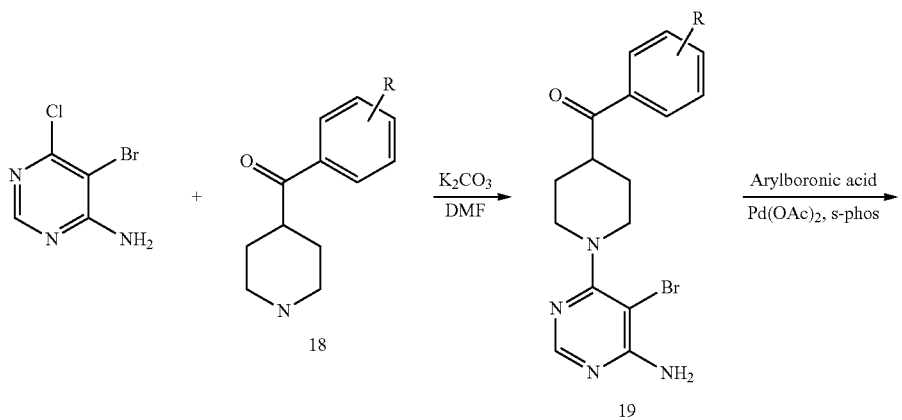

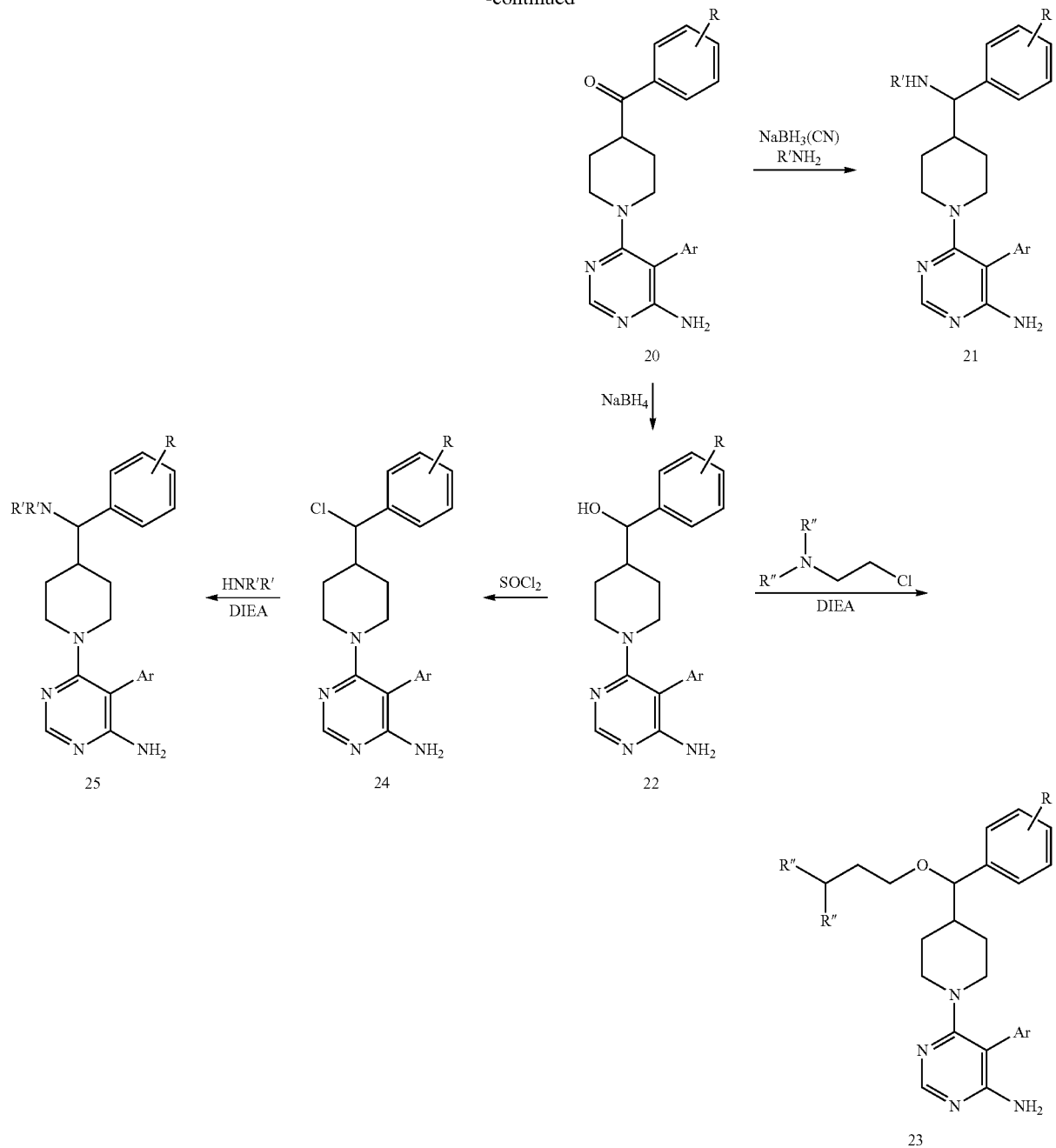

5-Bromo-6-chloro-pyrimidine-4-ylamine was reacted with secondary amines 18 in the presence of base to provide the bromide intermediates 19. A Suzuki coupling is performed with the bromide intermediates 19 and boronic acid or ester to afford the ketone intermediates 20. Reductive amination of the ketone intermediates 20 with amines in the presence of sodium cyanoborohydride provided the desired products 21. Reduction of keton intermediates 20 with sodium borohydride gave the second alcohols 22, which can be further converted to compounds 23 by alkylating with chlorides. Compounds 25 were obtained via their chlorides intermediates 24 from the corresponding alcohols 22.

Scheme 8

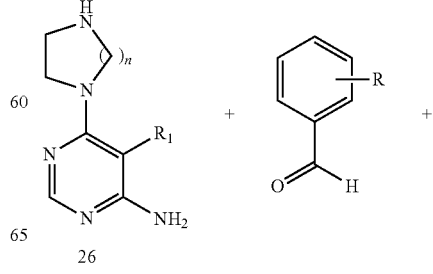

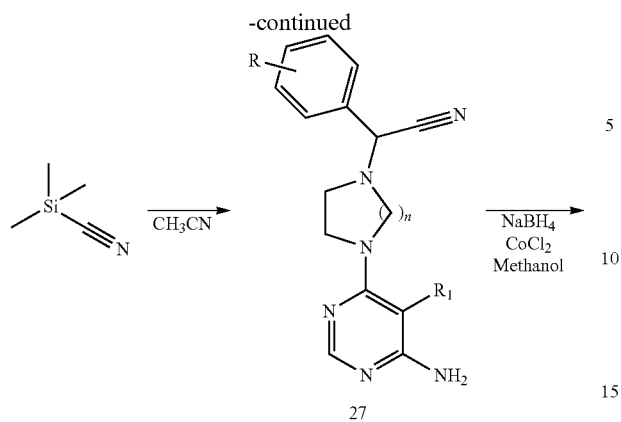

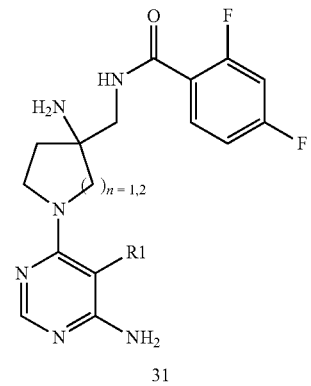

5-Bromo-6-chloro-pyrimidine-4-ylamine was reacted with secondary amines 29 in the presence of base to provide the bromides 30. A Suzuki coupling was then performed with the bromides 30 and boronic acid or ester to afford compounds 31.

Scheme 10

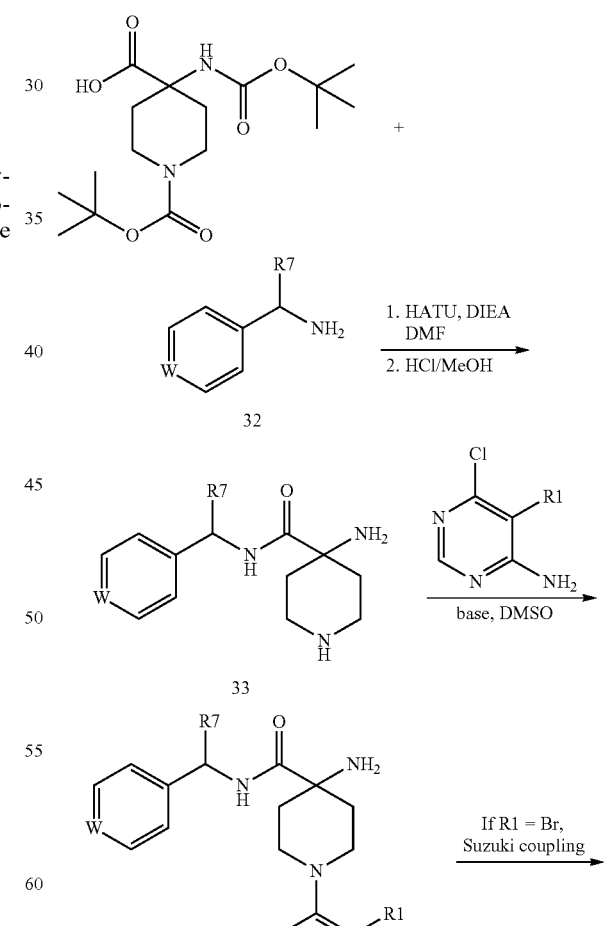

The Strecker reaction with 4-heterocyclic-6-aminopyrimidine 26, aryl-aldehydes, and trimethylsilyl cyanide provided the nitriles 27. Reduction of the nitriles afforded the primary amine as desired products 28.

Scheme 9

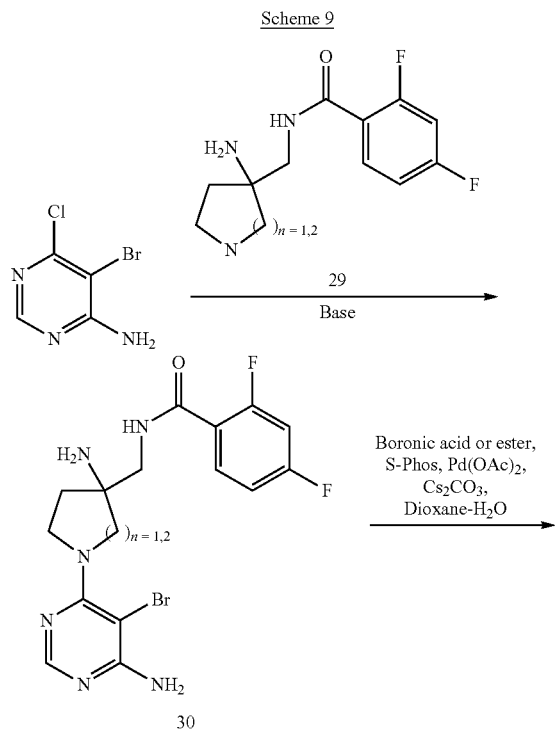

-continued

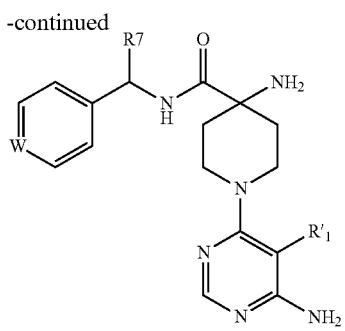

Amide coupling of 1-(tert-butoxycarbonyl)-4-((tert-butoxycarbonyl)amino)piperidine-4-carboxylic acid with amines 32 followed by Boc deprotection generated amine intermediate 33, which was reacted with 6-amino-5-substituted-4-chloro pyrimidines provided compounds 34. A Suzuki coupling was then performed if R1 of compounds 34 is bromine to afford compounds 35.

Examples

Examples 136 and 209-213 have been purposely omitted given a discontinuity in the clerical numbering of the compounds as described in the instant application.

Examples (1) to (50) were prepared according to Scheme 3.

6-{4-[2-Amino-1-(4-trifluoromethyl-phenyl)-ethyl]-piperazin-1-yl}-5-bromo-pyrimidin-4-ylamine ("1")

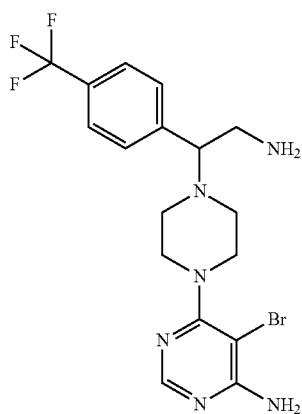 [SMILES: NCC(c1ccc(C(F)(F)F)cc1)N1CCN(c2ncnc(N)c2Br)CC1]

Intermediate (1.1): 2-Piperazin-1-yl-2-(4-trifluoromethyl-phenyl)-ethylamine hydrochloride A mixture of 4-[2-Amino-1-(4-trifluoromethyl-phenyl)-ethyl]-piperazine-1-carboxylic acid tert-butyl ester (185 mg; 0.5 mmol; 1.0 eq.) and 4M hydrogen chloride in dioxane (1.8 ml; 7.4 mmol; 15 eq.) in Methanol (3.00 ml) was stirred at room temperature overnight. Ether was added to the reaction mixture. The precipitate was filtered, washed with ether and dried to yield 2-piperazin-1-yl-2-(4-trifluoromethyl-phenyl)-ethylamine hydrochloride salt as off-white solid in 67% yield.

A mixture of 5-bromo-6-chloropyrimidin-4-amine (51.6 mg; 0.24 mmol, 1.0 eq.), intermediate (1.1) (100.0 mg; 0.24 mmol, 1.0 eq.) and potassium carbonate (97.5 mg; 0.7 mmol; 3.0 eq.) in DMSO (2.00 ml) was heated at 60° C. for 8 h. The reaction mixture was purified by pre-HPLC (Waters, basic condition) to afford the title compound as white solid in 70% yield. LC-MS: (M+1=445, obsd.=445).

6-{4-[2-Amino-1-(4-trifluoromethyl-phenyl)-ethyl]-piperazin-1-yl}-5-(4-fluoro-phenyl)-pyrimidin-4-ylamine ("2")

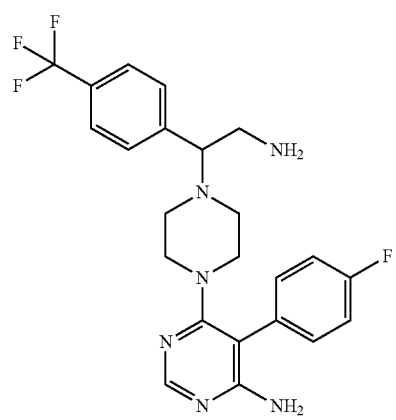 [SMILES: NCC(c1ccc(C(F)(F)F)cc1)N1CCN(c2ncnc(N)c2-c2ccc(F)cc2)CC1]

A mixture of 6-{4-[2-Amino-1-(4-trifluoromethyl-phenyl)-ethyl]-piperazin-1-yl}-5-bromo-pyrimidin-4-ylamine (110.00 mg; 0.25 mmol; 1.0 eq.), (4-fluorophenyl)boronic acid (103.7 mg; 0.74 mmol; 3.0 eq.), palladium(2+) acetate (5.5 mg; 0.02 mmol; 0.1 eq.), dicyclohexyl(2',6'-dimethoxybiphenyl-2-yl)phosphine (20.2 mg; 0.05 mmol; 0.2 eq.) and cesium carbonate (241.4 mg; 0.74 mmol; 3.0 eq.) in dioxane (5.00 ml) and water (0.50 ml) in a sealed tube was stirred at 100° C. overnight. The crude was purified by Reverse Phase chromatography (Waters, basic condition) to afford the title compound as a white solid in 75% yield. LC-MS: (M+1=461, obsd.=461).

6-{4-[(S)-2-Amino-1-(4-trifluoromethyl-phenyl)-ethyl]-piperazin-1-yl}-5-(4-fluoro-phenyl)-pyrimidin-4-ylamine ("3")

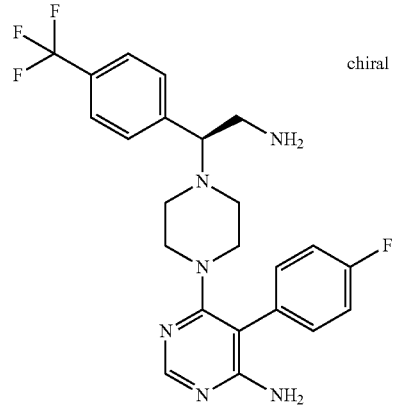 [SMILES: NC[C@H](c1ccc(C(F)(F)F)cc1)N1CCN(c2ncnc(N)c2-c2ccc(F)cc2)CC1]

The title compound was obtained via SFC chiral separation of Example (2). LC-MS: (M+1=461, obsd.=461).

6-{4-[(R)-2-Amino-1-(4-trifluoromethyl-phenyl)-ethyl]-piperazin-1-yl}-5-(4-fluoro-phenyl)-pyrimidin-4-ylamine ("4")

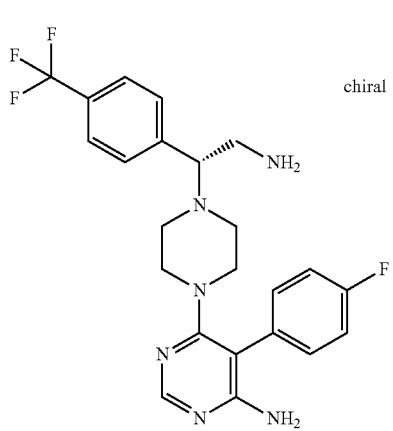 [SMILES: NC[C@@H](c1ccc(C(F)(F)F)cc1)N1CCN(c2ncnc(N)c2-c2ccc(F)cc2)CC1]

The title compound was obtained via SFC chiral separation of Example (2). LC-MS: (M+1=461, obsd.=461).

6-[4-(2-Amino-1-phenyl-ethyl)-piperazin-1-yl]-5-bromo-pyrimidin-4-ylamine ("5")

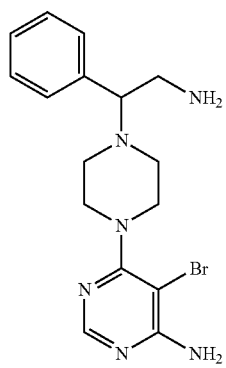 [SMILES: NCC(c1ccccc1)N1CCN(c2ncnc(N)c2Br)CC1]

The title compound was prepared in an analogous manner as Example (1) by using 4-[2-amino-1-phenylethyl]-piperazine-1-carboxylic acid tert-butyl ester instead of 4-[2-amino-1-(4-trifluoromethylphenyl)-ethyl]-piperazine-1-carboxylic acid tert-butyl ester. LC-MS: (M+1=377, obsd.=377).

6-[4-(2-Amino-1-phenyl-ethyl)-piperazin-1-yl]-5-(4-fluoro-phenyl)-pyrimidin-4-ylamine ("6")

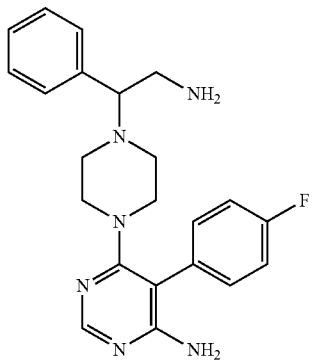 [SMILES: NCC(c1ccccc1)N1CCN(c2ncnc(N)c2-c2ccc(F)cc2)CC1]

The title compound was prepared in an analogous manner as Example (2) by using 6-{4-[2-amino-1-phenyl)-ethyl]-piperazin-1-yl}-5-bromo-pyrimidin-4-ylamine instead of 6-{4-[2-amino-1-(4-trifluoromethylphenyl)-ethyl]-piperazin-1-yl}-5-bromo-pyrimidin-4-ylamine. LC-MS: (M+1=393, obsd.=393).

6-{4-[2-Amino-1-(4-trifluoromethyl-phenyl)-ethyl]-piperazin-1-yl}-5-(1H-pyrazol-4-yl)-pyrimidin-4-ylamine ("7")

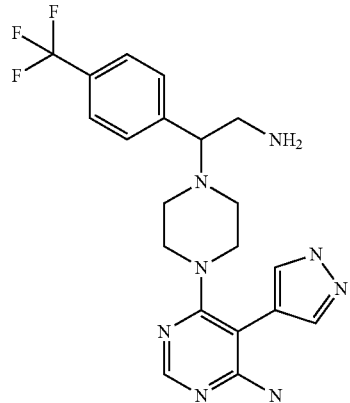 [SMILES: NCC(c1ccc(C(F)(F)F)cc1)N1CCN(c2ncnc(N)c2-c2cn[nH]c2)CC1]

The title compound was prepared in an analogous manner as Example (2). LC-MS: (M+1=433, obsd.=433).

(S)-6-(4-(2-amino-1-(4-(trifluoromethyl)phenyl)
ethyl)piperazin-1-yl)-5-(1H-pyrazol-4-yl)pyrimidin-
4-amine ("8")

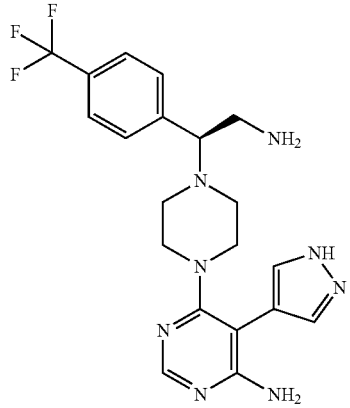 [SMILES: NC[C@H](c1ccc(C(F)(F)F)cc1)N1CCN(c2ncnc(N)c2-c2cn[nH]c2)CC1]

The title compound was obtained by chiral separation with SFC column of Example (7). LC-MS: (M+1=433, obsd.=433).

(R)-6-(4-(2-amino-1-(4-(trifluoromethyl)phenyl)
ethyl)piperazin-1-yl)-5-(1H-pyrazol-4-yl)pyrimidin-
4-amine ("9")

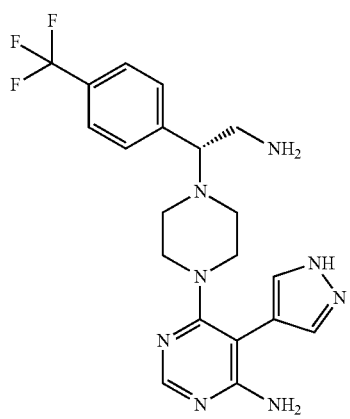

The title compound was obtained by chiral separation with SFC column of Example (7). LC-MS (M+1=433, obsd.=433).

5-(4-fluorophenyl)-6-(4-(2-(pyrrolidin-1-yl)-1-(4-
(trifluoromethyl)-phenyl)-ethyl)-piperazin-1-yl)-
pyrimidin-4-amine ("10")

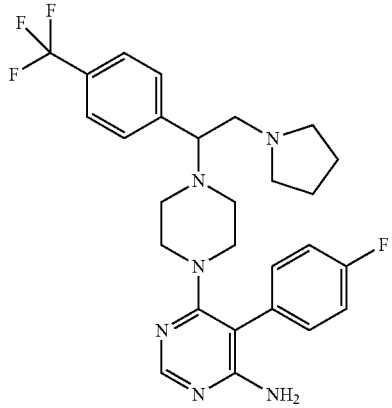 [SMILES: Nc1ncnc(N2CCN(C(CN3CCCC3)c3ccc(C(F)(F)F)cc3)CC2)c1-c1ccc(F)cc1]

Intermediate (10.1): 1-(2-(pyrrolidin-1-yl)-1-(4-
(trifluoromethyl)phenyl)ethyl)piperazine hydrochlo-
ride salt In a dry microwave vial was added 4-[2-Amino-1-(4-trifluoromethyl-phenyl)-ethyl]-piperazine-1-carboxylic acid tert-butyl ester (160.0 mg; 0.43 mmol; 1.0 eq.), Potassium carbonate (296.1 mg; 2.14 mmol; 5.0 eq.), 1,4-Dibromo-butane (55.9 µl; 0.47 mmol; 1.1 eq.) and. The vial was capped and connected to a vacuum for 10 sec. before it was influx with N2. The white turbid mixture was stirred at 83° C. overnight. No SM was detected. The crude mixture was filtered, concentrated and purified via 10 g KPNH column to afford the 68 mg Boc protected Intermediate (8.1). To a 25 mL flask containing the obtained Boc protected title compound in MeOH (5 mL) was added hydrogen chloride (0.8 ml; 1.61 mmol; 10.0 eq.) at 0° C. slowly. The obtained solution was warmed up to room temperature and stirred overnight. LCMS didn't detect any SM. The crude mixture was concentrated and directed used in the next step. LC-MS: (M+1=328, obsd.=328).

Intermediate (10.2): 5-bromo-6-(4-(2-(pyrrolidin-1-
yl)-1-(4-(trifluoromethyl)phenyl)-ethyl)piperazin-1-
yl)pyrimidin-4-amine Intermediate (10.2) was prepared in an analogous manner as Example (1) using Intermediate (10.1). LC-MS: (M+1=499, obsd.=499).

Example (10) was prepared in an analogous manner as Example (2) using Intermediate (10.2). LC-MS: (M+1=515, obsd.=515).

5-bromo-6-(4-(2-(piperidin-1-yl)-1-(4-(trifluoromethyl)phenyl)ethyl)piperazin-1-yl)pyrimidin-4-amine ("11")

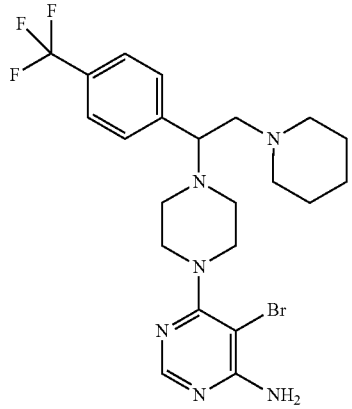 [SMILES: Nc1ncnc(N2CCN(C(CN3CCCCC3)c3ccc(C(F)(F)F)cc3)CC2)c1Br]

Intermediate (11.1): 1-(2-(piperidin-1-yl)-1-(4-(trifluoromethyl)phenyl)ethyl)piperazine hydrochloride salt Intermediate (11.1) (315 mg) was prepared in an analogous manner as Intermediate (10.1) using 1,5-dibromopentane (120.38 µl; 0.88 mmol; 1.1 eq.) instead of 1,4-dibromo butane. The concentrated crude product was directly used in the next step. LC-MS: (M+1=342, obsd.=342).

Example (11) was prepared in an analogous manner as Example (1) using Intermediate (9.1). LC-MS: (M+1=513, obsd.=513).

5-(4-Fluoro-phenyl)-6-{4-[2-piperidin-1-yl-1-(4-trifluoromethyl-phenyl)-ethyl]-piperazin-1-yl}-pyrimidin-4-ylamine ("12")

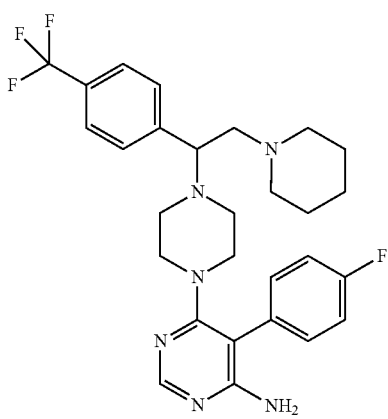 [SMILES: Nc1ncnc(N2CCN(C(CN3CCCCC3)c3ccc(C(F)(F)F)cc3)CC2)c1-c1ccc(F)cc1]

The title compound was prepared in an analogous manner as Example (2). LC-MS: (M+1=529, obsd.=529).

5-(4-Fluoro-phenyl)-6-[4-(4-trifluoromethyl-benzyl)-piperazin-1-yl]-pyrimidin-4-ylamine ("13")

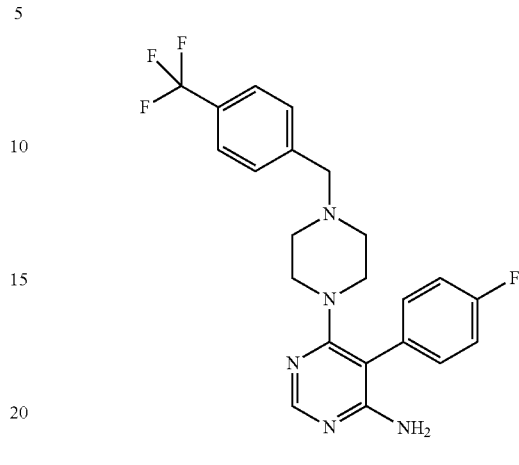

Intermediate (13.1): 4-(6-Amino-5-bromo-pyrimidin-4-yl)-piperazine-1-carboxylic acid tert-butyl ester Intermediate (13.1) was prepared in an analogous manner as Example (1) using Piperazine-1-carboxylic acid tert-butyl ester instead of 4-[2-amino-1-(4-trifluoromethylphenyl)-ethyl]-piperazine. LC-MS: (M+1=358, obsd.=358).

Intermediate (13.2): 4-[6-Amino-5-(4-fluoro-phenyl)-pyrimidin-4-yl]-piperazine-1-carboxylic acid tert-butyl ester Intermediate (13.2) was prepared in an analogous manner as Example (2). LC-MS: (M+1=374, obsd.=374).

Intermediate (13.3): 5-(4-Fluoro-phenyl)-6-piperazin-1-yl-pyrimidin-4-ylamine The mixture of the Intermediate (10.2) (370 mg; 1 mmol; 1.0 eq.), 4M hydrogen chloride in dioxane (2.5 mL, 10 mmol, 10 eq.) in MeOH (2.0 ml) is stirred at room temperature for 3 h. The reaction mixture is diluted with ether. The precipitate was filtered and washed with ether to afford the Intermediate (10.3) as HCl salt. LC-MS: (M+1=274, obsd.=274).

The mixture of Intermediate (13.3) (60.0 mg; 0.22 mmol; 1.0 eq.), 1-bromomethyl-4-trifluoromethylbenzene (52.48 mg; 0.22 mmol; 1.00 eq.) and DIPEA (0.04 ml; 0.26 mmol; 1.2 eq.) in THF (2.0 ml) is stirred at room temperature overnight. The reaction mixture was concentrated and purified by pre-HPLC (Waters, basic condition) to yield the title compound as a white solid in 76% yield. LC-MS: (M+1=432, obsd.=432).

5-bromo-6-(4-(2-(dimethylamino)-1-(4-(trifluoromethyl)phenyl)ethyl)piperazin-1-yl)pyrimidin-4-amine ("14")

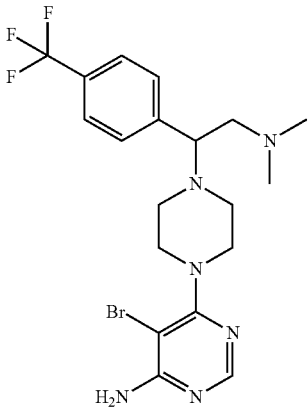 [SMILES: CN(C)CC(c1ccc(C(F)(F)F)cc1)N1CCN(c2ncnc(N)c2Br)CC1]

The title compound was prepared in an analogous manner as Example (1) by using N,N-dimethyl-2-(piperazin-1-yl)-2-(4-(trifluoromethyl)phenyl)ethanamine instead of 2-piperazin-1-yl-2-(4-trifluoromethyl-phenyl)-ethylamine. LC-MS: (M+1=474, obsd.=474)

6-(4-(2-(dimethylamino)-1-(4-(trifluoromethyl)phenyl)ethyl)piperazin-1-yl)-5-(4-fluorophenyl)pyrimidin-4-amine ("15")

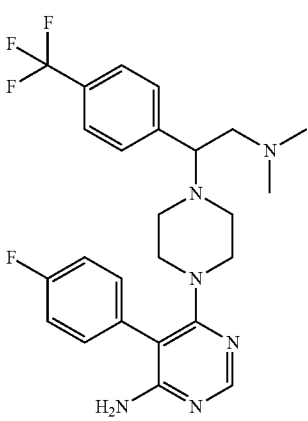 [SMILES: CN(C)CC(c1ccc(C(F)(F)F)cc1)N1CCN(c2ncnc(N)c2-c2ccc(F)cc2)CC1]

The title compound was prepared in an analogous manner as Example (2) by using 5-bromo-6-(4-(2-(dimethylamino)-1-(4 (trifluoromethyl)phenyl)ethyl)piperazin-1-yl)pyrimidin-4-amine instead of 6-(4-(2-amino-1-(4-(trifluoromethyl)phenyl)ethyl)-piperazin-1-yl)-5-bromopyrimidin-4-amine. LC-MS: (M+1=489, obsd.=489)

(S)-6-(4-(2-(dimethylamino)-1-(4-(trifluoromethyl)phenyl)ethyl)piperazin-1-yl)-5-(4-fluorophenyl)pyrimidin-4-amine ("16")

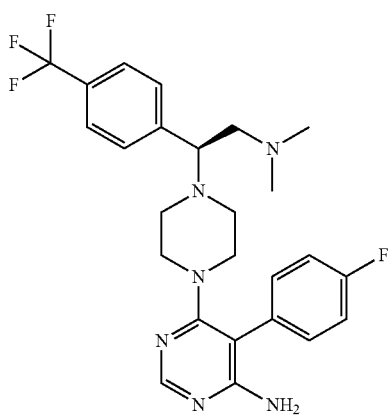 [SMILES: CN(C)C[C@H](c1ccc(C(F)(F)F)cc1)N1CCN(c2ncnc(N)c2-c2ccc(F)cc2)CC1]

The title compound was obtained via SFC chiral separation of Example (15). LC-MS: (M+1=489, obsd.=489).

(R)-6-(4-(2-(dimethylamino)-1-(4-(trifluoromethyl)phenyl)ethyl)piperazin-1-yl)-5-(4-fluorophenyl)pyrimidin-4-amine ("17")

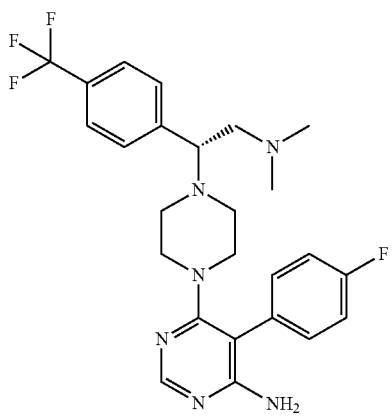 [SMILES: CN(C)C[C@@H](c1ccc(C(F)(F)F)cc1)N1CCN(c2ncnc(N)c2-c2ccc(F)cc2)CC1]

The title compound was obtained via SFC chiral separation of Example (15). LC-MS: (M+1=489, obsd.=489).

2-(4-(6-amino-5-(4-fluorophenyl)pyrimidin-4-yl) piperazin-1-yl)-N-(2-(dimethylamino)ethyl)-2-(4-(trifluoromethyl)phenyl)acetamide ("18")

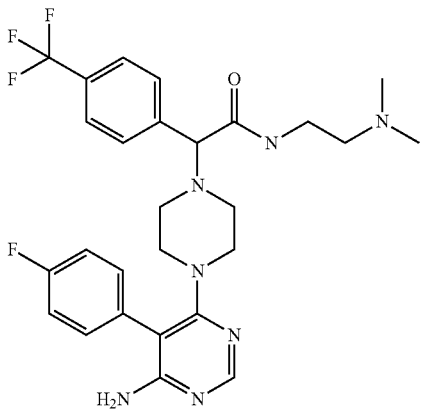 [SMILES: CN(C)CCNC(=O)C(c1ccc(C(F)(F)F)cc1)N1CCN(c2ncnc(N)c2-c2ccc(F)cc2)CC1]

The title compound was prepared in an analogous manner as Example (2) by using 2-(4-(6-amino-5-bromopyrimidin-4-yl)piperazin-1-yl)-N-(2-(dimethylamino)ethyl)-2-(4-(trifluoromethyl)phenyl)acetamide instead of 6-(4-(2-amino-1-(4-(trifluoromethyl)phenyl)ethyl)piperazin-1-yl)-5-bromopyrimidin-4-amine. LC-MS: (M+1=546, obsd.=546)

6-(4-(2-amino-1-(4-(trifluoromethyl)-phenyl)ethyl) piperazin-1-yl)-5-vinylpyrimidin-4-amine ("19")

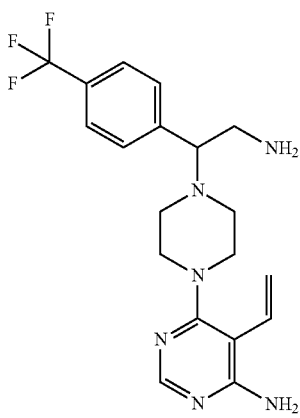 [SMILES: C=Cc1c(N)ncnc1N1CCN(C(CN)c2ccc(C(F)(F)F)cc2)CC1]

The title compound was prepared in an analogous manner as Example (2) by using 4,4,5,5-tetramethyl-2-vinyl-1,3,2-dioxaborolane instead of 4-fluorophenyl boronic acid. LC-MS: (M+1=394, obsd.=394)

5-(6-aminopyridin-3-yl)-6-(4-(2-(dimethylamino)-1-(4-(trifluoromethyl)-phenyl)ethyl)piperazin-1-yl) pyrimidin-4-amine ("20")

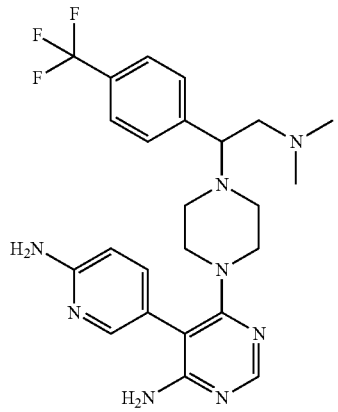 [SMILES: CN(C)CC(c1ccc(C(F)(F)F)cc1)N1CCN(c2ncnc(N)c2-c2ccc(N)nc2)CC1]

The title compound was prepared in an analogous manner as Example (15) by using (6-aminopyridin-3-yl) boronic acid instead of 4-fluorophenyl boronic acid. LC-MS: (M+1=487, obsd.=487)

6-(4-(2-(dimethylamino)-1-(4-(trifluoromethyl)phenyl)ethyl)piperazin-1-yl)-5-vinylpyrimidin-4-amine ("21")

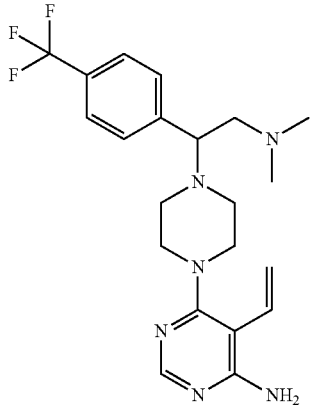 [SMILES: C=Cc1c(N)ncnc1N1CCN(C(CN(C)C)c2ccc(C(F)(F)F)cc2)CC1]

The title compound was prepared in an analogous manner as Example (15) by using 4,4,5,5-tetramethyl-2-vinyl-1,3,2-dioxaborolane instead of 4-fluorophenyl boronic acid. LC-MS: (M+1=421, obsd.=421)

2-(4-(4-amino-6-(4-(2-(dimethylamino)-1-(4-(trifluoromethyl)phenyl)ethyl)-piperazin-1-yl)pyrimidin-5-yl)phenyl)propan-2-ol ("22")

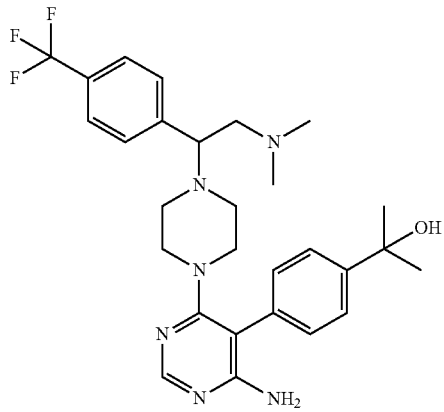 [SMILES: CN(C)CC(c1ccc(C(F)(F)F)cc1)N1CCN(c2ncnc(N)c2-c2ccc(C(C)(C)O)cc2)CC1]

The title compound was prepared in an analogous manner as Example (15) by using 2-(4-(4,4,5,5-tetramethyl-1,3,2-dioxaborolan-2-yl)phenyl)propan-2-ol instead of 4-fluorophenyl boronic acid. LC-MS: (M+1=529, obsd.=529)

Methyl 4-(4-amino-6-(4-(2-(dimethylamino)-1-(4-(trifluoromethyl)phenyl)ethyl)piperazin-1-yl)pyrimidin-5-yl)benzoate ("23")

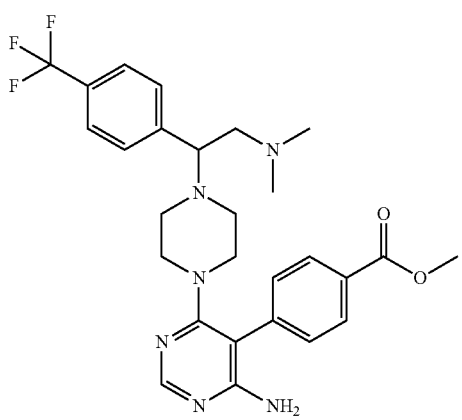 [SMILES: COC(=O)c1ccc(-c2c(N)ncnc2N2CCN(C(CN(C)C)c3ccc(C(F)(F)F)cc3)CC2)cc1]

The title compound was prepared in an analogous manner as Example (15) by using methyl 4-(4,4,5,5-tetramethyl-1,3,2-dioxaborolan-2-yl)benzoate instead of 4-fluorophenyl boronic acid. LC-MS: (M+1=529, obsd.=529)

6-(4-(2-amino-1-(4-(trifluoromethyl)phenyl)ethyl)piperazin-1-yl)-5-(cyclohex-1-en-1-yl)pyrimidin-4-amine ("24")

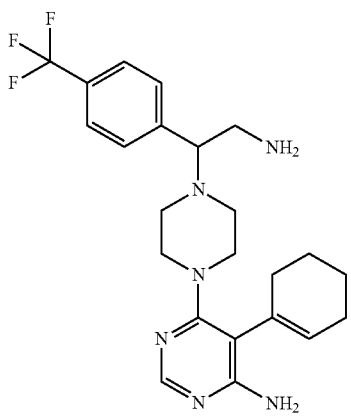 [SMILES: NCC(c1ccc(C(F)(F)F)cc1)N1CCN(c2ncnc(N)c2C2=CCCCC2)CC1]

The title compound was prepared in an analogous manner as Example (2) by using methyl 2-(cyclohex-1-en-1-yl)-4,4,5,5-tetramethyl-1,3,2-dioxaborolane instead of 4-fluorophenyl boronic acid. LC-MS: (M+1=447, obsd.=447)

6-(4-(2-amino-1-(4-(trifluoromethyl)phenyl)ethyl)piperazin-1-yl)-5-(cyclopent-1-en-1-yl)pyrimidin-4-amine ("25")

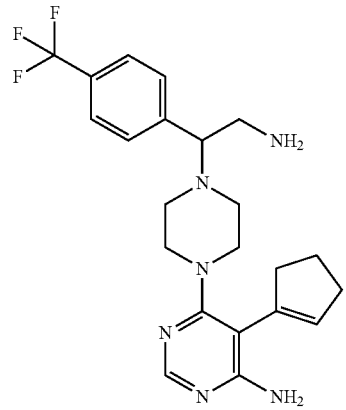 [SMILES: NCC(c1ccc(C(F)(F)F)cc1)N1CCN(c2ncnc(N)c2C2=CCCC2)CC1]

The title compound was prepared in an analogous manner as Example (2) by using 2-(cyclopent-1-en-1-yl)-4,4,5,5-tetramethyl-1,3,2-dioxaborolane instead of 4-fluorophenyl boronic acid. LC-MS: (M+1=433, obsd.=433)

49

4-(4-amino-6-(4-(2-(dimethylamino)-1-(4-(trifluoromethyl)phenyl)ethyl)piperazin-1-yl)pyrimidin-5-yl)benzoic acid ("26")

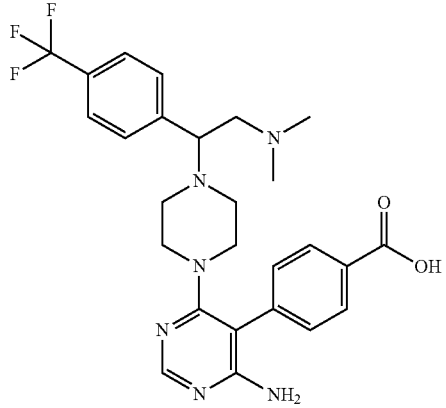 [SMILES: CN(C)CC(c1ccc(C(F)(F)F)cc1)N1CCN(c2ncnc(N)c2-c2ccc(C(=O)O)cc2)CC1]

In a round bottle flask containing 4-(4-Amino-6-{4-[2-dimethylamino-1-(4-trifluoromethyl-phenyl)-ethyl]-piperazin-1-yl}-pyrimidin-5-yl)-benzoic acid methyl ester trifluoroacetic acid (36.00 mg; 0.06 mmol; 1.00 eq.) in THF (2.00 ml) and water (2.00 ml) was added 1 N lithium hydroxide monohydrate water solution. The mixture was stirred at rt for 4 h before it was concentrated and purified with waters prep-HPLC. LC-MS: (M+1=515, obsd.=515)

6-(4-(2-(azetidin-1-yl)-1-(4-(trifluoromethyl)phenyl)ethyl)piperazin-1-yl)-5-(4-fluorophenyl)pyrimidin-4-amine ("27")

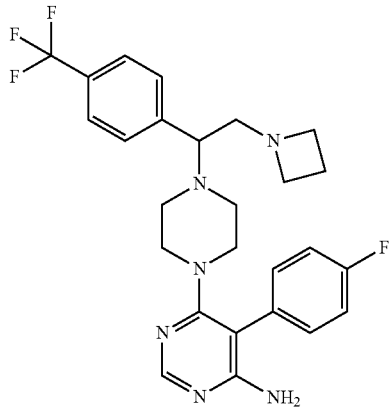 [SMILES: Nc1ncnc(N2CCN(C(CN3CCC3)c3ccc(C(F)(F)F)cc3)CC2)c1-c1ccc(F)cc1]

In a microwave vial containing 1-[2-chloro-2-(4-trifluoromethyl-phenyl)-ethyl]-azetidine (32.26 mg; 0.12 mmol; 1.00 eq.) from last step in acetonitrile (2.00 ml) was added 5-(4-fluoro-phenyl)-6-piperazin-1-yl-pyrimidin-4-ylamine (33.43 mg; 0.12 mmol; 1.00 eq.), followed by DIPEA (0.06 ml; 0.37 mmol; 3.00 eq.). The clear solution was stirred at 60° C. overnight and then 75° C. for 3 h before the mixture was concentrated and purified with waters pre-HPLC. LC-MS: (M+1=501, obsd.=501)

50

5-Cyclopropyl-6-(4-(2-(dimethylamino)-1-(4-(trifluoromethyl)phenyl)ethyl)piperazin-1-yl)pyrimidin-4-amine ("28")

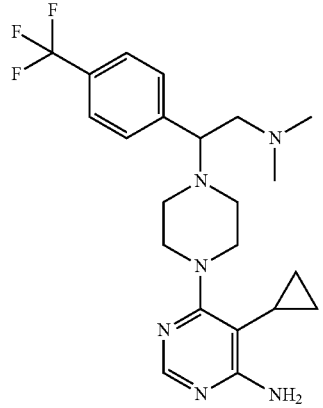 [SMILES: CN(C)CC(c1ccc(C(F)(F)F)cc1)N1CCN(c2ncnc(N)c2C2CC2)CC1]

In a microwave vial containing 5-bromo-6-{4-[2-dimethylamino-1-(4-trifluoromethyl-phenyl)-ethyl]-piperazin-1-yl}-pyrimidin-4-ylamine (84.00 mg; 0.18 mmol; 1.00 eq.) in toluene (3.00 ml; 28.23 mmol; 159.07 eq.) and water (0.30 ml; 16.65 mmol; 93.84 eq.) was added palladium(ii) acetate (3.98 mg; 0.02 mmol; 0.10 eq.), potassium cyclopropyltrifluoroborate (52.52 mg; 0.35 mmol; 2.00 eq.), cesium carbonate (127.21 mg; 0.39 mmol; 2.20 eq.) and 4,5-bis(diphenylphosphino)-9,9-dimethylxanthene (20.54 mg; 0.04 mmol; 0.20 eq.). The mixture was microwaved at 125° C. for 30 min before it was filtered the desired product was purified with Waters prep-HPLC. LC-MS: (M+1=435, obsd.=435)

5-Bromo-6-{4-[(1-methyl-1H-imidazol-2-yl)-phenyl-methyl]-piperazin-1-yl}-pyrimidin-4-ylamine ("29")

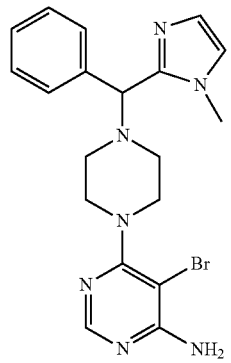 [SMILES: Cn1ccnc1C(c1ccccc1)N1CCN(c2ncnc(N)c2Br)CC1]

The title compound was prepared as a white solid in 67.7% yield in an analogous manner as Example (1) by using 1-[(1-methyl-1 h-imidazol-2-yl)-phenyl-methyl]-piperazine instead of 2-piperazin-1-yl-2-(4-trifluoromethyl-phenyl)-ethylamine. LC-MS: (M+1=429.3, obsd.=429.2).

5-(4-Fluoro-phenyl)-6-{4-[(1-methyl-1H-imidazol-2-yl)-phenyl-methyl]-piperazin-1-yl}-pyrimidin-4-ylamine ("30")

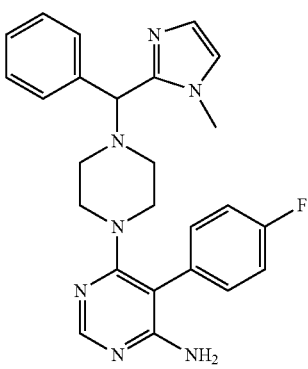 [SMILES: Cn1ccnc1C(c1ccccc1)N1CCN(c2ncnc(N)c2-c2ccc(F)cc2)CC1]

The title compound was prepared as a white solid in 79% yield in an analogous manner as Example (2). LC-MS: (M+1=443.5, obsd.=444.3).

6-(4-(2-amino-1-(4-(trifluoromethyl)phenyl)ethyl)piperazin-1-yl)-5-methoxypyrimidin-4-amine ("31")

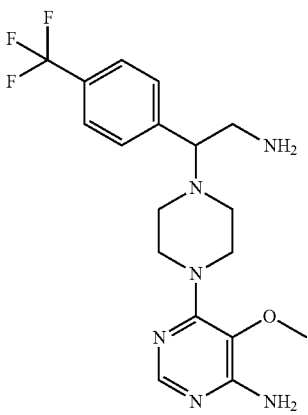 [SMILES: COc1c(N)ncnc1N1CCN(C(CN)c2ccc(C(F)(F)F)cc2)CC1]

The title compound was prepared in an analogous manner as Example (1). LC-MS (M+1=397, obsd.=397).

6-(4-(2-amino-1-(4-(trifluoromethyl)phenyl)ethyl)piperazin-1-yl)-5-ethoxypyrimidin-4-amine ("32")

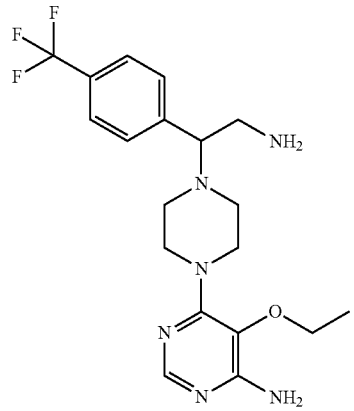 [SMILES: CCOc1c(N)ncnc1N1CCN(C(CN)c2ccc(C(F)(F)F)cc2)CC1]

The title compound was prepared in an analogous manner as Example (1). LC-MS (M+1=411, obsd.=411).

6-(4-(2-amino-1-(4-(trifluoromethyl)phenyl)ethyl)piperazin-1-yl)-5-(2,2,2-trifluoroethoxy)pyrimidin-4-amine ("33")

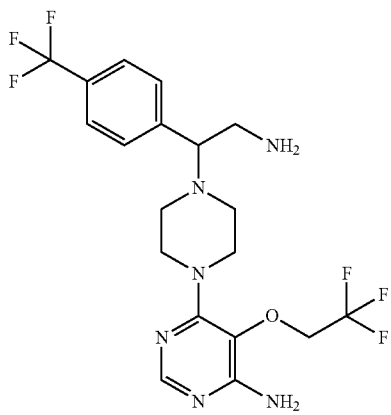 [SMILES: NCC(c1ccc(C(F)(F)F)cc1)N1CCN(c2ncnc(N)c2OCC(F)(F)F)CC1]

The title compound was prepared in an analogous manner as Example (1). LC-MS (M+1=465, obsd.=465).

6-(4-(2-amino-1-(4-(trifluoromethyl)phenyl)ethyl)
piperazin-1-yl)-5-(benzyloxy)pyrimidin-4-amine
("34")

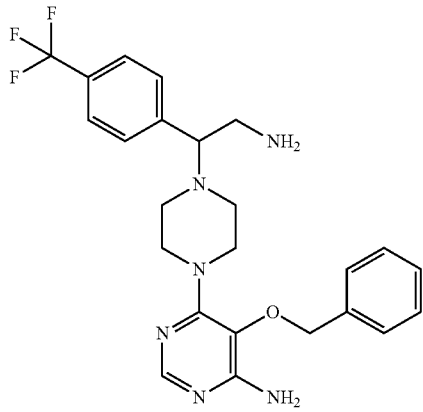 [SMILES: NCC(c1ccc(C(F)(F)F)cc1)N1CCN(c2ncnc(N)c2OCc2ccccc2)CC1]

The title compound was prepared in an analogous manner as Example (1). LC-MS (M+1=473, obsd.=473).

(35) 4-amino-6-(4-(2-amino-1-(4-(trifluoromethyl)
phenyl)ethyl)piperazin-1-yl) pyrimidin-5-ol ("35")

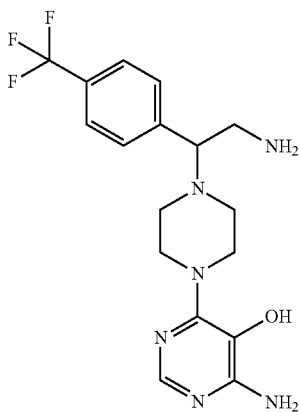

The title compound was prepared in an analogous manner as Example (1). LC-MS (M+1=483, obsd.=483).

4-Amino-6-{4-[2-amino-1-(4-trifluoromethyl-phenyl)-ethyl]-piperazin-1-yl}-pyrimidine-5-carbonitrile
("36")

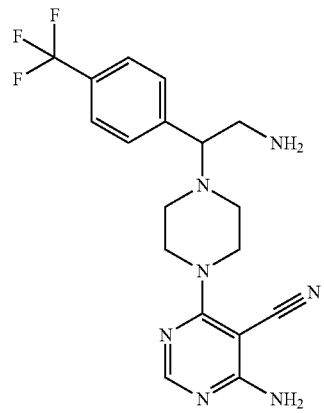 [SMILES: N#Cc1c(N)ncnc1N1CCN(C(CN)c2ccc(C(F)(F)F)cc2)CC1]

The title compound was prepared in an analogous manner as Example (1). LC-MS (M+1=392, obsd.=392).

6-(4-(2-amino-1-(4-(trifluoromethyl)phenyl)ethyl)
piperazin-1-yl)-5-(1H-pyrrol-3-yl)pyrimidin-4-amine
("37")

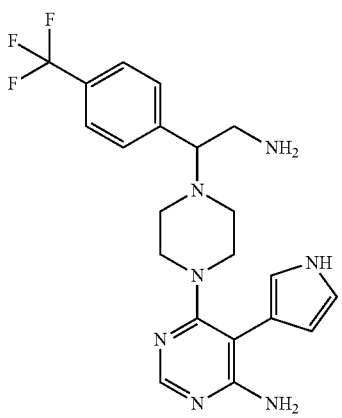 [SMILES: NCC(c1ccc(C(F)(F)F)cc1)N1CCN(c2ncnc(N)c2-c2cc[nH]c2)CC1]

The title compound was prepared in an analogous manner as Example (2). LC-MS: (M+1=432, obsd.=432).

6-(4-(2-amino-1-(4-(trifluoromethyl)phenyl)ethyl)
piperazin-1-yl)-5-(isoxazol-4-yl)pyrimidin-4-amine
("38")

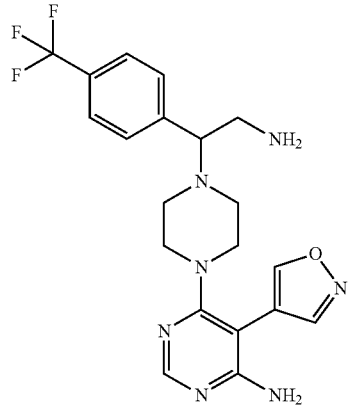 [SMILES: NCC(c1ccc(C(F)(F)F)cc1)N1CCN(c2ncnc(N)c2-c2cnoc2)CC1]

The title compound was prepared in an analogous manner as Example (2). LC-MS: (M+1=434, obsd.=434).

6-(4-(2-amino-1-(4-(trifluoromethyl)phenyl)ethyl)
piperazin-1-yl)-5-(1-ethyl-1H-pyrazol-4-yl)pyrimidin-4-amine ("39")

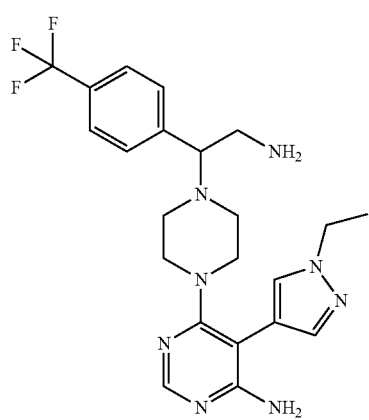 [SMILES: CCn1cc(-c2c(N)ncnc2N2CCN(C(CN)c3ccc(C(F)(F)F)cc3)CC2)cn1]

The title compound was prepared in an analogous manner as Example (2). LC-MS: (M+1=461, obsd.=461).

6-{4-[2-Amino-1-(4-trifluoromethyl-phenyl)-ethyl]-piperazin-1-yl}-5-(1-methyl-1H-pyrazol-4-yl)-pyrimidin-4-ylamine ("40")

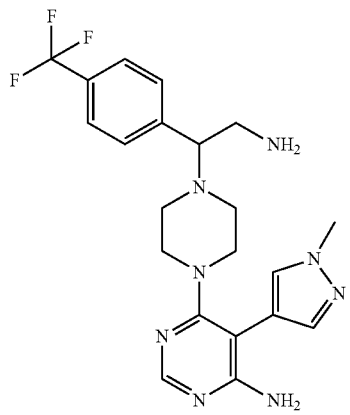 [SMILES: Cn1cc(-c2c(N)ncnc2N2CCN(C(CN)c3ccc(C(F)(F)F)cc3)CC2)cn1]

The title compound was prepared in an analogous manner as Example (2). LC-MS: (M+1=447, obsd.=447).

6-{4-[(S)-2-Amino-1-(4-trifluoromethyl-phenyl)-ethyl]-piperazin-1-yl}-5-(1-methyl-1H-pyrazol-4-yl)-pyrimidin-4-ylamine ("41")

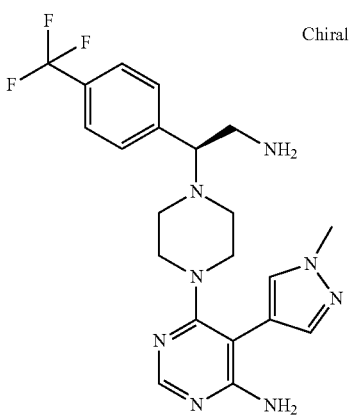 [SMILES: Cn1cc(-c2c(N)ncnc2N2CCN([C@H](CN)c3ccc(C(F)(F)F)cc3)CC2)cn1]

The title compound was isolated by the SFC chiral separation of Example (40). LC-MS: (M+1=447, obsd.=447)

6-{4-[(R)-2-Amino-1-(4-trifluoromethyl-phenyl)-ethyl]-piperazin-1-yl}-5-(1-methyl-1H-pyrazol-4-yl)-pyrimidin-4-ylamine ("42")

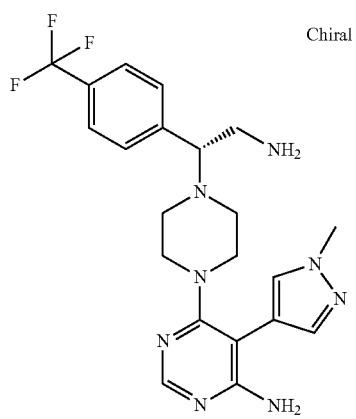 [SMILES: Cn1cc(-c2c(N)ncnc2N2CCN([C@@H](CN)c3ccc(C(F)(F)F)cc3)CC2)cn1]

The title compound was isolated by the SFC chiral separation of Example (40). LC-MS: (M+1=447, obsd.=447)

6-{4-[2-Amino-1-(4-trifluoromethyl-phenyl)-ethyl]-piperazin-1-yl}-5-(1-methyl-1H-pyrazol-3-yl)-pyrimidin-4-ylamine ("43")

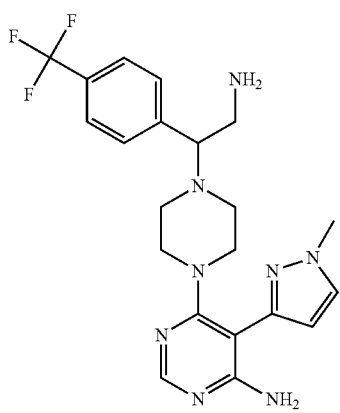 [SMILES: Cn1ccc(-c2c(N)ncnc2N2CCN(C(CN)c3ccc(C(F)(F)F)cc3)CC2)n1]

The title compound was prepared in an analogous manner as Example (2). LC-MS: (M+1=447, obsd.=447).

3-[2-{4-[6-Amino-5-(1-methyl-1H-pyrazol-3-yl)-pyrimidin-4-yl]-piperazin-1-yl}-2-(4-trifluoromethyl-phenyl)-ethylamino]-2,3-dimethyl-butan-2-ol ("44")

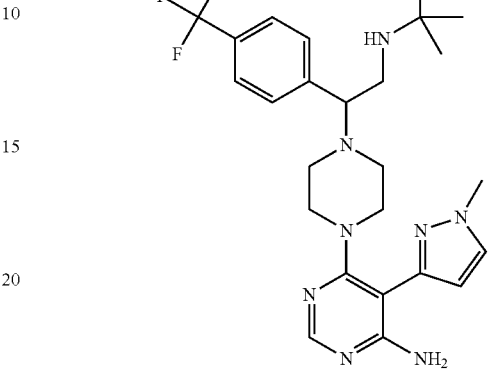

The title compound was obtained as the by-product of Example (43). LC-MS: (M+1 10=547, obsd.=547).

6-(4-(2-amino-1-(4-(trifluoromethyl)phenyl)ethyl)piperazin-1-yl)-5-((3-fluoroazetidin-1-yl)methyl)pyrimidin-4-amine ("45")

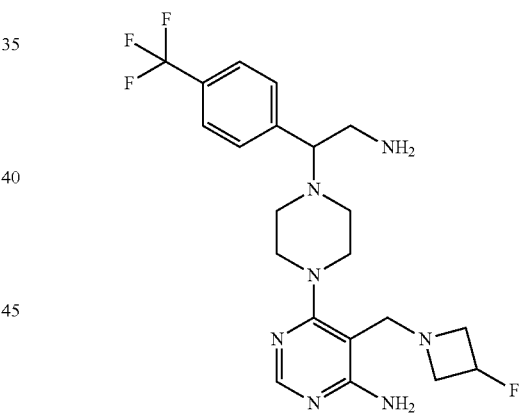

To 3-fluoro-azetidine hydrochloride (17.64 mg; 0.12 mmol; 1.05 eq.) in 1 ml of DCE was added DIEA (0.04 ml; 0.23 mmol; 2.00 eq.). After stirred at RT for 10 mins, [2-[4-(6-amino-5-formyl-pyrimidin-4-yl)-piperazin-1-yl]-2-(4-trifluoromethyl-phenyl)-ethyl]-carbamic acid benzyl ester (60.00 mg; 0.11 mmol; 1.00 eq.) was added, followed by sodium p-triacetoxyborohydride (72.18 mg; 0.34 mmol; 3.00 eq.). The reaction mixture was stirred overnight at RT. Poured the reaction solution to EA, washed with 5% sodium bicarbonate and brine. The organic layer was separated, dried and concentrated to afford the intermediate.

The above intermediate was dissolved in 1 ml of methanol, 70 mg 10% Pd/C was added and then 100 mg of ammonium formate. The resulting reaction mixture was stirred at 60° C. for 1 hr. The crude was purified by pre-HPLC to yield the title compound (10 mg, yield 15%). LC-MS: (M+1=454, obsd.=454).

5-Bromo-6{4-(4-chlorobenzyl)-piperidin-1-yl}pyrimidin-4-amine ("46")

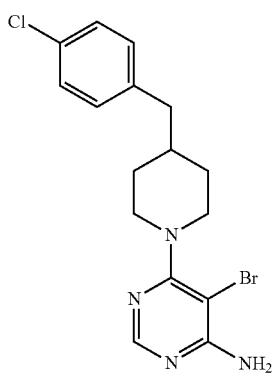 [SMILES: Nc1ncnc(N2CCC(Cc3ccc(Cl)cc3)CC2)c1Br]

The title compound was prepared in an analogous manner as Example (1). LC-MS (M+1=382, obsd=382)

5-Bromo-6{4-(4-trifluoromethylbenzyl)-piperidin-1-yl}pyrimidin-4-amine ("47")

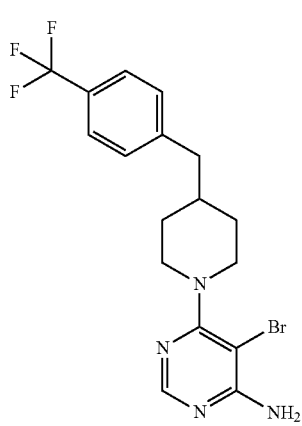 [SMILES: Nc1ncnc(N2CCC(Cc3ccc(C(F)(F)F)cc3)CC2)c1Br]

The title compound was prepared in an analogous manner as Example (1). LC-MS (M+1=416, obsd=416)

5-(4-Fluorophenyl)-6{4-(4-trifluoromethylbenzyl)-piperidin-1-yl}pyrimidin-4-amine ("48")

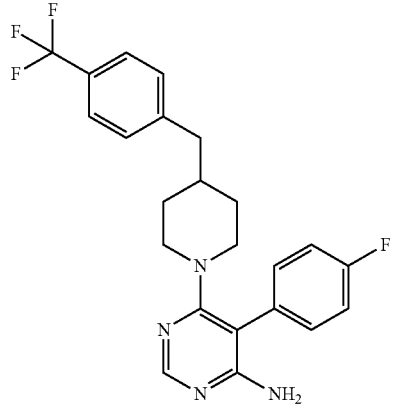 [SMILES: Nc1ncnc(N2CCC(Cc3ccc(C(F)(F)F)cc3)CC2)c1-c1ccc(F)cc1]

The title compound was prepared in an analogous manner as Example (2). LC-MS (M+1=431, obsd=431)

5-(4-Fluorophenyl)-6{4-(4-chlorobenzyl)-piperidin-1-yl}pyrimidin-4-amine ("49")

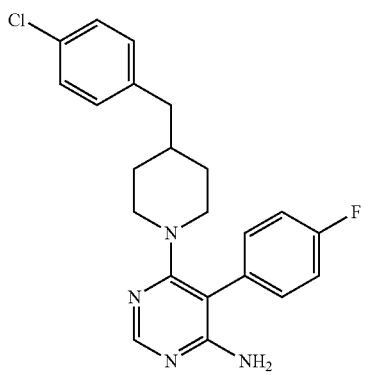 [SMILES: Nc1ncnc(N2CCC(Cc3ccc(Cl)cc3)CC2)c1-c1ccc(F)cc1]

The title compound was prepared in an analogous manner as Example (2). LC-MS (M+1=398, obsd=398)

5-(4-Fluorophenyl)-6{4-(4-(4-fluorophenyl)benzyl)-piperidin-1-yl}pyrimidin-4-amine ("50")

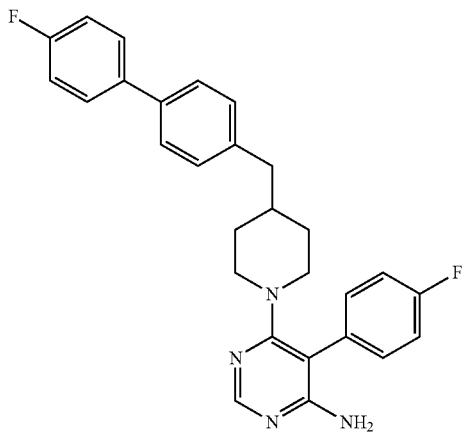 [SMILES: Nc1ncnc(N2CCC(Cc3ccc(-c4ccc(F)cc4)cc3)CC2)c1-c1ccc(F)cc1]

The title compound was prepared in an analogous manner as Example (2). LC-MS (M+1=457, obsd=457)

Examples (51) to (59) were prepared according to Synthetic Scheme 4.

6-{4-[2-Amino-1-(4-trifluoromethyl-phenyl)-ethyl]-piperidin-1-yl}-5-bromo-pyrimidin-4-ylamine ("51")

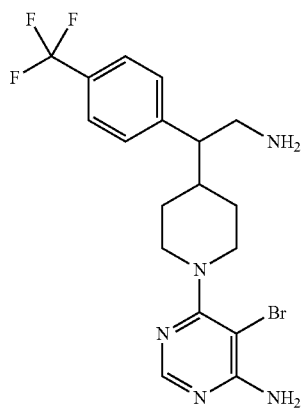 [SMILES: NCC(c1ccc(C(F)(F)F)cc1)C1CCN(c2ncnc(N)c2Br)CC1]

Intermediate (51.1) tert-butyl 4-(cyano(4-(trifluoromethyl)phenyl)methylene)piperidine-1-carboxylate To the solution of 4-(trifluoromethyl)phenylacetonitrile (2560.9 mg; 13.83 mmol; 1.06 eq.) in ethanol (50 mL), 21% sodium ethoxide (5.70 ml; 15.27 mmol; 1.17 eq.) in ethanol was added dropwise at RT. After stirred for 30 min, a solution of 1-boc-4-piperidone (2600.00 mg; 13.05 mmol; 1.00 eq.) in ethanol (10 mL) was added slowly. The reaction mixture was stirred at room temperature for 4 h. The reaction was quenched with 50 mL of saturated aqueous NH4Cl and concentrated to half volume. The aqueous solution was extracted with ether three times. The combined organic extracts were washed with brine, dried and then concentrated to give the crude product, which was purified by Biotage chromatography with EtOAc/Hexane (5-30%) to yield the desired product as light yellow solid (3200.00 mg, yield 66.9%).

Intermediate (51.2) 2-(piperidin-4-yl)-2-(4-(trifluoromethyl)phenyl)ethanamine hydrochloride salt A solution of Intermediate (51.1) (2000.0 mg; 5.46 mmol; 1.00 eq.) in 50 ml of methanol was surged on H-Qube through 20% Pd(OH)$_2$ cartridge at 1.5 ml/min and RT for one cycle. LCMS showed a clean product as tert-butyl 4-(cyano(4-(trifluoromethyl)phenyl)methyl)piperidine-1-carboxylate. 10 ml of 7.0N NH$_3$ in methanol was added to the above solution and the solution was then placed on H-Qube through Raney Ni column as cartridge at 1.5 ml/min and 45° C. for one cycle. LCMS showed clean reaction of reducing nitrile. The reaction mixture was concentrated to afford tert-butyl 4-(2-amino-1-(4-(trifluoromethyl)phenyl)ethyl)-piperidine-1-carboxylate, which was added 10 ml of 4.0M HCl in dioxane and stirred at RT for 4 hr. The precipitate was collected by filtration to yield the title compound as white solid (1600 mg, yield 77.7%). LC-MS: (M+1=273, obsd.=273).

A mixture of 5-bromo-6-chloropyrimidin-4-amine (317.78 mg; 1.45 mmol; 1.00 eq.), Intermediate (51.2) (500.00 mg; 1.45 mmol; 1.00 eq.) and potassium carbonate (600.48 mg; 4.34 mmol; 3.00 eq.) in DMSO (5.00 m) was heated at 60° C. for 14 h. The reaction mixture was purified by pre-HPLC (Waters, basic condition) to afford the title compound. LC-MS: (M+1=444, obsd.=444).

6-{4-[2-Amino-1-(4-trifluoromethyl-phenyl)-ethyl]-piperidin-1-yl}-5-(4-fluoro-phenyl)-pyrimidin-4-ylamine ("52")

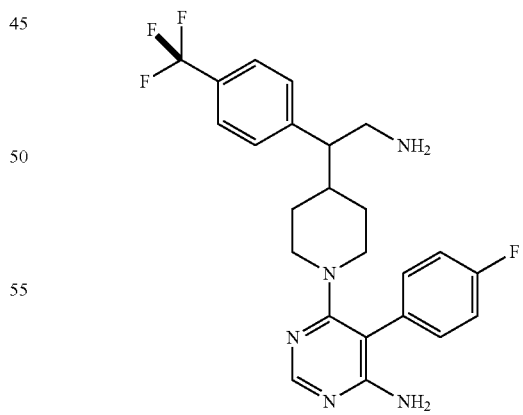

The title compound was prepared in an analogous manner as Example (2) by using of 6-{4-[2-Amino-1-(4-trifluoromethyl-phenyl)-ethyl]-piperidin-1-yl}-5-bromo-pyrimidin-4-ylamine instead of 6-{4-[2-amino-1-(4-trifluoromethyl-phenyl)-ethyl]-piperazin-1-yl}-5-bromo-pyrimidin-4-ylamine. LC-MS: (M+1=460, obsd.=460).

6-{4-[(S)-2-Amino-1-(4-trifluoromethyl-phenyl)-ethyl]-piperidin-1-yl}-5-(4-fluoro-phenyl)-pyrimidin-4-ylamine ("53")

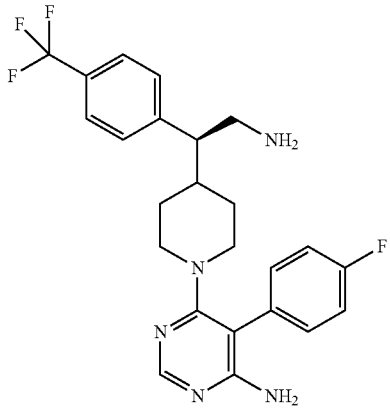 [SMILES: NC[C@H](c1ccc(C(F)(F)F)cc1)C1CCN(c2ncnc(N)c2-c2ccc(F)cc2)CC1]

The title compound was obtained via SFC chiral separation of Example (52). LC-MS: (M+1=460, obsd.=460).

6-{4-[(R)-2-Amino-1-(4-trifluoromethyl-phenyl)-ethyl]-piperidin-1-yl}-5-(4-fluoro-phenyl)-pyrimidin-4-ylamine ("54")

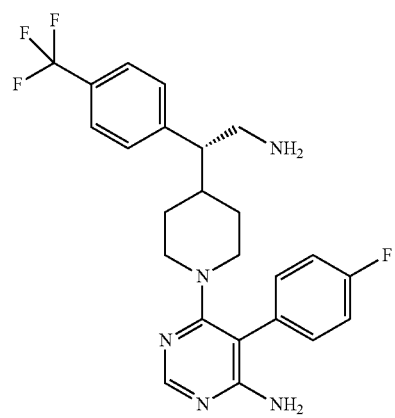 [SMILES: NC[C@@H](c1ccc(C(F)(F)F)cc1)C1CCN(c2ncnc(N)c2-c2ccc(F)cc2)CC1]

The title compound was obtained via SFC chiral separation of Example (52). LC-MS: (M+1=460, obsd.=460).

6-(4-(2-amino-1-(4-(trifluoromethyl)phenyl)ethyl)piperidin-1-yl)-5-(1H-pyrazol-4-yl)pyrimidin-4-amine ("55")

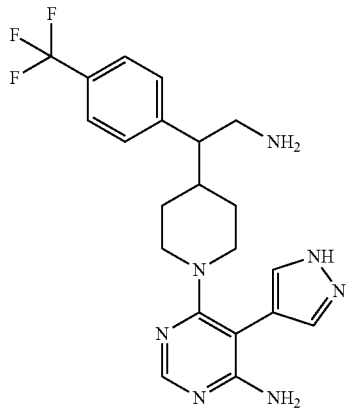 [SMILES: NCC(c1ccc(C(F)(F)F)cc1)C1CCN(c2ncnc(N)c2-c2cn[nH]c2)CC1]

Intermediate (55.1) tert-butyl (2-(1-(6-amino-5-bromopyrimidin-4-yl)piperidin-4-yl)-2-(4-(trifluoromethyl)phenyl)ethyl)carbamate A mixture of 6-(4-(2-amino-1-(4-(trifluoromethyl)phenyl)ethyl)piperidin-1-yl)-5-bromopyrimidin-4-amine (1700 mg; 3.84 mmol; 1.00 eq.) and di-tert-butyl dicarbonate (837.62 mg; 3.84 mmol; 1.00 eq.) in THF (50 ml) was stirred at RT overnight. The reaction mixture was concentrated and subjected to SNAP column (100 g), eluted with 30-80% ethyl acetate in hexan to yield the title compound (1400 mg, yield 67%). LC-MS: (M+1=544, obsd=543/544).

A mixture of Intermediate (55.1) (280.00 mg; 0.51 mmol; 1.00 eq.), 4-(4,4,5,5-Tetramethyl-[1,3,2]dioxaborolan-2-yl)-pyrazole-1-carboxylic acid tert-butyl ester (226.93 mg; 0.77 mmol; 1.50 eq.) and cesium carbonate (335 mg, 1.03 mmol, 2.0 eq.) in dioxane (3 ml) and water (0.25 ml) was degas, and then bis(tri-t-butylphosphine)palladium(0) (39.43 mg; 0.08 mmol; 0.15 eq.) added. The resulting mixture was stirred at 50° C. overnight. The reaction mixture was worked up and purified by SNAP column, eluted with 0-10% methanol in DCM to give tert-butyl 4-(4-amino-6-(4-(2-((tert-butoxycarbonyl)amino)-1-(4-(trifluoromethyl)phenyl)ethyl)piperidin-1-yl)pyrimidin-5-yl)-1H-pyrazole-1-carboxylate (280 mg, yield 86%), which was added 4 ml of methanol and 3 ml of 4.0M HCl in dioxane and stirred at RT for 3 hr. The reaction mixture was concentrated to afford the title compound in quantitative yield. LC-MS: (M+1=432, obsd.=432).

(S)-6-(4-(2-amino-1-(4-(trifluoromethyl)phenyl)ethyl)piperidin-1-yl)-5-(1H-pyrazol-4-yl)pyrimidin-4-amine ("56") (Shown in One of Enantiomer, Absolute Chirality is Unknown)

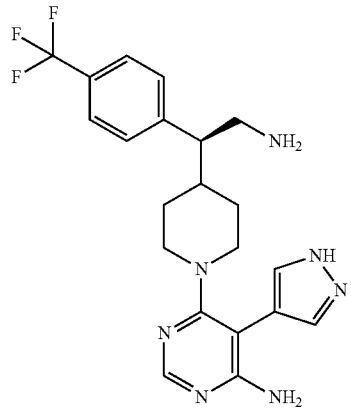 [SMILES: NC[C@H](c1ccc(C(F)(F)F)cc1)C1CCN(c2ncnc(N)c2-c2cn[nH]c2)CC1]

The title compound was obtained by chiral separation with SFC column of Example (55). LC-MS (M+1=432, obsd.=432).

(R)-6-(4-(2-amino-1-(4-(trifluoromethyl)phenyl)ethyl)piperidin-1-yl)-5-(1H-pyrazol-4-yl)pyrimidin-4-amine ("57") (Shown in One of Enantiomer, Absolute Chirality is Unknown)

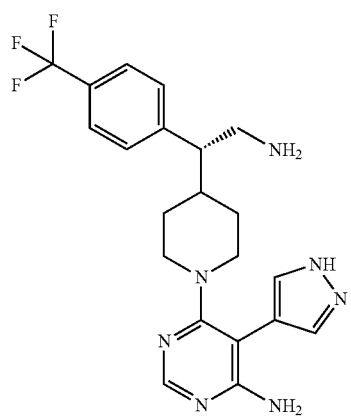 [SMILES: NC[C@@H](c1ccc(C(F)(F)F)cc1)C1CCN(c2ncnc(N)c2-c2cn[nH]c2)CC1]

The title compound was obtained by chiral separation with SFC column of Example (55). LC-MS (M+1=432, obsd.=432).

6-(4-(2-amino-1-(4-(trifluoromethyl)phenyl)ethyl)piperidin-1-yl)-5-(1-methyl-1H-pyrazol-4-yl)pyrimidin-4-amine ("58")

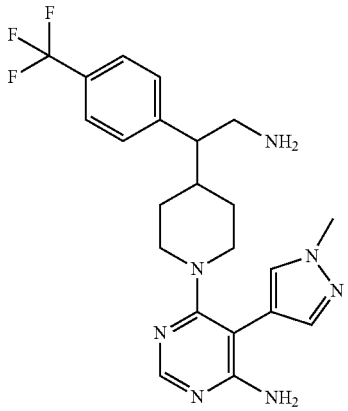 [SMILES: Cn1cc(-c2c(N)ncnc2N2CCC(C(CN)c3ccc(C(F)(F)F)cc3)CC2)cn1]

The title compound was prepared in an analogous manner as Example (55). LC-MS (M+1=446, obsd.=446).

6-(4-(2-amino-1-(4-(trifluoromethyl)phenyl)ethyl)piperidin-1-yl)-5-(isoxazol-4-yl)pyrimidin-4-amine ("59")

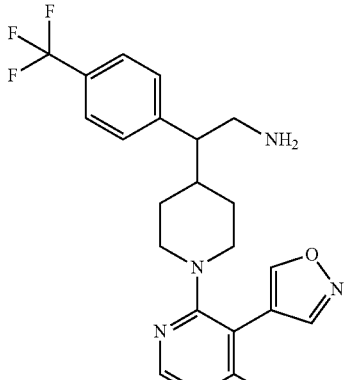

The title compound was prepared in an analogous manner as Example (55). LC-MS (M+1=433, obsd.=433).

Examples (60) to (63) were prepared according to Synthetic Scheme 5.

2-((4-(6-amino-5-(4-fluorophenyl)pyrimidin-4-yl)
piperazin-1-yl)methyl)-4,5-dichlorophenol ("60")

6-(4-(2-(azetidin-3-yloxy)-4,5-dichlorobenzyl)piper-
azin-1-yl)-5-(4-fluorophenyl)pyrimidin-4-amine
("62")

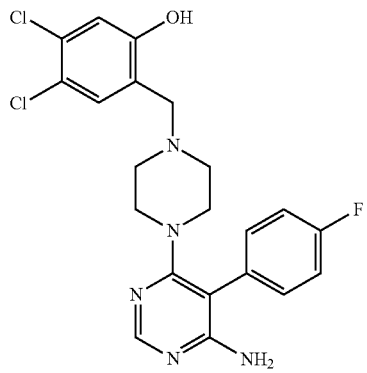 [SMILES: Nc1ncnc(N2CCN(Cc3cc(Cl)c(Cl)cc3O)CC2)c1-c1ccc(F)cc1]

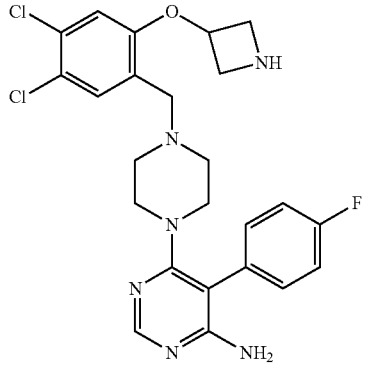

A reaction mixture of 5-(4-fluoro-phenyl)-6-piperazin-1-yl-pyrimidin-4-ylamine (400.0 mg; 1.46 mmol; 1.00 eq.), 4,5-dichloro-2-hydroxy-benzaldehyde (279.5 mg; 1.46 mmol; 1.00 eq.), Acetic acid (87.8 mg; 1.46 mmol; 1.00 eq.) and sodium triacetoxy borohydride (926.1 mg; 4.39 mmol; 3.00 eq.) in DCE (10 ml) was stirred overnight at RT. The reaction solution was diluted with DCM and washed with brine. The organic layer was dried and concentrated, which was added 10 ml of ether and stirred for mins. The precipitate was filtered to afford the title and white off solid (528 mg, yield 80.5%). LC-MS: (M+1=448, obsd.=448/450).

A reaction mixture of 2-{4-[6-amino-5-(4-fluoro-phenyl)-pyrimidin-4-yl]-piperazin-1-ylmethyl}-4,5-dichloro-phenol (80.0 mg; 0.18 mmol; 1.00 eq.), 3-iodo-azetidine-1-carboxylic acid tert-butyl ester (60.6 mg; 0.21 mmol; 1.20 eq.) and cesium carbonate (116.2 mg; 0.36 mmol; 2.00 eq.) in DMF (1 ml) was stirred at 90° C. overnight. The reaction solution was poured to water and extracted with ethyl acetate, The separated organic layer was washed with brine, dried and concentrated, which was then dissolved in methanol (1 ml) followed by adding 4.0 M HCl in dioxane (2 ml) and stirred at RT overnight. The reaction mixture was concentrated and purified by Waters prep-HPLC (acidic condition) to a yield the title compounds (37 mg, yield 33.6%). LC-MS: (M+1=504, obsd.=504/506).

6-(4-{1-[2-(Azetidin-3-yloxy)-4-chloro-phenyl]-
ethyl}-piperazin-1-yl)-5-(4-fluoro-phenyl)-pyrimi-
din-4-ylamine ("63")

2-(1-(4-(6-amino-5-(4-fluorophenyl)pyrimidin-4-yl)
piperazin-1-yl)ethyl)-5-chlorophenol ("61")

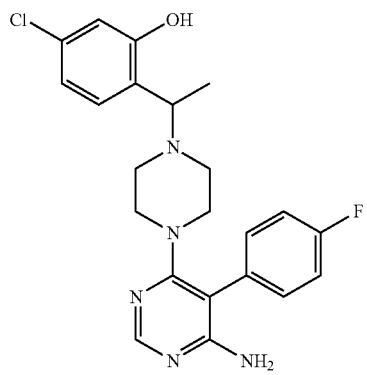 [SMILES: CC(c1ccc(Cl)cc1O)N1CCN(c2ncnc(N)c2-c2ccc(F)cc2)CC1]

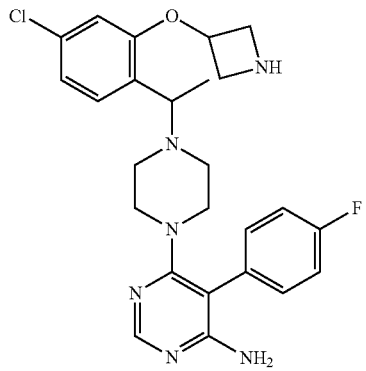 [SMILES: CC(c1ccc(Cl)cc1OC1CNC1)N1CCN(c2ncnc(N)c2-c2ccc(F)cc2)CC1]

The title compound was prepared in an analogous manner as Example (60) by 5-(4-fluorophenyl)-6-(piperazin-1-yl)pyrimidin-4-amine reacted with 1-(4-chloro-2-hydroxyphenyl)ethanone. LC-MS: (M+1=428, obsd.=428/430).

The title compound was prepared in an analogous manner as Example (62) using 2-((4-(6-amino-5-(4-fluorophenyl)pyrimidin-4-yl)piperazin-1-yl)methyl)-5-chlorophenol. LC-MS (M+1=483, obsd.=483).

Examples (64) to (137) were prepared according to Synthetic Scheme 6.

5-(4-Fluorophenyl)-6{4-[1-(3-fluoro-phenyl)-2-piperidin-1-yl-ethyl]-piperazin-1-yl}-pyrimidin-4-ylamine ("64")

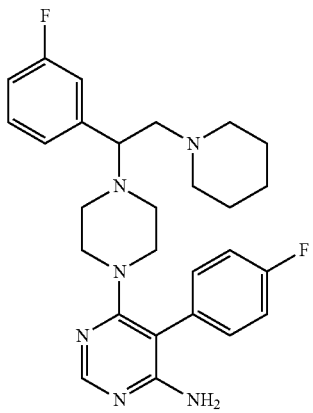 [SMILES: Nc1ncnc(N2CCN(C(CN3CCCCC3)c3cccc(F)c3)CC2)c1-c1ccc(F)cc1]

Intermediate (64.1): 1-(3-Fluoro-phenyl)-2-piperidin-1-yl-ethanone

A mixture of 2-bromo-1-(3-fluoro-phenyl)-ethanone (5.0 g; 23.04 mmol; 1.0 eq.), piperidine (2.30 ml; 23.04 mmol; 1.0 eq.) and DIEA (4.89 ml; 27.65 mmol; 1.20 eq.) in CHCl₃ (100 mL) was heated for reflux overnight. The mixture was partitioned between CHCl₃ and saturated aqueous NaHCO₃. The separated organic layer was dried over MgSO₄, filtered and concentrated. The residue was purified through flash chromatography on silica gel to afford the title compound. LC-MS: 222 (M+H).

Intermediate (64.2): 1-(3-Fluoro-phenyl)-2-piperidin-1-yl-ethanol

To a solution of 1-(3-fluoro-phenyl)-2-piperidin-1-yl-ethan Intermediate (64.1) (1.50 g; 6.78 mmol; 1.00 eq.) in MeOH (15 mL) was added sodium borohydride (0.38 g; 10.17 mmol; 1.50 eq.) and 1 mL of water and 1 drop of 10% NaOH. Then the mixture was stirred at 50° C. for 5 hours. The reaction mixture was partitioned between CHCl₃ and water. The organic layer was separated, dried over MgSO₄ and concentrated. The residue was purified through flash chromatography on silica gel to yield 1-(3-fluoro-phenyl)-2-piperidin-1-yl-ethanol. LC-MS: 224 (M+H).

Intermediate (64.3): 1-[2-Chloro-2-(3-fluoro-phenyl)-ethyl]-piperidine

To a solution of Intermediate (64.2) (2.00 g; 8.96 mmol; 1.00 eq.) in DCM (20 mL) was added thionyl chloride (3.27 ml; 44.79 mmol; 5.00 eq.) dropwise and the mixture was stirred at room temperature overnight. After removed the solvent, the solid was suspended in EtOAc and the solid was filtered and dried to yield the title compound. LC-MS: 242 (M+H).

A mixture of Intermediate (64.3) (50.00 mg; 0.21 mmol; 1.00 eq.), 5-(4-fluorophenyl)-6-piperazin-1-yl-pyrimidin-4-ylamine (80.12 mg; 0.21 mmol; 1.00 eq.) and DIEA (0.18 ml; 1.03 mmol; 5.00 eq.) in acetonitrile (5 mL) was stirred at 70° C. overnight. The mixture was purified through reverse phase HPLC to provide the title compound. LC-MS: (M+1=479, obsd.=479).

5-(4-Fluorophenyl)-6{4-[1-(3-trifluoro-phenyl)-2-piperidin-1-yl-ethyl]-piperazin-1-yl}-pyrimidin-4-ylamine ("65")

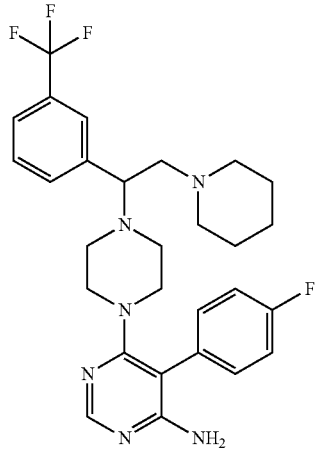 [SMILES: Nc1ncnc(N2CCN(C(CN3CCCCC3)c3cccc(C(F)(F)F)c3)CC2)c1-c1ccc(F)cc1]

The title compound was prepared in an analogous manner as Example (64). LC-MS: (M+1=529, obsd.=529).

5-(4-Fluorophenyl)-6{4-[1-(3-trifluoromethyl-phenyl)-2-pyrrolidin-1-yl-ethyl]-piperazin-1-yl}-pyrimidin-4-ylamine ("66")

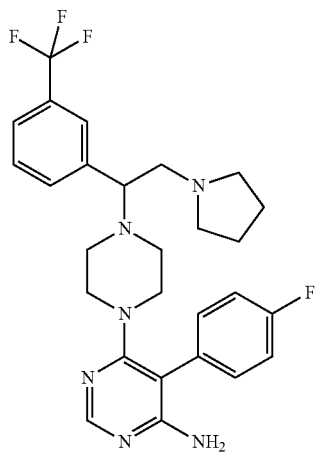 [SMILES: Nc1ncnc(N2CCN(C(CN3CCCC3)c3cccc(C(F)(F)F)c3)CC2)c1-c1ccc(F)cc1]

The title compound was prepared in an analogous manner as Example (64). LC-MS: (M+1=514, obsd.=514).

71

5-(4-Fluorophenyl)-6{4-[1-(4-fluoro-phenyl)-2-piperidin-1-yl-ethyl]-piperazin-1-yl}-pyrimidin-4-ylamine ("67")

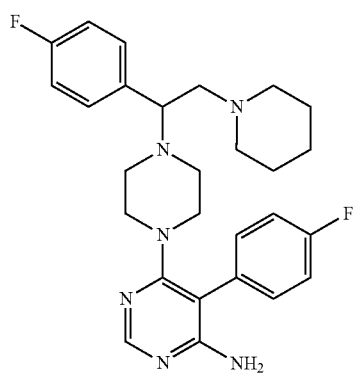 [SMILES: Nc1ncnc(N2CCN(C(CN3CCCCC3)c3ccc(F)cc3)CC2)c1-c1ccc(F)cc1]

The title compound was prepared in an analogous manner as Example (64). LC-MS: (M+1=479, obsd.=479).

5-Bromo-6{4-[1-(3-fluoro-phenyl)-2-piperidin-1-yl-ethyl]-piperazin-1-yl}-pyrimidin-4-ylamine ("68")

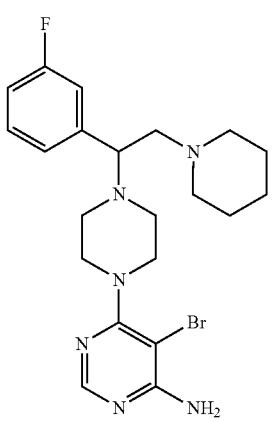 [SMILES: Nc1ncnc(N2CCN(C(CN3CCCCC3)c3cccc(F)c3)CC2)c1Br]

The title compound was prepared in an analogous manner as Example (64). LC-MS (M+1=463, obsd=463)

72

5-Bromo-6{4-[1-(3-trifluoromethyl-phenyl)-2-pyrrolidin-1-yl-ethyl]-piperazin-1-yl}-pyrimidin-4-ylamine ("69")

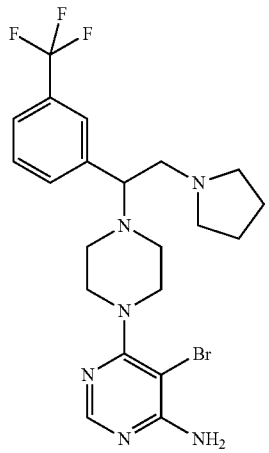 [SMILES: Nc1ncnc(N2CCN(C(CN3CCCC3)c3cccc(C(F)(F)F)c3)CC2)c1Br]

The title compound was prepared in an analogous manner as Example (64). LC-MS (M+1=499, obsd=499)

5-Bromo-6{4-[1-(3-trifluoromethyl-phenyl)-2-piperidin-1-yl-ethyl]-piperazin-1-yl}-pyrimidin-4-ylamine ("70")

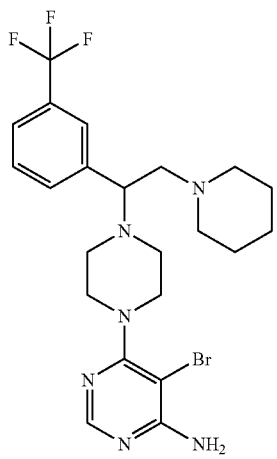 [SMILES: Nc1ncnc(N2CCN(C(CN3CCCCC3)c3cccc(C(F)(F)F)c3)CC2)c1Br]

The title compound was prepared in an analogous manner as Example (64). LC-MS (M+1=513, obsd=513)

73

6-{4-[1-(3-trifluoromethyl-phenyl)-2-piperidin-1-yl-ethyl]-piperazin-1-yl}-pyrimidin-4-ylamine ("71")

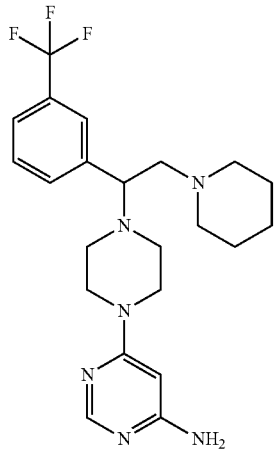 [SMILES: Nc1cc(N2CCN(C(CN3CCCCC3)c3cccc(C(F)(F)F)c3)CC2)ncn1]

The title compound was prepared in an analogous manner as Example (64). LC-MS (M+1=435, obsd=435)

5-Bromo-6{4-[1-(4-fluoro-phenyl)-2-piperidin-1-yl-ethyl]-piperazin-1-yl}-pyrimidin-4-ylamine ("72")

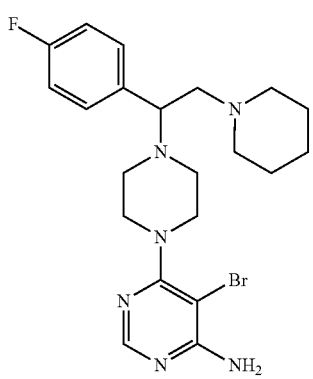 [SMILES: Nc1ncnc(N2CCN(C(CN3CCCCC3)c3ccc(F)cc3)CC2)c1Br]

The title compound was prepared in an analogous manner as Example (64). LC-MS (M+1=463, obsd=463)

74

6-{4-[1-(3-trifluoromethyl-phenyl)-2-pyrrolidin-1-yl-ethyl]-piperazin-1-yl}-pyrimidin-4-ylamine ("73")

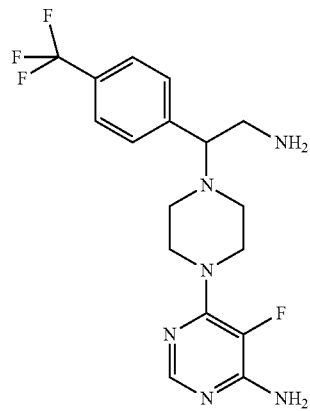 [SMILES: NCC(c1ccc(C(F)(F)F)cc1)N1CCN(c2ncnc(N)c2F)CC1]

The title compound was prepared in an analogous manner as Example (64). LC-MS (M+1=421, obsd=421)

6-{4-[2-Amino-1-(4-trifluoromethyl-phenyl)-ethyl]-piperazin-1-yl}-5-fluoro-pyrimidin-4-ylamine ("74")

The title compound was prepared in an analogous manner as Example (64). LC-MS (M+1=385, obsd=385)

75

5-(4-Fluorophenyl)-6{4-[1-(4-fluorophenyl)-2-pyrrolidin-1-yl-ethyl]-piperazin-1-yl}-pyrimidin-4-ylamine ("75")

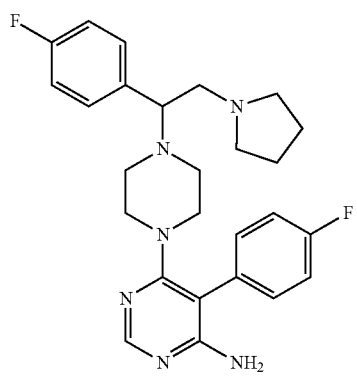 [SMILES: Nc1ncnc(N2CCN(C(CN3CCCC3)c3ccc(F)cc3)CC2)c1-c1ccc(F)cc1]

The title compound was prepared in an analogous manner as Example (64). LC-MS (M+1=465, obsd=465)

6-{4-[1-(3-fluorophenyl)-2-piperidin-1-yl-ethyl]-piperazin-1-yl}-pyrimidin-4-ylamine ("76")

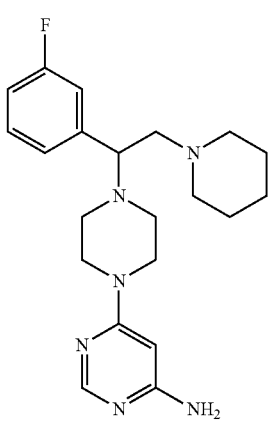 [SMILES: Nc1cc(N2CCN(C(CN3CCCCC3)c3cccc(F)c3)CC2)ncn1]

The title compound was prepared in an analogous manner as Example (64). LC-MS (M+1=385, obsd=385)

76

5-Bromo-6{4-[1-(4-fluorophenyl)-2-pyrrolidin-1-yl-ethyl]-piperazin-1-yl}-pyrimidin-4-ylamine ("77")

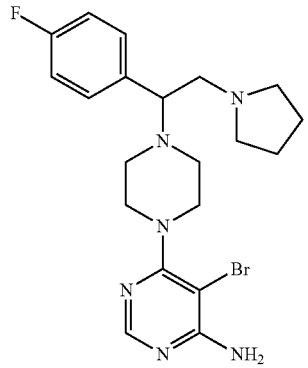

The title compound was prepared in an analogous manner as Example (64). LC-MS (M+1=449, obsd=449)

6-{4-[1-(4-fluorophenyl)-2-pyrrolidin-1-yl-ethyl]-piperazin-1-yl}-pyrimidin-4-ylamine "78")

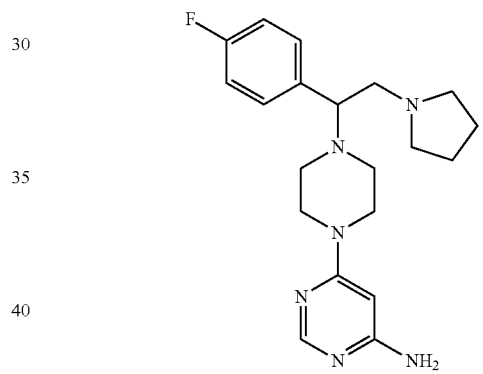

The title compound was prepared in an analogous manner as Example (64). LC-MS (M+1=371, obsd=371)

6-{4-[1-(4-fluoro-phenyl)-2-piperidin-1-yl-ethyl]-piperazin-1-yl}-pyrimidin-4-ylamine ("79")

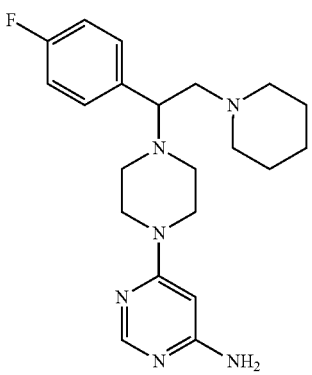 [SMILES: Nc1cc(N2CCN(C(CN3CCCCC3)c3ccc(F)cc3)CC2)ncn1]

The title compound was prepared in an analogous manner as Example (64). LC-MS (M+1=485, obsd=485)

6-{4-[2-Amino-1-(4-trifluoromethyl-phenyl)-ethyl]-piperazin-1-yl}-5-chloro-pyrimidin-4-ylamine ("80")

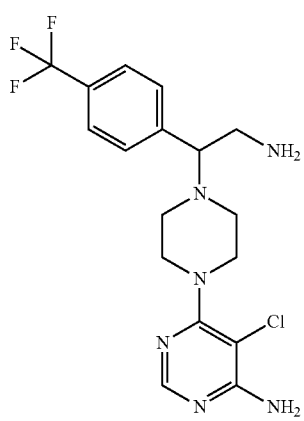 [SMILES: NCC(c1ccc(C(F)(F)F)cc1)N1CCN(c2ncnc(N)c2Cl)CC1]

The title compound was prepared in an analogous manner as Example (64). LC-MS (M+1=401, obsd=401)

5-Chloro-6{4-[1-(4-fluorophenyl)-2-pyrrolidin-1-yl-ethyl]-piperazin-1-yl}-pyrimidin-4-ylamine ("81")

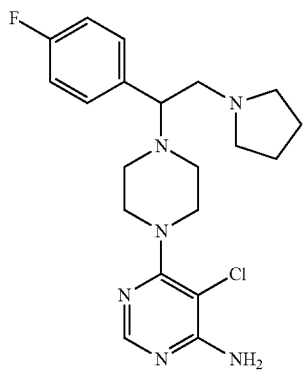 [SMILES: Nc1ncnc(N2CCN(C(CN3CCCC3)c3ccc(F)cc3)CC2)c1Cl]

The title compound was prepared in an analogous manner as Example (64). LC-MS (M+1=405, obsd=405)

(R)5-(4-Fluorophenyl)-6{4-[1-(4-fluorophenyl)-2-pyrrolidin-1-yl-ethyl]-piperazin-1-yl}-pyrimidin-4-ylamine ("82")

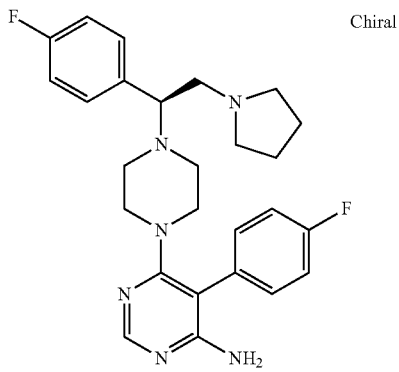 [SMILES: Nc1ncnc(N2CCN([C@H](CN3CCCC3)c3ccc(F)cc3)CC2)c1-c1ccc(F)cc1]

The title compound was prepared in a chiral separation of Example (75). LC-MS (M+1=465, obsd=465)

(S)-5-(4-Fluorophenyl)-6{4-[1-(4-fluorophenyl)-2-pyrrolidin-1-yl-ethyl]-piperazin-1-yl}-pyrimidin-4-ylamine ("83")

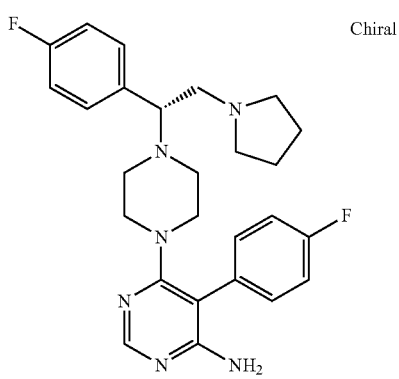 [SMILES: Nc1ncnc(N2CCN([C@@H](CN3CCCC3)c3ccc(F)cc3)CC2)c1-c1ccc(F)cc1]

The title compound was prepared in a chiral separation of Example (75). LC-MS (M+1=465, obsd=465)

6-{4-[2-Azetidin-1-yl-1-(3-fluoro-phenyl)-ethyl]-piperazin-1-yl}-5-(1H-pyrazol-4-yl)-pyrimidin-4-ylamine ("84")

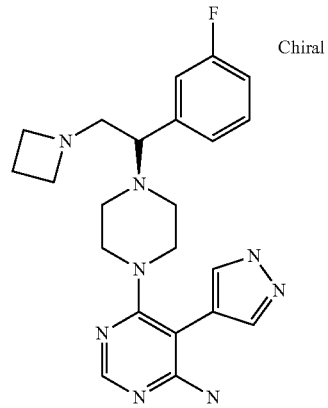

The title compound was prepared in an analogous manner as Example (64) then isolated by the SFC chiral separation Example (3). LC-MS: (M+1=423, obsd.=423)

4-(1-{4-[6-Amino-5-(1H-pyrazol-4-yl)-pyrimidin-4-yl]-piperazin-1-yl}-2-azetidin-1-yl-ethyl)-benzonitrile ("85")

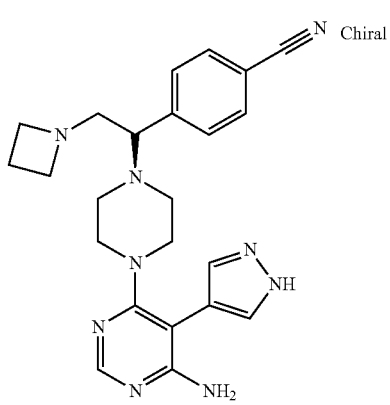

The title compound was prepared in an analogous manner as Example (64) then isolated by the SFC chiral separation. LC-MS: (M+1=430, obsd.=430)

4-(1-{4-[6-Amino-5-(1H-pyrazol-4-yl)-pyrimidin-4-yl]-piperazin-1-yl}-2-azetidin-1-yl-ethyl)-benzoic acid methyl ester ("86")

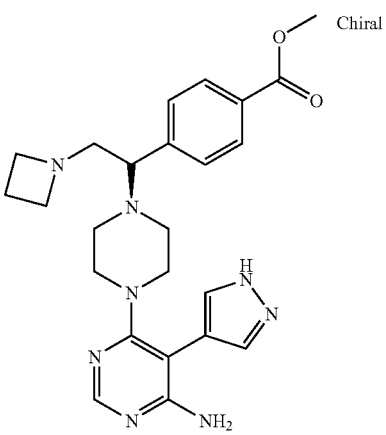

The title compound was prepared in an analogous manner as Example (64) then isolated by the SFC chiral separation. LC-MS: (M+1=463, obsd.=463)

6-{4-[(S)-2-Azetidin-1-yl-1-(3-fluoro-phenyl)-ethyl]-piperazin-1-yl}-5-(1H-pyrazol-4-yl)-pyrimidin-4-ylamine ("87")

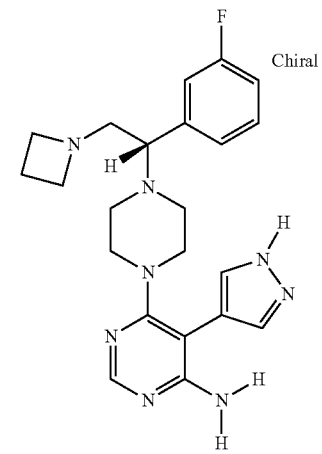 [SMILES: Nc1ncnc(N2CCN([C@H](CN3CCC3)c3cccc(F)c3)CC2)c1-c1cn[nH]c1]

The title compound was prepared in an analogous manner as Example (64) then isolated by the SFC chiral separation. LC-MS: (M+1=423, obsd.=423)

81

4-((S)-1-{4-[6-Amino-5-(1H-pyrazol-4-yl)-pyrimidin-4-yl]-piperazin-1-yl}-2-azetidin-1-yl-ethyl)-benzonitrile ("88")

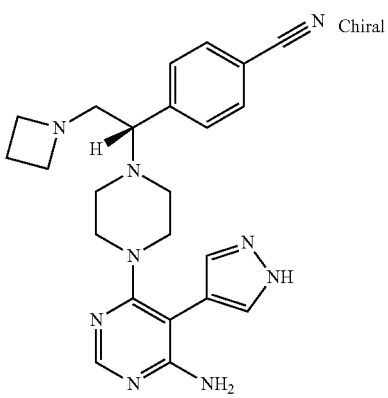 [SMILES: N#Cc1ccc([C@@H](CN2CCC2)N2CCN(c3ncnc(N)c3-c3cn[nH]c3)CC2)cc1]

The title compound was prepared in an analogous manner as Example (64) then isolated by the SFC chiral separation. LC-MS: (M+1=430, obsd.=430)

4-((S)-1-{4-[6-Amino-5-(1H-pyrazol-4-yl)-pyrimidin-4-yl]-piperazin-1-yl}-2-azetidin-1-yl-ethyl)-benzoic acid methyl ester ("89")

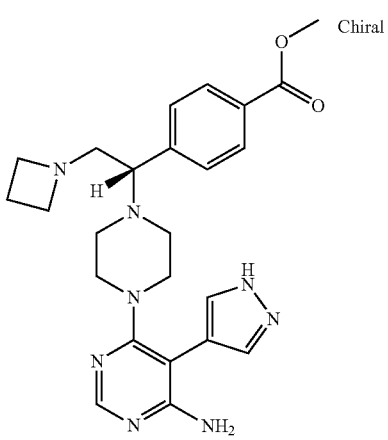 [SMILES: COC(=O)c1ccc([C@@H](CN2CCC2)N2CCN(c3ncnc(N)c3-c3cn[nH]c3)CC2)cc1]

The title compound was prepared in an analogous manner as Example (64) then isolated by the SFC chiral separation. LC-MS: (M+1=463, obsd.=463)

82

6-{4-[2-Azetidin-1-yl-1-(3-fluoro-phenyl)-ethyl]-piperazin-1-yl}-5-(4-fluoro-phenyl)-pyrimidin-4-ylamine ("90")

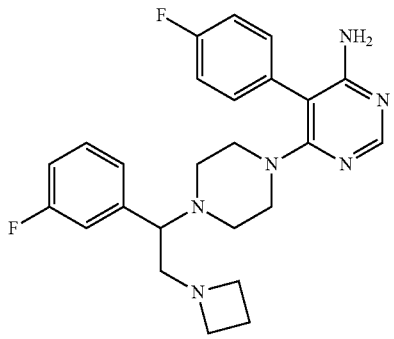 [SMILES: Nc1ncnc(N2CCN(C(CN3CCC3)c3cccc(F)c3)CC2)c1-c1ccc(F)cc1]

The title compound was prepared in an analogous manner as Example (64). LC-MS: (M+1=451, obsd.=451)

3-((R)-1-{4-[6-Amino-5-(1H-pyrazol-4-yl)-pyrimidin-4-yl]-piperazin-1-yl}-2-azetidin-1-yl-ethyl)-benzonitrile ("91")

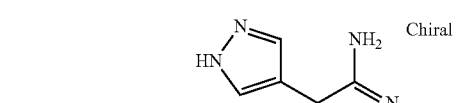

The title compound was prepared in an analogous manner as Example (64) then isolated by the SFC chiral separation. LC-MS: (M+1=430, obsd.=430)

6-{4-[2-Azetidin-1-yl-1-(3-fluoro-4-methoxy-phenyl)-ethyl]-piperazin-1-yl}-5-(4-fluoro-phenyl)-pyrimidin-4-ylamine ("92")

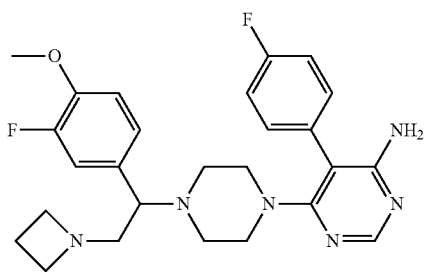 [SMILES: COc1ccc(C(CN2CCC2)N2CCN(c3ncnc(N)c3-c3ccc(F)cc3)CC2)cc1F]

The title compound was prepared in an analogous manner as Example (64). LC-MS: (M+1=481, obsd.=481)

6-{4-[(R)-2-Azetidin-1-yl-1-(4-methanesulfonyl-phenyl)-ethyl]-piperazin-1-yl}-5-(1H-pyrazol-4-yl)-pyrimidin-4-ylamine ("93")

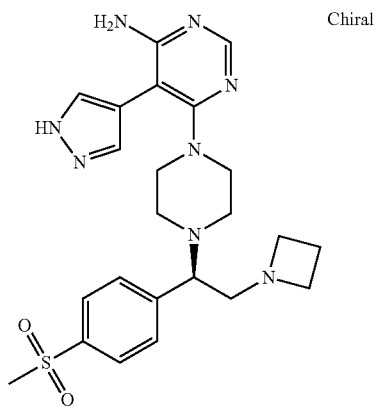 [SMILES: CS(=O)(=O)c1ccc([C@H](CN2CCC2)N2CCN(c3ncnc(N)c3-c3cn[nH]c3)CC2)cc1]

The title compound was prepared in an analogous manner as Example (64) then isolated by the SFC chiral separation. LC-MS: (M+1=483, obsd.=483)

6-{4-[(R)-2-Azetidin-1-yl-1-(2,3-dihydro-benzo[1,4]dioxin-6-yl)-ethyl]-piperazin-1-yl}-5-(4-fluoro-phenyl)-pyrimidin-4-ylamine ("94")

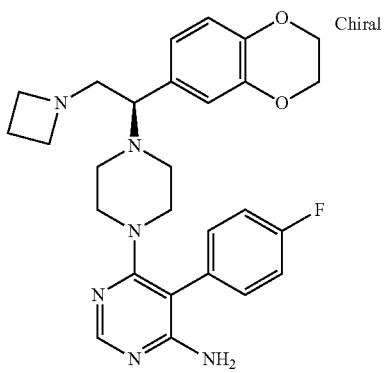 [SMILES: Nc1ncnc(N2CCN([C@@H](CN3CCC3)c3ccc4c(c3)OCCO4)CC2)c1-c1ccc(F)cc1]

The title compound was prepared in an analogous manner as Example (64) then isolated by the SFC chiral separation. LC-MS: (M+1=491, obsd.=491)

6-{4-[2-Azetidin-1-yl-1-(3-fluoro-4-methoxy-phenyl)-ethyl]-piperazin-1-yl}-5-(1H-pyrazol-4-yl)-pyrimidin-4-ylamine ("95")

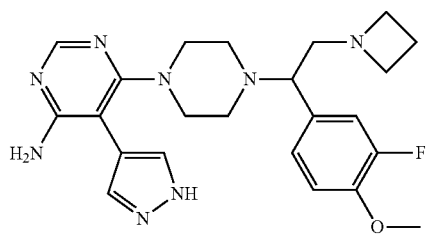 [SMILES: COc1ccc(C(CN2CCC2)N2CCN(c3ncnc(N)c3-c3cn[nH]c3)CC2)cc1F]

The title compound was prepared in an analogous manner as Example (64). LC-MS: (M+1=453, obsd.=453)

4-(1-{4-[6-Amino-5-(4-fluoro-phenyl)-pyrimidin-4-yl]-piperazin-1-yl}-2-azetidin-1-yl-ethyl)-benzoic acid methyl ester ("96")

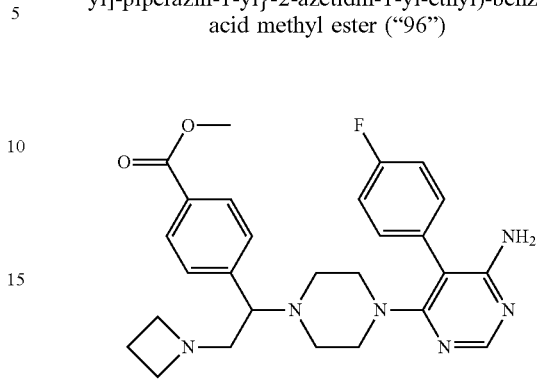

The title compound was prepared in an analogous manner as Example (64). LC-MS: (M+1=491, obsd.=491)

3-((S)-1-{4-[6-Amino-5-(1H-pyrazol-4-yl)-pyrimidin-4-yl]-piperazin-1-yl}-2-azetidin-1-yl-ethyl)-benzonitrile ("97")

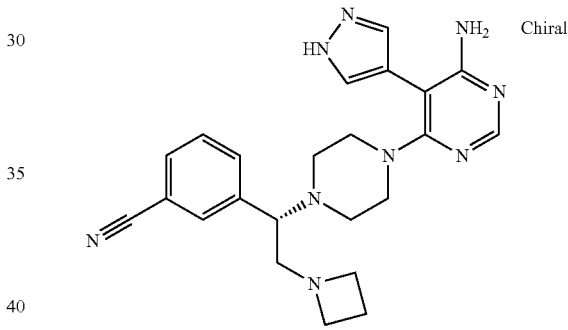

The title compound was prepared in an analogous manner as Example (64) then isolated by the SFC chiral separation. LC-MS: (M+1=430, obsd.=430)

6-{4-[(S)-2-Azetidin-1-yl-1-(2,3-dihydro-benzo[1,4]dioxin-6-yl)-ethyl]-piperazin-1-yl}-5-(4-fluoro-phenyl)-pyrimidin-4-ylamine ("98")

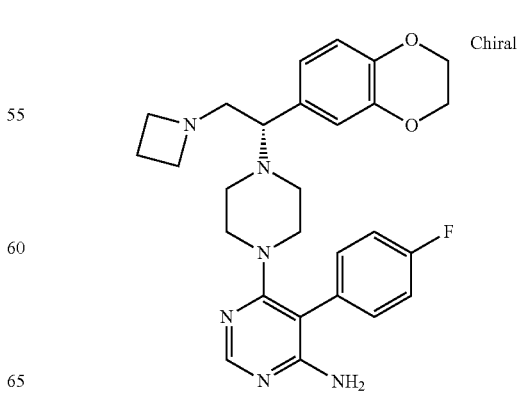

The title compound was prepared in an analogous manner as Example (64) then isolated by the SFC chiral separation. LC-MS: (M+1=491, obsd.=491)

6-{4-[2-Azetidin-1-yl-1-(2-fluoro-3-trifluoromethyl-phenyl)-ethyl]-piperazin-1-yl}-5-(1H-pyrazol-4-yl)-pyrimidin-4-ylamine ("99")

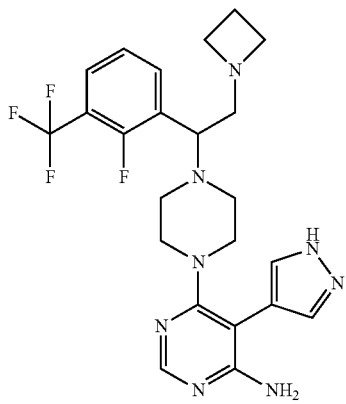 [SMILES: Nc1ncnc(N2CCN(C(CN3CCC3)c3cccc(C(F)(F)F)c3F)CC2)c1-c1cn[nH]c1]

The title compound was prepared in an analogous manner as Example (64). LC-MS: (M+1=491, obsd.=491)

6-{4-[2-Azetidin-1-yl-1-(2,3-difluoro-4-methyl-phenyl)-ethyl]-piperazin-1-yl}-5-(1H-pyrazol-4-yl)-pyrimidin-4-ylamine ("100")

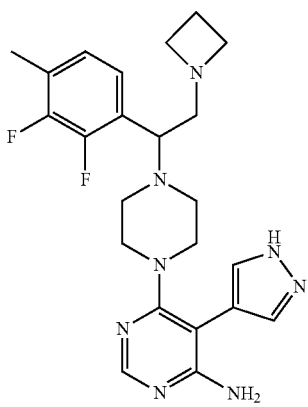 [SMILES: Cc1ccc(C(CN2CCC2)N2CCN(c3ncnc(N)c3-c3cn[nH]c3)CC2)c(F)c1F]

The title compound was prepared in an analogous manner as Example (64). LC-MS: (M+1=430, obsd.=430)

6-{4-[2-Azetidin-1-yl-1-(4-fluoro-3-trifluoromethyl-phenyl)-ethyl]-piperazin-1-yl}-5-(1H-pyrazol-4-yl)-pyrimidin-4-ylamine ("101")

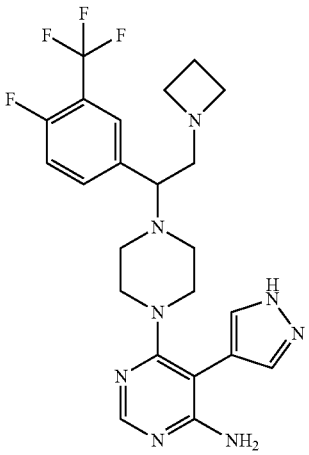 [SMILES: Nc1ncnc(N2CCN(C(CN3CCC3)c3ccc(F)c(C(F)(F)F)c3)CC2)c1-c1cn[nH]c1]

The title compound was prepared in an analogous manner as Example (64). LC-MS: (M+1=491, obsd.=491)

6-{4-[(S)-2-Azetidin-1-yl-1-(3-fluoro-phenyl)-ethyl]-piperazin-1-yl}-5-(4-fluoro-phenyl)-pyrimidin-4-ylamine ("102")

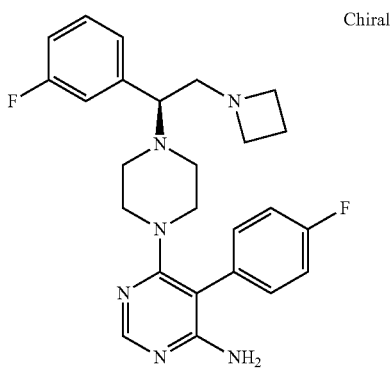 [SMILES: Nc1ncnc(N2CCN([C@H](CN3CCC3)c3cccc(F)c3)CC2)c1-c1ccc(F)cc1]

The title compound was prepared in an analogous manner as Example (64) then isolated by the SFC chiral separation. LC-MS: (M+1=451, obsd.=451)

87

6-{4-[(R)-2-Azetidin-1-yl-1-(3-fluoro-phenyl)-ethyl]-piperazin-1-yl}-5-(4-fluoro-phenyl)-pyrimidin-4-ylamine ("103")

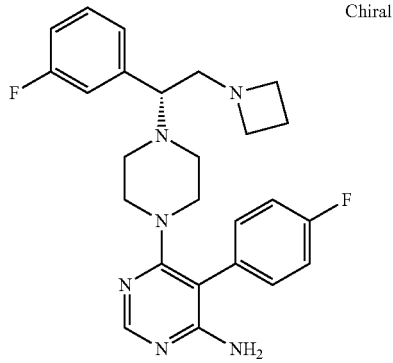 [SMILES: Nc1ncnc(N2CCN([C@@H](CN3CCC3)c3cccc(F)c3)CC2)c1-c1ccc(F)cc1]

The title compound was prepared in an analogous manner as Example (64) then isolated by the SFC chiral separation. LC-MS: (M+1=451, obsd.=451)

6-{4-[(R)-2-Azetidin-1-yl-1-(3-fluoro-4-methoxy-phenyl)-ethyl]-piperazin-1-yl}-5-(4-fluoro-phenyl)-pyrimidin-4-ylamine ("104")

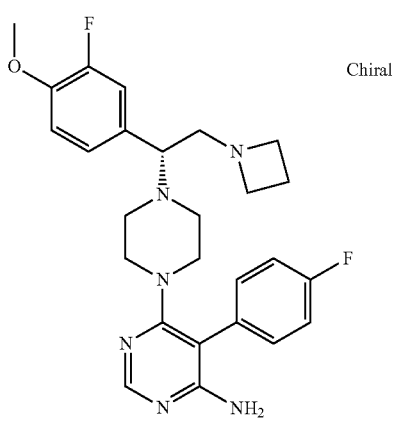 [SMILES: COc1ccc([C@H](CN2CCC2)N2CCN(c3ncnc(N)c3-c3ccc(F)cc3)CC2)cc1F]

The title compound was prepared in an analogous manner as Example (64) then isolated by the SFC chiral separation. LC-MS: (M+1=481, obsd.=481)

88

6-{4-[(S)-2-Azetidin-1-yl-1-(3-fluoro-4-methoxy-phenyl)-ethyl]-piperazin-1-yl}-5-(4-fluoro-phenyl)-pyrimidin-4-ylamine ("105")

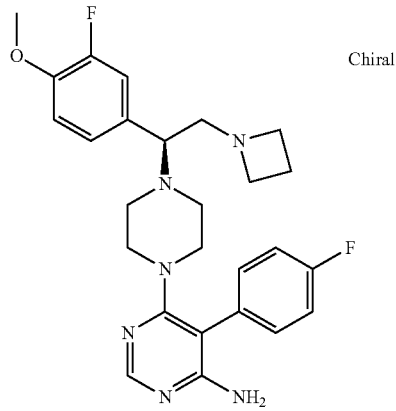 [SMILES: COc1ccc([C@@H](CN2CCC2)N2CCN(c3ncnc(N)c3-c3ccc(F)cc3)CC2)cc1F]

The title compound was prepared in an analogous manner as Example (64) then isolated by the SFC chiral separation. LC-MS: (M+1=481, obsd.=481)

4-(1-{4-[6-Amino-5-(4-fluoro-phenyl)-pyrimidin-4-yl]-piperazin-1-yl}-2-azetidin-1-yl-ethyl)-benzonitrile ("106")

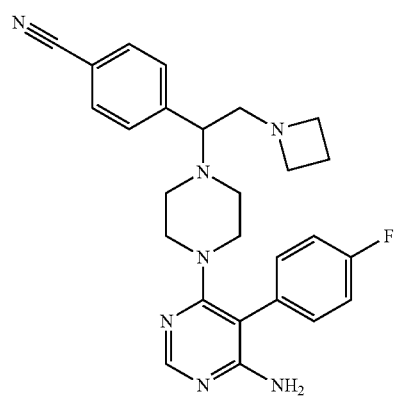 [SMILES: N#Cc1ccc(C(CN2CCC2)N2CCN(c3ncnc(N)c3-c3ccc(F)cc3)CC2)cc1]

The title compound was prepared in an analogous manner as Example (64). LC-MS: (M+1=458, obsd.=458)

6-{4-[(R)-2-Azetidin-1-yl-1-(2,3-dihydro-benzo[1,4]dioxin-6-yl)-ethyl]-piperazin-1-yl}-5-(1H-pyrazol-4-yl)-pyrimidin-4-ylamine ("107")

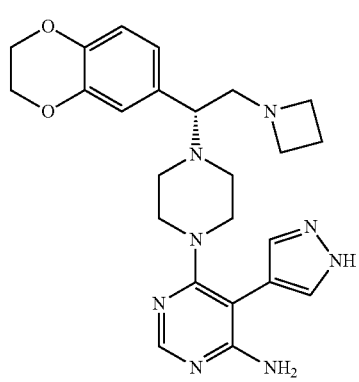

The title compound was prepared in an analogous manner as Example (64) then isolated by the SFC chiral separation. LC-MS: (M+1=463, obsd.=463)

6-{4-[(S)-2-Azetidin-1-yl-1-(2,3-dihydro-benzo[1,4]dioxin-6-yl)-ethyl]-piperazin-1-yl}-5-(1H-pyrazol-4-yl)-pyrimidin-4-ylamine ("108")

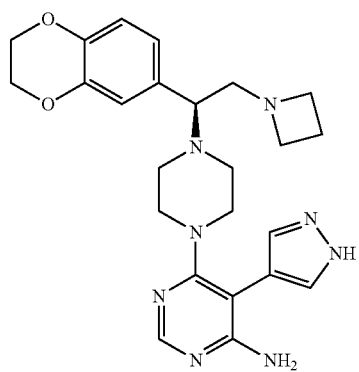

The title compound was prepared in an analogous manner as Example (64) then isolated by the SFC chiral separation. LC-MS: (M+1=463, obsd.=463)

6-{4-[2-Azetidin-1-yl-1-(4-chloro-3-methyl-phenyl)-ethyl]-piperazin-1-yl}-5-(1H-pyrazol-4-yl)-pyrimidin-4-ylamine ("109")

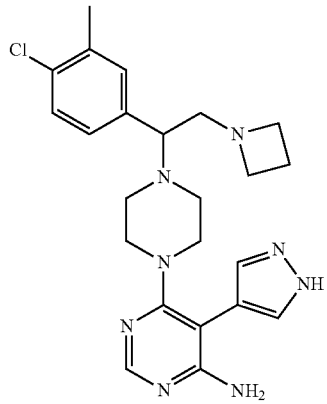 [SMILES: Cc1cc(C(CN2CCC2)N2CCN(c3ncnc(N)c3-c3cn[nH]c3)CC2)ccc1Cl]

The title compound was prepared in an analogous manner as Example (64). LC-MS: (M+1=453, obsd.=453)

4-((S)-1-{4-[6-Amino-5-(4-fluoro-phenyl)-pyrimidin-4-yl]-piperazin-1-yl}-2-azetidin-1-yl-ethyl)-benzoic acid methyl ester ("110")

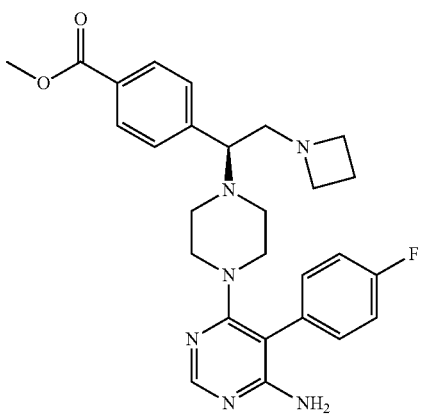

The title compound was prepared in an analogous manner as Example (64) then isolated by the SFC chiral separation. LC-MS: (M+1=491, obsd.=491)

91

4-((R)-1-{4-[6-Amino-5-(4-fluoro-phenyl)-pyrimidin-4-yl]-piperazin-1-yl}-2-azetidin-1-yl-ethyl)-benzoic acid methyl ester ("111")

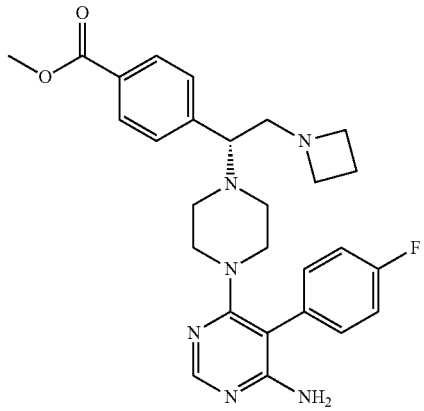

The title compound was prepared in an analogous manner as Example (64) then isolated by the SFC chiral separation. LC-MS: (M+1=491, obsd.=491)

6-{4-[3-Azetidin-1-yl-1-(4-chloro-phenyl)-propyl]-piperazin-1-yl}-5-(4-fluoro-phenyl)-pyrimidin-4-ylamine ("112")

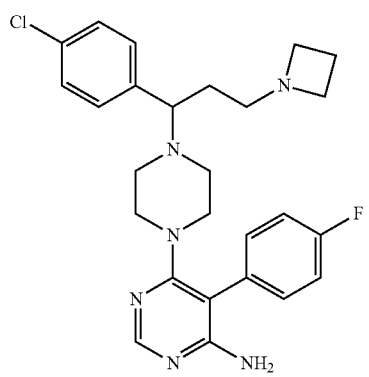 [SMILES: Nc1ncnc(N2CCN(C(CCN3CCC3)c3ccc(Cl)cc3)CC2)c1-c1ccc(F)cc1]

The title compound was prepared in an analogous manner as Example (64). LC-MS: (M+1=482, obsd.=482)

92

6-{4-[4-Azetidin-1-yl-1-(4-chloro-phenyl)-butyl]-piperazin-1-yl}-5-(4-fluoro-phenyl)-pyrimidin-4-ylamine ("113")

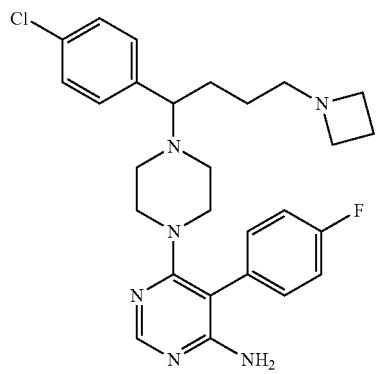 [SMILES: Nc1ncnc(N2CCN(C(CCCN3CCC3)c3ccc(Cl)cc3)CC2)c1-c1ccc(F)cc1]

The title compound was prepared in an analogous manner as Example (64). LC-MS: (M+1=496, obsd.=496)

6-{4-[2-Azetidin-1-yl-1-(4-fluoro-3-trifluoromethoxy-phenyl)-ethyl]-piperazin-1-yl}-5-(1H-pyrazol-4-yl)-pyrimidin-4-ylamine ("114")

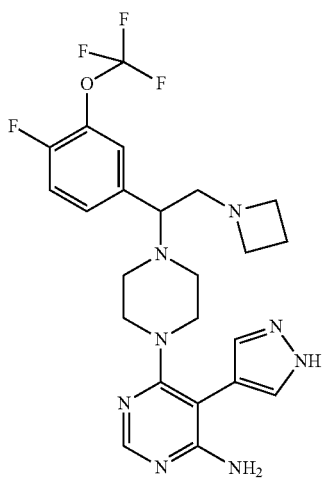 [SMILES: Nc1ncnc(N2CCN(C(CN3CCC3)c3ccc(F)c(OC(F)(F)F)c3)CC2)c1-c1cn[nH]c1]

The title compound was prepared in an analogous manner as Example (64). LC-MS: (M+1=507, obsd.=507)

93

6-{4-[2-Azetidin-1-yl-1-(5,6,7,8-tetrahydro-naphthalen-2-yl)-ethyl]-piperazin-1-yl}-5-(6-piperazin-1-yl-pyridin-3-yl)-pyrimidin-4-ylamine ("115")

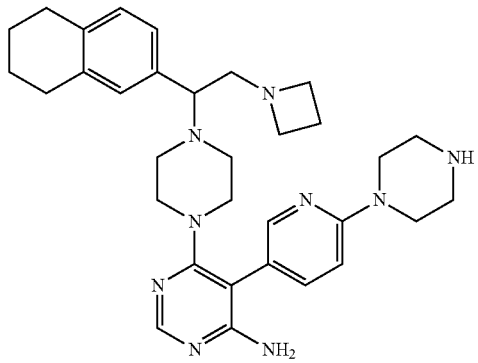 [SMILES: Nc1ncnc(N2CCN(C(CN3CCC3)c3ccc4c(c3)CCCC4)CC2)c1-c1ccc(N2CCNCC2)nc1]

The title compound was prepared in an analogous manner as Example (64). LC-MS: (M+1=554, obsd.=554)

6-{4-[2-Azetidin-1-yl-1-(4-imidazol-1-yl-phenyl)-ethyl]-piperazin-1-yl}-5-(4-fluoro-phenyl)-pyrimidin-4-ylamine ("116")

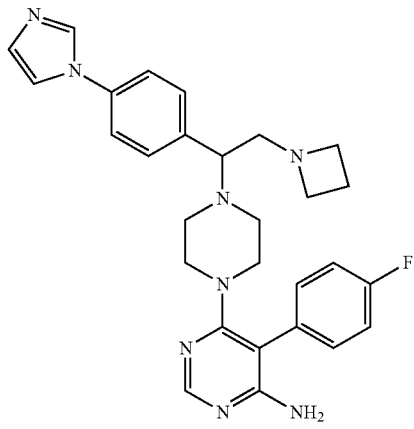 [SMILES: Nc1ncnc(N2CCN(C(CN3CCC3)c3ccc(-n4ccnc4)cc3)CC2)c1-c1ccc(F)cc1]

The title compound was prepared in an analogous manner as Example (64). LC-MS: (M+1=499, obsd.=499)

94

[4-(4-Amino-6-{4-[2-azetidin-1-yl-1-(3,4-dichloro-phenyl)-ethyl]-piperazin-1-yl}-pyrimidin-5-yl)-pyrazol-1-yl]-acetic acid ethyl ester ("117")

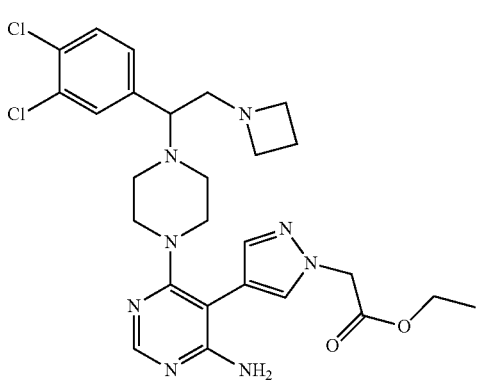 [SMILES: CCOC(=O)Cn1cc(-c2c(N)ncnc2N2CCN(C(CN3CCC3)c3ccc(Cl)c(Cl)c3)CC2)cn1]

The title compound was prepared in an analogous manner as Example (64). LC-MS: (M+1=560, obsd.=560)

6-(1-{4-[6-Amino-5-(4-fluoro-phenyl)-pyrimidin-4-yl]-piperazin-1-yl}-2-azetidin-1-yl-ethyl)-3H-benzothiazol-2-one ("118")

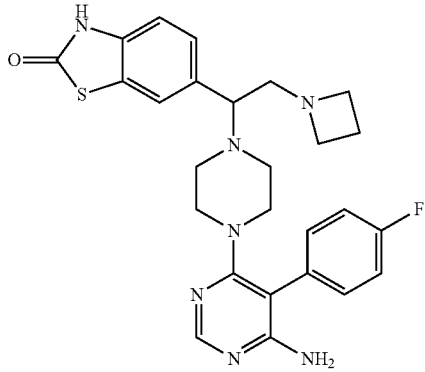 [SMILES: Nc1ncnc(N2CCN(C(CN3CCC3)c3ccc4[nH]c(=O)sc4c3)CC2)c1-c1ccc(F)cc1]

The title compound was prepared in an analogous manner as Example (64). LC-MS: (M+1=506, obsd.=506)

95

[4-(4-Amino-6-{4-[2-azetidin-1-yl-1-(5,6,7,8-tetra-hydro-naphthalen-2-yl)-ethyl]-piperazin-1-yl}-pyrimidin-5-yl)-pyrazol-1-yl]-acetic acid ethyl ester ("119")

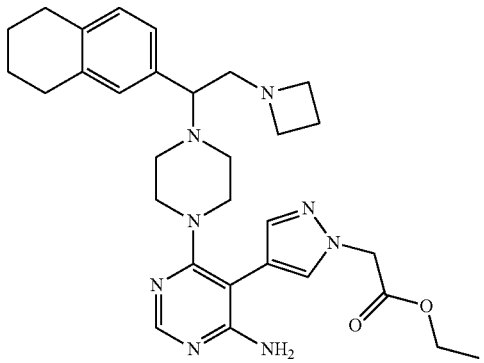 [SMILES: CCOC(=O)Cn1cc(-c2c(N)ncnc2N2CCN(C(CN3CCC3)c3ccc4c(c3)CCCC4)CC2)cn1]

The title compound was prepared in an analogous manner as Example (64). LC-MS: (M+1=545, obsd.=545)

6-{4-[2-Azetidin-1-yl-1-(2-fluoro-4-trifluoromethyl-phenyl)-ethyl]-piperazin-1-yl}-5-(1H-pyrazol-4-yl)-pyrimidin-4-ylamine ("120")

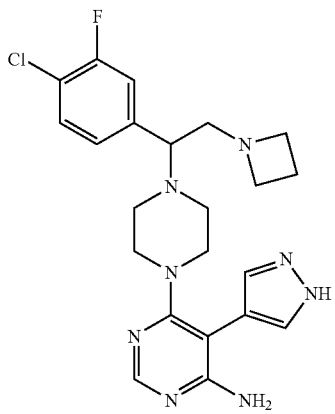 [SMILES: Nc1ncnc(N2CCN(C(CN3CCC3)c3ccc(Cl)c(F)c3)CC2)c1-c1cn[nH]c1]

The title compound was prepared in an analogous manner as Example (64). LC-MS: (M+1=491, obsd.=491)

96

6-{4-[2-Azetidin-1-yl-1-(4-chloro-3-fluoro-phenyl)-ethyl]-piperazin-1-yl}-5-(1H-pyrazol-4-yl)-pyrimidin-4-ylamine ("121")

The title compound was prepared in an analogous manner as Example (64). LC-MS: (M+1=457, obsd.=457)

6-{4-[2-Azetidin-1-yl-1-(5,6,7,8-tetrahydro-naphthalen-2-yl)-ethyl]-piperazin-1-yl}-5-(1H-pyrazol-4-yl)-pyrimidin-4-ylamine ("122")

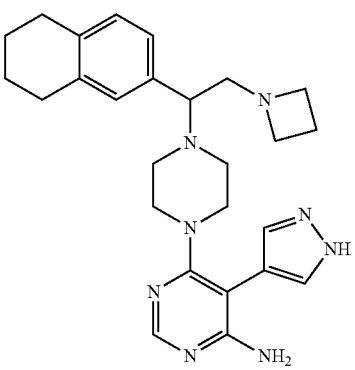 [SMILES: Nc1ncnc(N2CCN(C(CN3CCC3)c3ccc4c(c3)CCCC4)CC2)c1-c1cn[nH]c1]

The title compound was prepared in an analogous manner as Example (64). LC-MS: (M+1=459, obsd.=459)

97

6-{4-[2-Azetidin-1-yl-1-(5,6,7,8-tetrahydro-naphthalen-2-yl)-ethyl]-piperazin-1-yl}-5-(4-fluoro-phenyl)-pyrimidin-4-ylamine ("123")

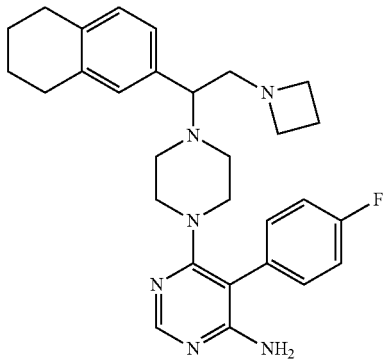 [SMILES: Nc1ncnc(N2CCN(C(CN3CCC3)c3ccc4c(c3)CCCC4)CC2)c1-c1ccc(F)cc1]

The title compound was prepared in an analogous manner as Example (64). LC-MS: (M+1=487, obsd.=487)

6-{4-[2-Azetidin-1-yl-1-(2,3-difluoro-phenyl)-ethyl]-piperazin-1-yl}-5-(1H-pyrazol-4-yl)-pyrimidin-4-ylamine ("124")

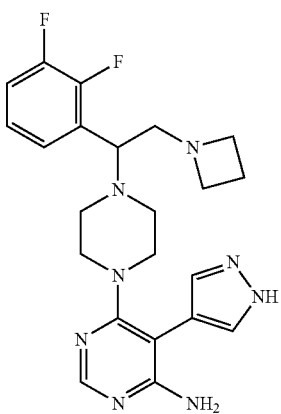 [SMILES: Nc1ncnc(N2CCN(C(CN3CCC3)c3cccc(F)c3F)CC2)c1-c1cn[nH]c1]

The title compound was prepared in an analogous manner as Example (64). LC-MS: (M+1=441, obsd.=441)

98

3-((S)-1-{4-[6-Amino-5-(4-fluoro-phenyl)-pyrimidin-4-yl]-piperazin-1-yl}-2-azetidin-1-yl-ethyl)-benzonitrile ("125")

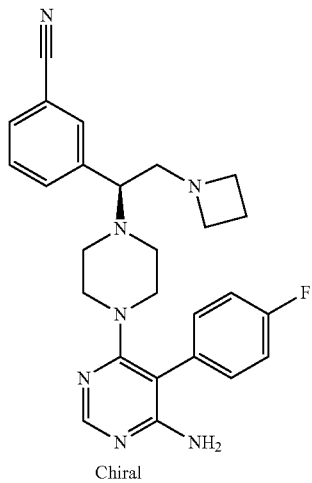 [SMILES: N#Cc1cccc([C@@H](CN2CCC2)N2CCN(c3ncnc(N)c3-c3ccc(F)cc3)CC2)c1]

Chiral

The title compound was prepared in an analogous manner as Example (64) then isolated by the SFC chiral separation. LC-MS: (M+1=458, obsd.=458)

6-{4-[2-Azetidin-1-yl-1-(2,3-dichloro-phenyl)-ethyl]-piperazin-1-yl}-5-(1H-pyrazol-4-yl)-pyrimidin-4-ylamine ("126")

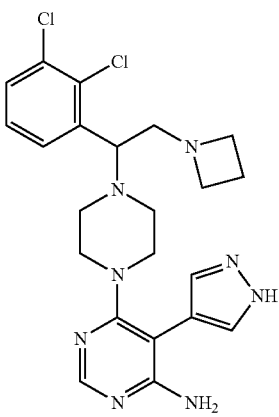 [SMILES: Nc1ncnc(N2CCN(C(CN3CCC3)c3cccc(Cl)c3Cl)CC2)c1-c1cn[nH]c1]

The title compound was prepared in an analogous manner as Example (64). LC-MS: (M+1=474, obsd.=474)

6-{4-[2-Azetidin-1-yl-1-(3-fluoro-4-trifluoromethyl-phenyl)-ethyl]-piperazin-1-yl}-5-(1H-pyrazol-4-yl)-pyrimidin-4-ylamine ("127")

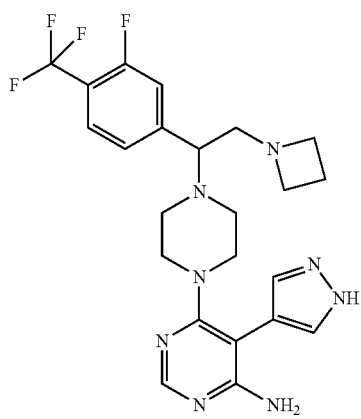 [SMILES: Nc1ncnc(N2CCN(C(CN3CCC3)c3ccc(C(F)(F)F)c(F)c3)CC2)c1-c1cn[nH]c1]

The title compound was prepared in an analogous manner as Example (64). LC-MS: (M+1=491, obsd.=491)

6-{4-[2-Azetidin-1-yl-1-(4-methanesulfonyl-phenyl)-ethyl]-piperazin-1-yl}-5-(4-fluoro-phenyl)-pyrimidin-4-ylamine ("128")

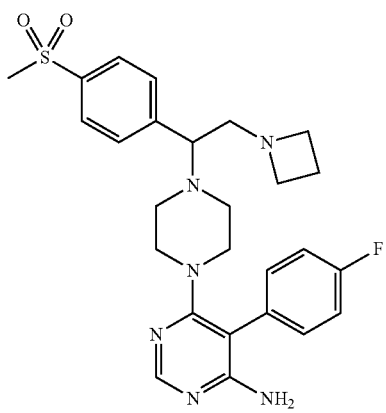 [SMILES: CS(=O)(=O)c1ccc(C(CN2CCC2)N2CCN(c3ncnc(N)c3-c3ccc(F)cc3)CC2)cc1]

The title compound was prepared in an analogous manner as Example (64). LC-MS: (M+1=511, obsd.=511)

3-((R)-1-{4-[6-Amino-5-(4-fluoro-phenyl)-pyrimidin-4-yl]-piperazin-1-yl}-2-azetidin-1-yl-ethyl)-benzonitrile ("129")

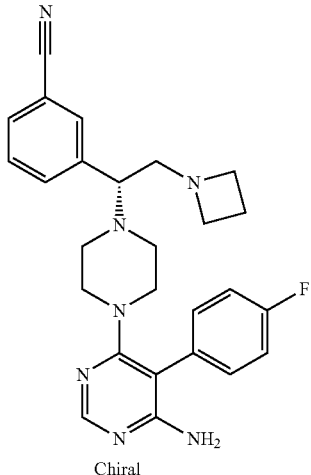 [SMILES: N#Cc1cccc([C@H](CN2CCC2)N2CCN(c3ncnc(N)c3-c3ccc(F)cc3)CC2)c1]

Chiral

The title compound was prepared in an analogous manner as Example (64) then isolated by the SFC chiral separation. LC-MS: (M+1=458, obsd.=458)

[4-(4-Amino-6-{4-[2-azetidin-1-yl-1-(3-cyano-phenyl)-ethyl]-piperazin-1-yl}-pyrimidin-5-yl)-pyrazol-1-yl]-acetic acid methyl ester ("130")

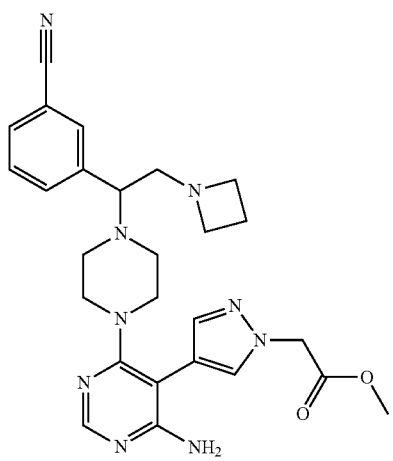 [SMILES: COC(=O)Cn1cc(-c2c(N)ncnc2N2CCN(C(CN3CCC3)c3cccc(C#N)c3)CC2)cn1]

The title compound was prepared in an analogous manner as Example (64). LC-MS: (M+1=502, obsd.=502)

101

6-{4-[2-Azetidin-1-yl-1-(3,4-dichloro-phenyl)-ethyl]-piperazin-1-yl}-5-(1H-pyrazol-4-yl)-pyrimidin-4-ylamine ("131")

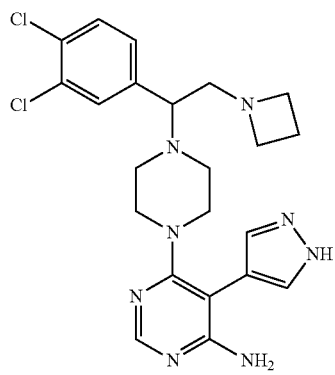 [SMILES: Nc1ncnc(N2CCN(C(CN3CCC3)c3ccc(Cl)c(Cl)c3)CC2)c1-c1cn[nH]c1]

The title compound was prepared in an analogous manner as Example (64). LC-MS: (M+1=474, obsd.=474)

6-{4-[2-Azetidin-1-yl-1-(4-chloro-3-trifluoromethyl-phenyl)-ethyl]-piperazin-1-yl}-5-(1H-pyrazol-4-yl)-pyrimidin-4-ylamine ("132")

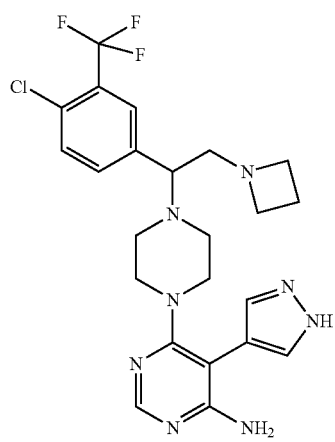 [SMILES: Nc1ncnc(N2CCN(C(CN3CCC3)c3ccc(Cl)c(C(F)(F)F)c3)CC2)c1-c1cn[nH]c1]

The title compound was prepared in an analogous manner as Example (64). LC-MS: (M+1=507, obsd.=507)

102

6-{4-[2-Azetidin-1-yl-1-(3,4-dichloro-phenyl)-ethyl]-piperazin-1-yl}-5-(6-piperazin-1-yl-pyridin-3-yl)-pyrimidin-4-ylamine ("133")

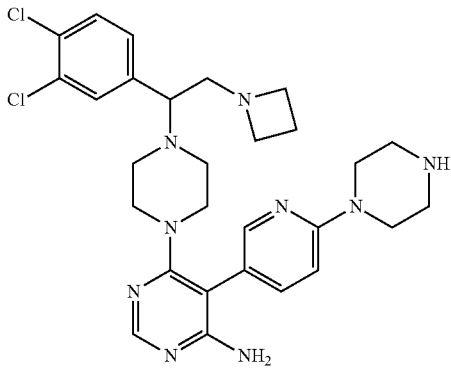 [SMILES: Nc1ncnc(N2CCN(C(CN3CCC3)c3ccc(Cl)c(Cl)c3)CC2)c1-c1ccc(N2CCNCC2)nc1]

The title compound was prepared in an analogous manner as Example (64). LC-MS: (M+1=569, obsd.=569)

6-{4-[2-Azetidin-1-yl-1-(2-chloro-3-trifluoromethyl-phenyl)-ethyl]-piperazin-1-yl}-5-(1H-pyrazol-4-yl)-pyrimidin-4-ylamine ("134")

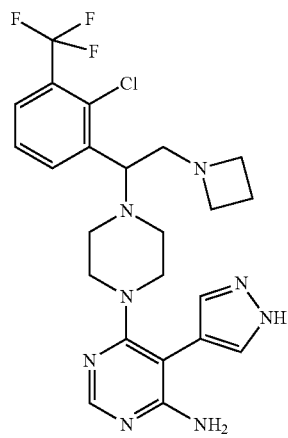 [SMILES: Nc1ncnc(N2CCN(C(CN3CCC3)c3cccc(C(F)(F)F)c3Cl)CC2)c1-c1cn[nH]c1]

The title compound was prepared in an analogous manner as Example (64). LC-MS: (M+1=507, obsd.=507)

103

6-{4-[2-Azetidin-1-yl-1-(3-chloro-4-fluoro-phenyl)-ethyl]-piperazin-1-yl}-5-(1H-pyrazol-4-yl)-pyrimidin-4-ylamine ("135")

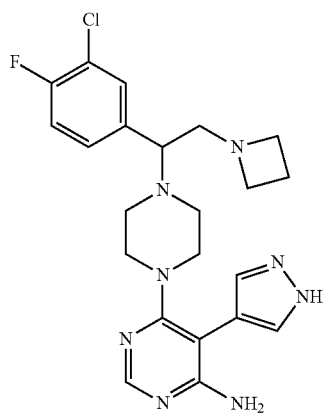 [SMILES: Nc1ncnc(N2CCN(C(CN3CCC3)c3ccc(F)c(Cl)c3)CC2)c1-c1cn[nH]c1]

The title compound was prepared in an analogous manner as Example (64). LC-MS: (M+1=457, obsd.=457)

6-{4-[2-Azetidin-1-yl-1-(2-chloro-4-fluoro-phenyl)-ethyl]-piperazin-1-yl}-5-(1H-pyrazol-4-yl)-pyrimidin-4-ylamine ("137")

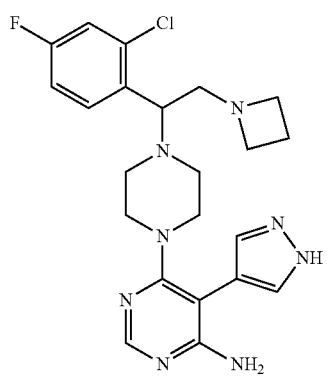 [SMILES: Nc1ncnc(N2CCN(C(CN3CCC3)c3ccc(F)cc3Cl)CC2)c1-c1cn[nH]c1]

The title compound was prepared in an analogous manner as Example (64). LC-MS: (M+1=457, obsd.=457)

Examples (138) to (151) were prepared according to Synthetic Scheme 7.

104

1-6-amino-5-(4-fluorophenyl)pyrimidin-4-yl)piperidin-4-yl-4-(chlorophenyl)methanol ("138")

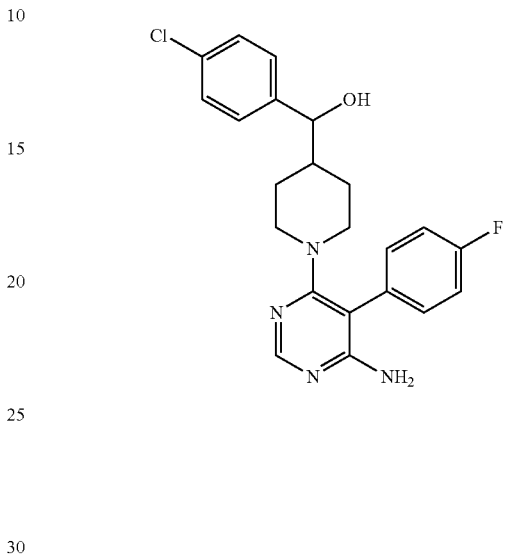

Intermediate (138.1): [1-(6-Amino-5-bromo-pyrimidin-4-yl)-piperidin-4-yl]-(4-chloro-phenyl)-methanone The mixture of 5-bromo-6-chloro-pyrimidine-4-ylamine (2.0 g, 9.59 mmol, 1.0 eq), 4-chlorophenyl-piperidin-4-yl-methanone (2.36 g, 10.55 mmol, 1.10 eq) and potassium carbonate (6.63 g, 47.97 mmol, 5.0 eq) in DMF (5 mL) was stirred at 50° C. overnight. After pouring the reaction mixture to water, the precipitate was collected to give Intermediate (138.1). LC-MS (M+1: 396, obsd: 396).

Intermediate (138.2): {1-[6-Amino-5-(4-fluoro-phenyl)-pyrimidin-4-yl]-piperidin-4-yl}-(4-chloro-phenyl)-methanone A mixture of Intermediate (84.1) (2.0 g, 5.05 mmol, 1.0 eq), 4-fluorophenyl boronic acid (707.24 mg, 5.05 mmol, 1.0 eq), palladium acetate (113.48 mg, 0.5 mmol, 1.0 eq), s-phosphine (415.01 mg, 1.01 mmol, 0.2 eq), and cesium carbonate (3293.76 mg, 10.11 mmol, 2.0 eq) in 1,4-dioxane (10 mL) and water (1.0 mL) in the sealed vial was stirred at 50° C. overnight. After usual workup, the crude was purified through preparative HPLC purification to yield Intermediate (138.2). LC-MS (M+1: 411, obsd: 411).

To a solution of Intermediate (138.2) (500 mg, 1.22 mmol, 1.0 eq) in methanol (15 mL) was added sodium borohydride (70 mg, 1.85 mmol, 1.5 eq). The mixture was stirred overnight. After concentration, the mixture was diluted with ethyl acetate and washed with brine. The organic layer was dried over $MgSO_4$, concentrated and purified by flash chromatography on silicon gel to afford the title compound. MS-LC (M+1: 414, obsd: 414).

105

1-6-amino-5-(4-fluorophenyl)pyrimidin-4-yl)piperidin-4-yl-4-(4-fluorophenyl)phenyl)methanol ("139")

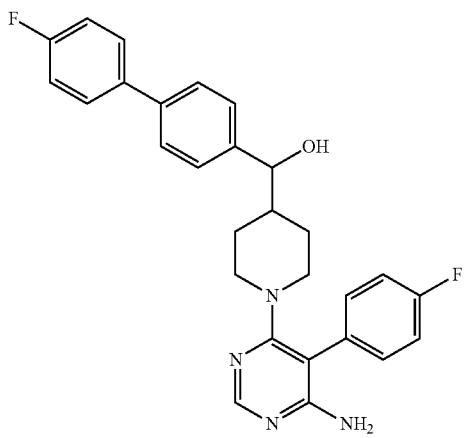 [SMILES: Nc1ncnc(N2CCC(C(O)c3ccc(-c4ccc(F)cc4)cc3)CC2)c1-c1ccc(F)cc1]

The title compound was prepared in an analogous manner as Example (138). LC-MS (M+1=473, obsd=473)

1-6-amino-5-(4-fluoropheny)pyrimidin-4-yl)piperidin-4-yl-4-(fluorophenyl)methanol ("140")

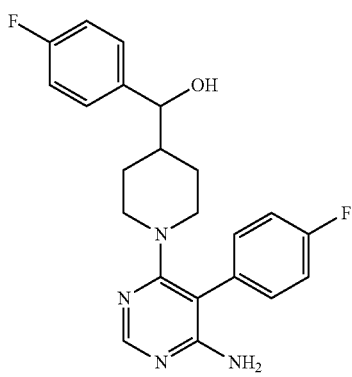 [SMILES: Nc1ncnc(N2CCC(C(O)c3ccc(F)cc3)CC2)c1-c1ccc(F)cc1]

The title compound was prepared in an analogous manner as Example (138). LC-MS (M+1=397, obsd=397)

106

1-6-amino-5-(vinylpyrimidin-4-yl)piperidin-4-yl-4-(fluorophenyl)methanol ("141")

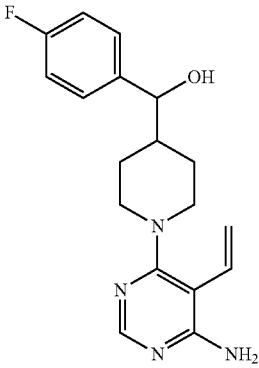 [SMILES: C=Cc1c(N)ncnc1N1CCC(C(O)c2ccc(F)cc2)CC1]

The title compound was prepared in an analogous manner as Example (138). LC-MS (M+1=329, obsd=329)

5-(4-Fluorophenyl)-6{4-amino(4-chlorophenyl)methyl-piperidin-1-yl}pyrimidin-4-amine ("142")

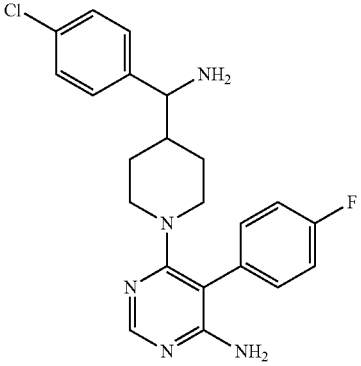 [SMILES: Nc1ncnc(N2CCC(C(N)c3ccc(Cl)cc3)CC2)c1-c1ccc(F)cc1]

To a solution of Intermediate (138.2) (150 mg, 0.38 mmol, 1.0 eq) and ammonium acetate (337 mg, 4.3 mmol, 12 eq.) in methanol (5 mL) was added sodium cyanoborohydride (1.90 mmol, 5 eq). The mixture was refluxed for 2 days. After concentration, the mixture was diluted with ethyl acetate and washed with brine. The organic layer was dried over MgSO$_4$, concentrated and purified through flash chromatography on silicon gel to afford the title compound. LC-MS (M+1=413, obsd=413)

107

5-(4-Fluorophenyl)-6{4-amino(4-fluorophenyl)methyl-piperidin-1-yl}pyrimidin-4-amine ("143")

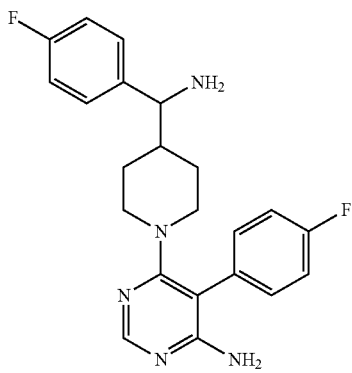

The title compound was prepared in an analogous manner as Example (142). LC-MS (M+1=396, obsd=396)

5-(4-Fluorophenyl)-6{4-amino(4-(4-fluorophenyl)phenyl)methyl-piperidin-1-yl}pyrimidin-4-amine ("144")

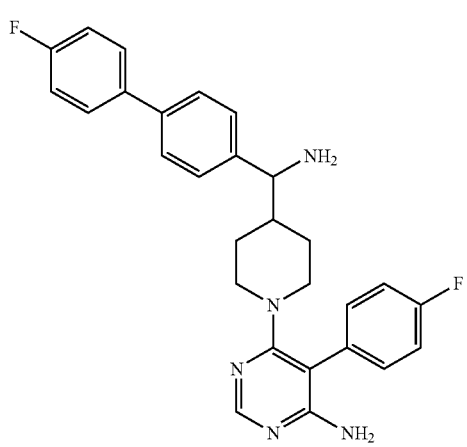

The title compound was prepared in an analogous manner as Example (142). LC-MS (M+1=472, obsd=472)

108

6-(4-((cyclopentylamino)(4-fluorophenyl)piperidin-1-yl)-5-(4-fluorophenyl)pyrimidin-4-amine ("145")

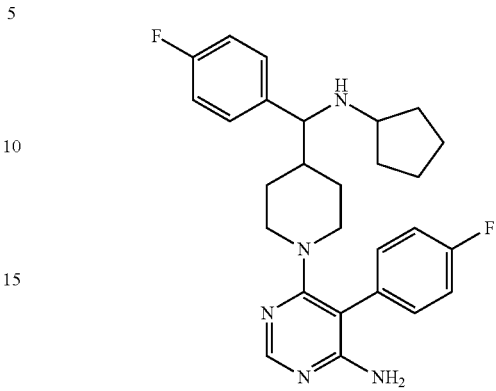

The title compound was prepared in an analogous manner as Example (142). LC-MS (M+1=464, obsd=464)

5-(4-fluoropheny)6-(4-((4-fluorophenyl)(2-(pyrrolidin-1-yl)ethoxy)methyl)-piperidin-1-yl)pyrimidin-4-amine ("146")

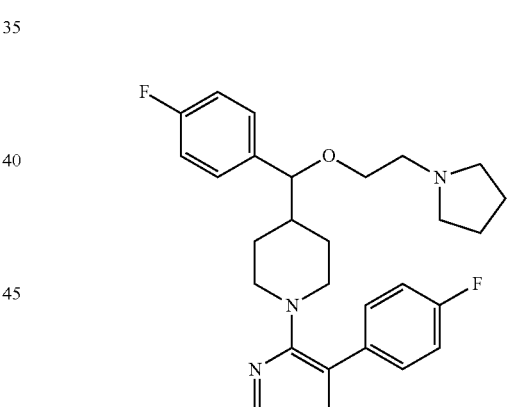

To a solution of Example (138) (150 mg, 0.38 mmol, 1.0 eq) in DMF (10 mL) was added sodium hydride (75.67 mg, 1.89 mmol, 5.0 eq). The mixture was stirred for 10 minutes, then 1-(2-chloro-ethyl)pyrrolidine hydrochloride (77.22 mg, 0.45 mmol, 1.2 eq) was added. The mixture was stirred at 70° C. overnight. After standard workup, the title compound was obtained through reverse phase HPLC purification. LC-MS (M+1=494, obsd=494)

5-(4-fluoropheny)6-(4-((4-fluorophenyl)(2-(dimethylamino) ethoxy)methyl)piperidin-1-yl)pyrimidin-4-amine ("147")

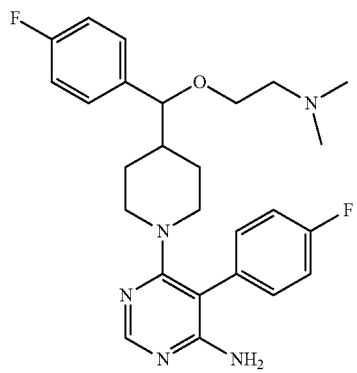 [SMILES: CN(C)CCOC(c1ccc(F)cc1)C1CCN(c2ncnc(N)c2-c2ccc(F)cc2)CC1]

The title compound was prepared in an analogous manner as Example (146). LC-MS (M+1=468, obsd=468)

5-(4-fluoropheny)-6-(4-((4-fluorophenyl)(pyrrolidin-1-yl)methyl)piperidin-1-yl)pyrimidin-4-amine ("148")

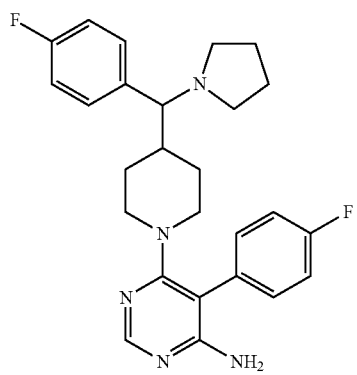 [SMILES: Nc1ncnc(N2CCC(C(c3ccc(F)cc3)N3CCCC3)CC2)c1-c1ccc(F)cc1]

Intermediate (148.1): 6-{4-[Chloro-(4-fluoro-phenyl)-methyl]-piperidin-1-yl}-5-(4-fluoro-phenyl)-pyrimidin-4-ylamine To a solution of Example (140) (700 mg, 1.77 mmol, 1.0 eq) in DCM (10 mL) was added thionyl chloride (0.32 mL, 4.41 mmol, 2.5 eq) dropwise. The mixture was stirred overnight. After removal of the solvents, the solid was suspended in ethyl acetate and filtered to give Intermediate (94.1). LC-MS (M+1: 415, obsd: 415)

A mixture of Intermediate (148.1) (50 mg, 0.12 mmol, 1.0 eq), pyrrolidine (17.14 mg, 0.24 mmol, 2 eq) and DIEA (77.88 mg, 0.60 mmol, 5 eq) in NMP (3 mL) was stirred at 120° C. overnight. The title compound was obtained through reverse phase HPLC purification. LC-MS (M+1=450, obsd=450)

5-(4-fluoropheny)-6-(4-((4-fluorophenyl)(3-difluoropyrrolidin-1-yl)methyl)piperidin-1-yl)pyrimidin-4-amine ("149")

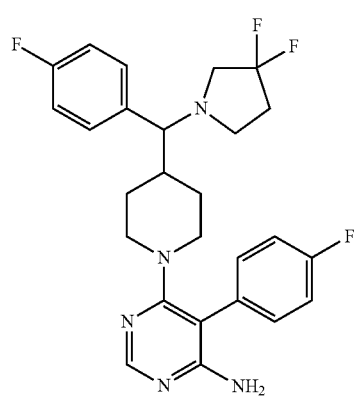 [SMILES: Nc1ncnc(N2CCC(C(c3ccc(F)cc3)N3CCC(F)(F)C3)CC2)c1-c1ccc(F)cc1]

The title compound was prepared in an analogous manner as Example (148). LC-MS (M+1=486, obsd=486)

1-(6-amino-5-(4-fluoropheny)pyrimidin-4-yl)(4-((4-fluorophenyl))methyl)-dimethylethane-1,2-diamine ("150")

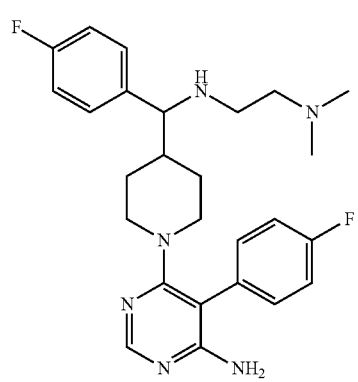 [SMILES: CN(C)CCNC(c1ccc(F)cc1)C1CCN(c2ncnc(N)c2-c2ccc(F)cc2)CC1]

The title compound was prepared in an analogous manner as Example (148). LC-MS (M+1=467, obsd=467)

111

5-(4-fluorophenyl)-(6-(4-fluoropheny)piperidin-4-ylmethyl)amino)methyl)piperidin-1-yl)pyrimidin-4-amine ("151")

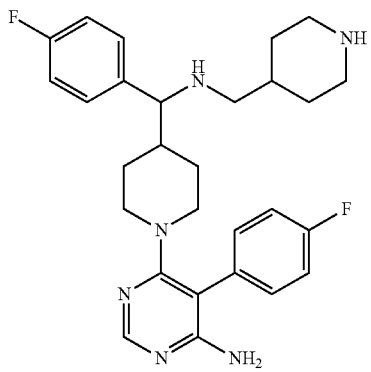 [SMILES: Nc1ncnc(N2CCC(C(NCC3CCNCC3)c3ccc(F)cc3)CC2)c1-c1ccc(F)cc1]

The title compound was prepared in an analogous manner as Example (148). LC-MS (M+1=493, obsd=493)

Examples (152) to (194) were prepared according to Synthetic Scheme 8.

{4-[6-Amino-5-(4-fluoro-phenyl)-pyrimidin-4-yl]-piperazin-1-yl}-(3-trifluoromethyl-phenyl)-acetonitrile ("152")

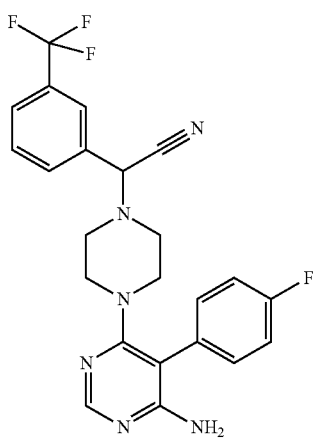 [SMILES: N#CC(c1cccc(C(F)(F)F)c1)N1CCN(c2ncnc(N)c2-c2ccc(F)cc2)CC1]

In a round bottom flask equipped with a stir bar was dissolved 5-(4-Fluoro-phenyl)-6-piperazin-1-yl-pyrimidin-4-ylamine (1 eq) and 3-trifluoromethyl-benzaldehyde (1.05 eq) in acetonitrile. The vial was sealed with a rubber septa, then evacuated and backfilled with argon. To this sealed vessel was added trimethylsilyl cyanide (1.05 eq) and the reaction was allowed to stir at room temperature until complete. The reaction is quenched by addition of an equal amount of ammonium chloride (saturated, aqueous solution), then extracted with ethyl acetate. The organic layers are then dried over sodium sulfate, filtered and concentrated to give the title compound. LC-MS: (M+1=457, obsd.=457).

112

6-{4-[2-Amino-1-(3-trifluoromethyl-phenyl)-ethyl]-piperazin-1-yl}-5-(4-fluoro-phenyl)-pyrimidin-4-ylamine ("153")

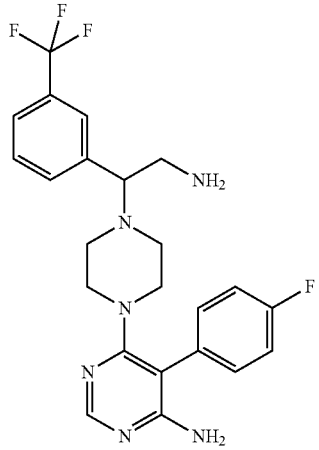 [SMILES: NCC(c1cccc(C(F)(F)F)c1)N1CCN(c2ncnc(N)c2-c2ccc(F)cc2)CC1]

To a stirred mixture of Example (152) (76.0 mg; 0.17 mmol; 1.0 eq.) and Cobalt chloride (2.2 mg; 0.02 mmol; 0.1 eq.) in Methanol (5.0 ml), sodium borohydride (32.8 mg; 0.83 mmol; 5.0 eq.) was added in portions at 0° C. Reaction was left at RT after addition and stirred until deemed complete by LCMS. The mixture was purified through reverse phase HPLC to provide the title compound. LC-MS: (M+1=461, obsd.=461).

{4-[6-Amino-5-(4-fluoro-phenyl)-pyrimidin-4-yl]-piperazin-1-yl}-(4-fluoro-3-trifluoromethyl-phenyl)-acetonitrile ("154")

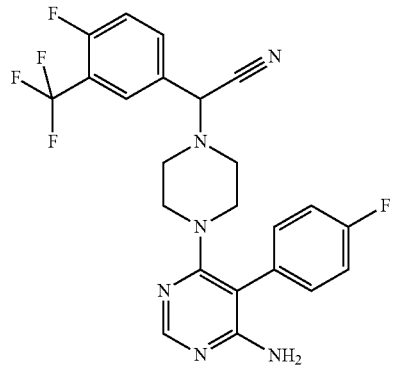 [SMILES: N#CC(c1ccc(F)c(C(F)(F)F)c1)N1CCN(c2ncnc(N)c2-c2ccc(F)cc2)CC1]

The title compound was prepared in an analogous manner as Example (152). LC-MS: (M+1=475, obsd.=475)

6-{4-[2-Amino-1-(4-fluoro-3-trifluoromethyl-phenyl)-ethyl]-piperazin-1-yl}-5-(4-fluoro-phenyl)-pyrimidin-4-ylamine ("155")

6-{4-[2-Amino-1-(3,4-dichloro-phenyl)-ethyl]-piperazin-1-yl}-5-(4-fluoro-phenyl)-pyrimidin-4-ylamine ("157")

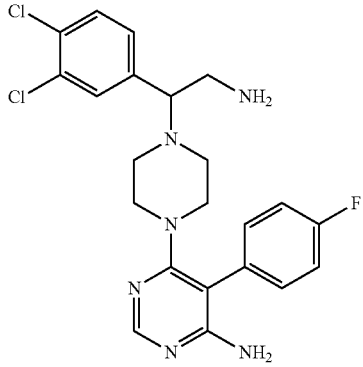

The title compound was prepared in an analogous manner as Example (153). LC-MS: (M+1=461, obsd.=461).

{4-[6-Amino-5-(4-fluoro-phenyl)-pyrimidin-4-yl]-piperazin-1-yl}-(4-fluoro-phenyl)-acetonitrile ("158")

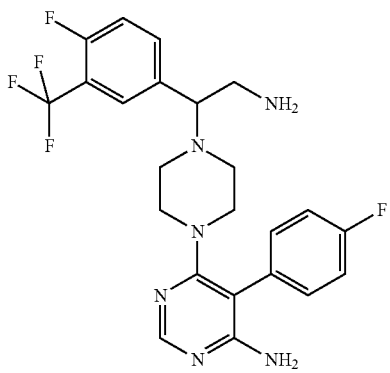 [SMILES: NCC(c1ccc(F)c(C(F)(F)F)c1)N1CCN(c2ncnc(N)c2-c2ccc(F)cc2)CC1]

The title compound was prepared in an analogous manner as Example (153). LC-MS: (M+1=479, obsd.=479).

{4-[6-Amino-5-(4-fluoro-phenyl)-pyrimidin-4-yl]-piperazin-1-yl}-(3,4-dichloro-phenyl)-acetonitrile ("156")

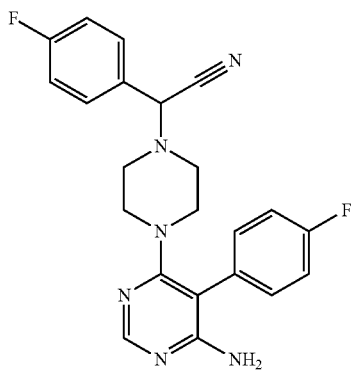

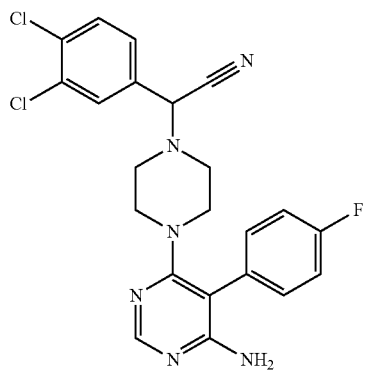 [SMILES: N#CC(c1ccc(Cl)c(Cl)c1)N1CCN(c2ncnc(N)c2-c2ccc(F)cc2)CC1]

The title compound was prepared in an analogous manner as Example (152). LC-MS: (M+1=457, obsd.=457)

The title compound was prepared in an analogous manner as Example (152). LC-MS: (M+1=407, obsd.=407)

115

6-{4-[2-Amino-1-(4-fluoro-phenyl)-ethyl]-piperazin-1-yl}-5-(4-fluoro-phenyl)-pyrimidin-4-ylamine ("159")

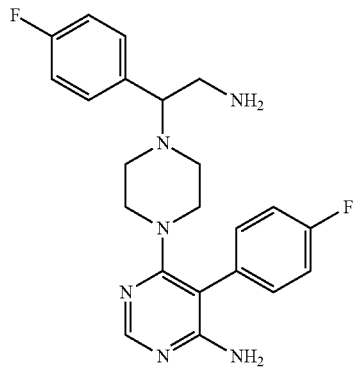

The title compound was prepared in an analogous manner as Example (153). LC-MS: (M+1=411, obsd.=411).

{4-[6-Amino-5-(4-fluoro-phenyl)-pyrimidin-4-yl]-piperazin-1-yl}-(3-chloro-4-fluoro-phenyl)-acetonitrile ("160")

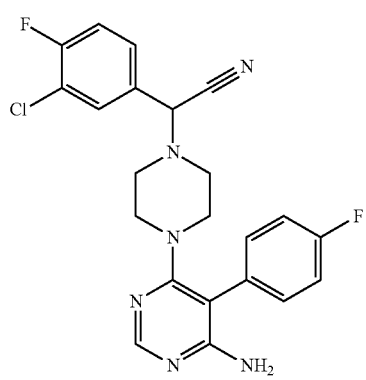

The title compound was prepared in an analogous manner as Example (152). LC-MS: (M+1=441, obsd.=441)

116

6-{4-[2-Amino-1-(3-chloro-4-fluoro-phenyl)-ethyl]-piperazin-1-yl}-5-(4-fluoro-phenyl)-pyrimidin-4-ylamine ("161")

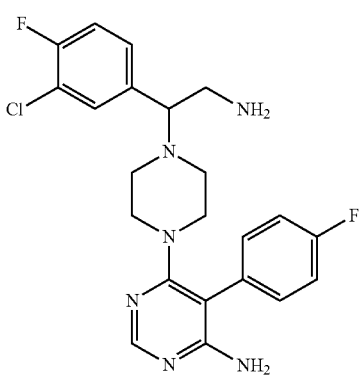 [SMILES: NCC(c1ccc(F)c(Cl)c1)N1CCN(c2ncnc(N)c2-c2ccc(F)cc2)CC1]

The title compound was prepared in an analogous manner as Example (153). LC-MS: (M+1=445, obsd.=445).

{4-[6-Amino-5-(4-fluoro-phenyl)-pyrimidin-4-yl]-piperazin-1-yl}-(4-chloro-phenyl)-acetonitrile ("162")

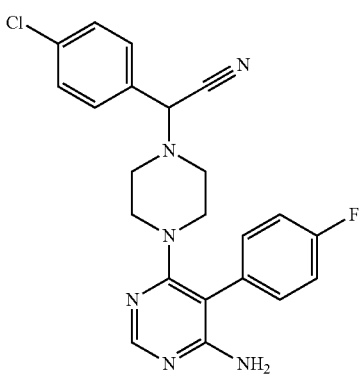 [SMILES: N#CC(c1ccc(Cl)cc1)N1CCN(c2ncnc(N)c2-c2ccc(F)cc2)CC1]

The title compound was prepared in an analogous manner as Example (152). LC-MS: (M+1=423, obsd.=423).

117

6-{4-[2-Amino-1-(4-chloro-phenyl)-ethyl]-piperazin-1-yl}-5-(4-fluoro-phenyl)-pyrimidin-4-ylamine ("163")

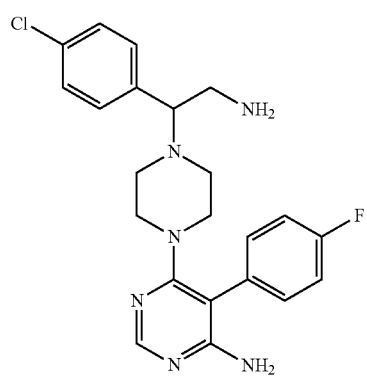 [SMILES: NCC(c1ccc(Cl)cc1)N1CCN(c2ncnc(N)c2-c2ccc(F)cc2)CC1]

The title compound was prepared in an analogous manner as Example (153). LC-MS: (M+1=427, obsd.=427).

{4-[6-Amino-5-(4-fluoro-phenyl)-pyrimidin-4-yl]-piperazin-1-yl}-(4-chloro-3-fluoro-phenyl)-acetonitrile ("164")

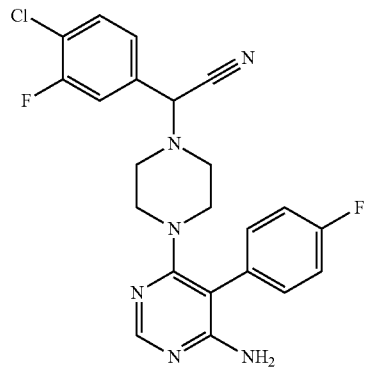 [SMILES: N#CC(c1ccc(Cl)c(F)c1)N1CCN(c2ncnc(N)c2-c2ccc(F)cc2)CC1]

The title compound was prepared in an analogous manner as Example (152). LC-MS: (M+1=441, obsd.=441)

118

6-{4-[2-Amino-1-(4-chloro-3-fluoro-phenyl)-ethyl]-piperazin-1-yl}-5-(4-fluoro-phenyl)-pyrimidin-4-ylamine ("165")

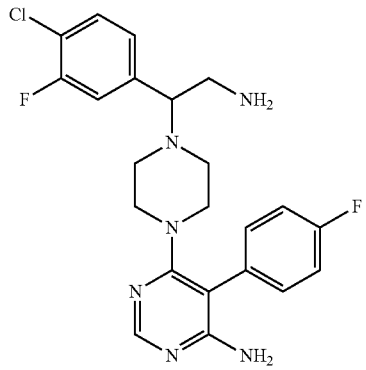 [SMILES: NCC(c1ccc(Cl)c(F)c1)N1CCN(c2ncnc(N)c2-c2ccc(F)cc2)CC1]

The title compound was prepared in an analogous manner as Example (153). LC-MS: (M+1=445, obsd.=445)

[4-(6-Amino-5-bromo-pyrimidin-4-yl)-piperazin-1-yl]-(3-trifluoromethyl-phenyl)-acetonitrile ("166")

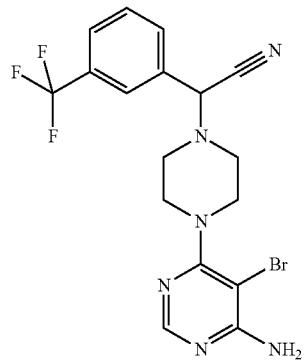 [SMILES: N#CC(c1cccc(C(F)(F)F)c1)N1CCN(c2ncnc(N)c2Br)CC1]

The title compound was prepared in an analogous manner as Example (152). LC-MS: (M+1=442, obsd.=442)

119

[4-(6-Amino-5-bromo-pyrimidin-4-yl)-piperazin-1-yl]-(4-trifluoromethyl-phenyl)-acetonitrile ("167")

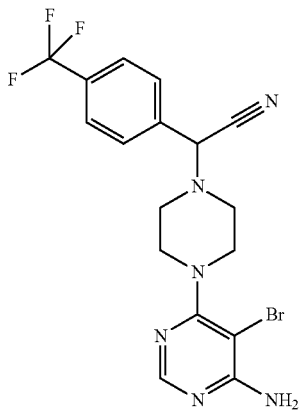 [SMILES: N#CC(c1ccc(C(F)(F)F)cc1)N1CCN(c2ncnc(N)c2Br)CC1]

The title compound was prepared in an analogous manner as Example (152). LC-MS: (M+1=442, obsd.=442)

{4-[6-Amino-5-(4-fluoro-phenyl)-pyrimidin-4-yl]-piperazin-1-yl}-(4-trifluoromethyl-phenyl)-acetonitrile ("168")

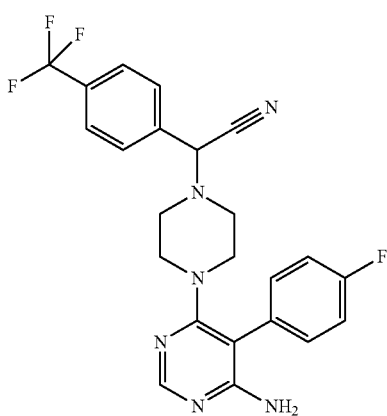 [SMILES: N#CC(c1ccc(C(F)(F)F)cc1)N1CCN(c2ncnc(N)c2-c2ccc(F)cc2)CC1]

The title compound was prepared in an analogous manner as Example (152). LC-MS: (M+1=442, obsd.=442)

120

6-{4-[2-Amino-1-(3-fluoro-phenyl)-ethyl]-piperazin-1-yl}-5-(4-fluoro-phenyl)-pyrimidin-4-ylamine ("169")

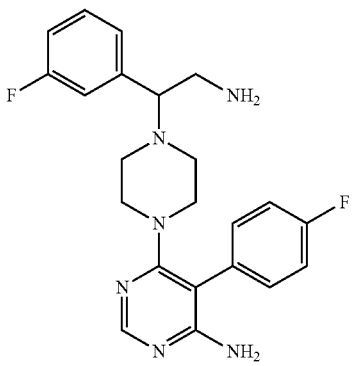 [SMILES: NCC(c1cccc(F)c1)N1CCN(c2ncnc(N)c2-c2ccc(F)cc2)CC1]

The title compound was prepared in an analogous manner as Example (153). LC-MS: (M+1=411, obsd.=411)

6-{4-[2-Amino-1-(2-fluoro-4-trifluoromethyl-phenyl)-ethyl]-piperazin-1-yl}-5-(4-fluoro-phenyl)-pyrimidin-4-ylamine ("170")

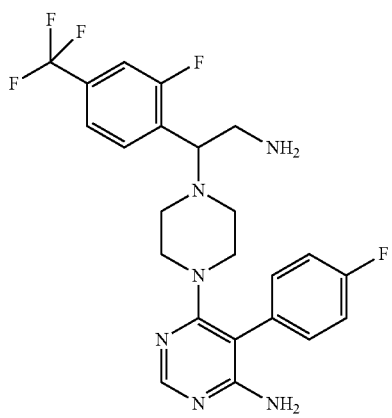 [SMILES: NCC(c1ccc(C(F)(F)F)cc1F)N1CCN(c2ncnc(N)c2-c2ccc(F)cc2)CC1]

The title compound was prepared in an analogous manner as Example (153). LC-MS: (M+1=479, obsd.=479)

6-[4-((1R,2R)-1-Aminomethyl-2-phenyl-propyl)-piperazin-1-yl]-5-(4-fluoro-phenyl)-pyrimidin-4-ylamine ("171")

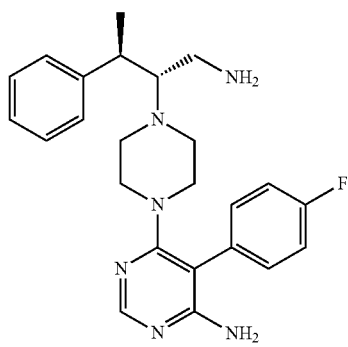 [SMILES: C[C@H](c1ccccc1)[C@H](CN)N1CCN(c2ncnc(N)c2-c2ccc(F)cc2)CC1]

The title compound was prepared in an analogous manner as Example (153) then isolated by the SFC chiral separation. LC-MS: (M+1=421, obsd.=421)

6-[4-((1R,2S)-1-Aminomethyl-2-phenyl-propyl)-piperazin-1-yl]-5-(4-fluoro-phenyl)-pyrimidin-4-ylamine ("172")

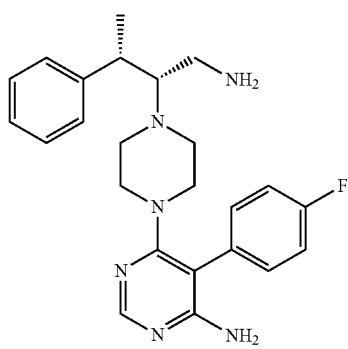 [SMILES: C[C@@H](c1ccccc1)[C@H](CN)N1CCN(c2ncnc(N)c2-c2ccc(F)cc2)CC1]

The title compound was prepared in an analogous manner as Example (153) then isolated by the SFC chiral separation. LC-MS: (M+1=421, obsd.=421)

{4-[6-Amino-5-(4-fluoro-phenyl)-pyrimidin-4-yl]-piperazin-1-yl}-(6-chloro-pyridin-3-yl)-acetonitrile ("173")

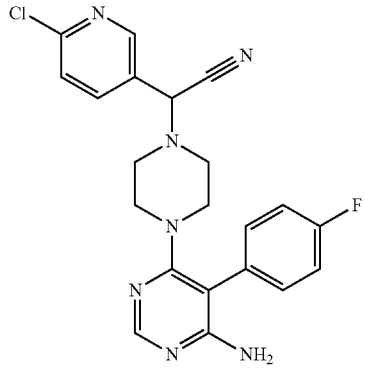 [SMILES: N#CC(c1ccc(Cl)nc1)N1CCN(c2ncnc(N)c2-c2ccc(F)cc2)CC1]

The title compound was prepared in an analogous manner as Example (152). LC-MS: (M+1=424, obsd.=424)

6-{4-[2-Amino-1-(6-chloro-pyridin-3-yl)-ethyl]-piperazin-1-yl}-5-(4-fluoro-phenyl)-pyrimidin-4-ylamine ("174")

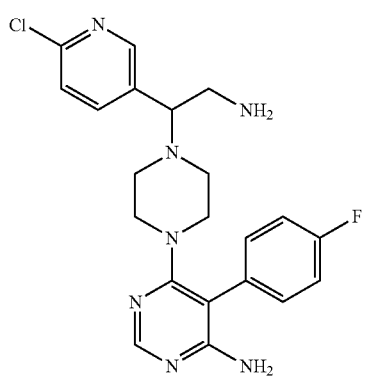 [SMILES: NCC(c1ccc(Cl)nc1)N1CCN(c2ncnc(N)c2-c2ccc(F)cc2)CC1]

The title compound was prepared in an analogous manner as Example (153). LC-MS: (M+1=428, obsd.=428)

123

6-{4-[(R)-2-Amino-1-(6-chloro-pyridin-3-yl)-ethyl]-piperazin-1-yl}-5-(4-fluoro-phenyl)-pyrimidin-4-ylamine ("175")

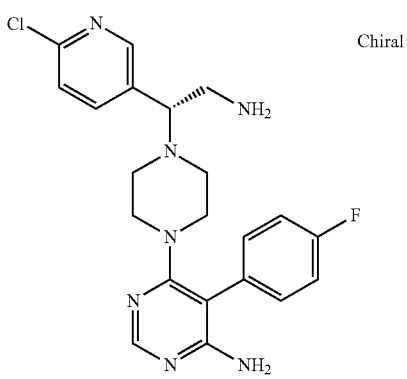 [SMILES: NC[C@@H](c1ccc(Cl)nc1)N1CCN(c2ncnc(N)c2-c2ccc(F)cc2)CC1]

The title compound was isolated by the SFC chiral separation of Example (174). LC-MS: (M+1=428, obsd.=428)

6-{4-[(S)-2-Amino-1-(6-chloro-pyridin-3-yl)-ethyl]-piperazin-1-yl}-5-(4-fluoro-phenyl)-pyrimidin-4-ylamine ("176")

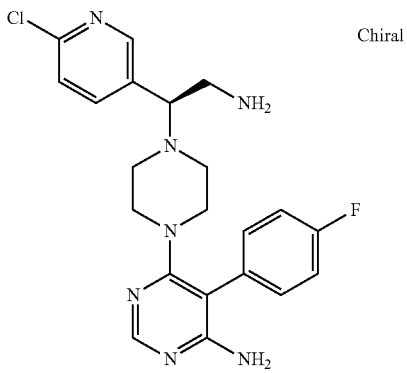 [SMILES: NC[C@H](c1ccc(Cl)nc1)N1CCN(c2ncnc(N)c2-c2ccc(F)cc2)CC1]

The title compound was isolated by the SFC chiral separation of Example (174). LC-MS: (M+1=428, obsd.=428)

124

6-{4-[2-Amino-1-(6-chloro-pyridin-3-yl)-ethyl]-piperazin-1-yl}-5-ethyl-pyrimidin-4-ylamine ("177")

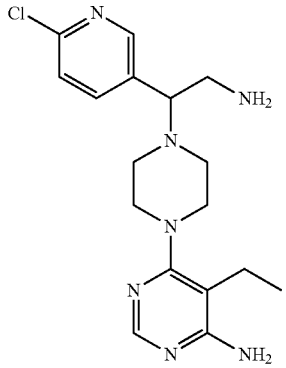 [SMILES: CCc1c(N)ncnc1N1CCN(C(CN)c2ccc(Cl)nc2)CC1]

The title compound was prepared in an analogous manner as Example (153). LC-MS: (M+1=362, obsd.=362)

6-{4-[2-Amino-1-(4-chloro-phenyl)-ethyl]-piperazin-1-yl}-5-ethyl-pyrimidin-4-ylamine ("178")

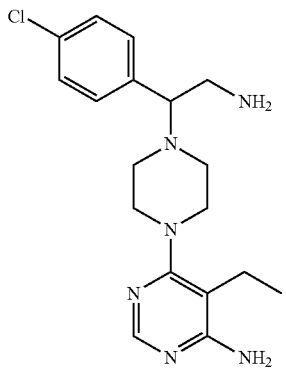 [SMILES: CCc1c(N)ncnc1N1CCN(C(CN)c2ccc(Cl)cc2)CC1]

The title compound was prepared in an analogous manner as Example (153). LC-MS: (M+1=361, obsd.=361)

6-{4-[(S)-2-Amino-1-(4-chloro-phenyl)-ethyl]-piperazin-1-yl}-5-ethyl-pyrimidin-4-ylamine ("179")

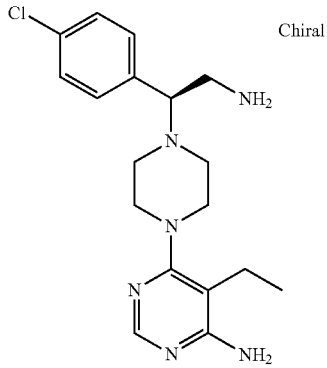 [SMILES: CCc1c(N)ncnc1N1CCN([C@H](CN)c2ccc(Cl)cc2)CC1]

The title compound was isolated by the SFC chiral separation of Example (178). LC-MS: (M+1=361, obsd.=361)

6-{4-[(R)-2-Amino-1-(4-chloro-phenyl)-ethyl]-piperazin-1-yl}-5-ethyl-pyrimidin-4-ylamine ("180")

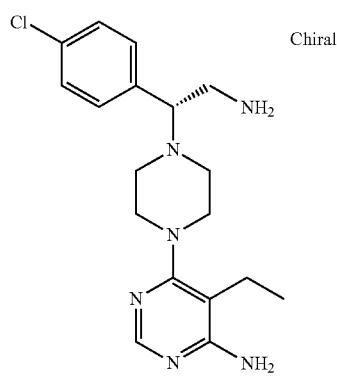 [SMILES: CCc1c(N)ncnc1N1CCN([C@@H](CN)c2ccc(Cl)cc2)CC1]

The title compound was isolated by the SFC chiral separation of Example (178). LC-MS: (M+1=361, obsd.=361)

6-{4-[2-Amino-1-(2,3-dihydro-benzo[1,4]dioxin-6-yl)-ethyl]-piperazin-1-yl}-5-ethyl-pyrimidin-4-ylamine ("181")

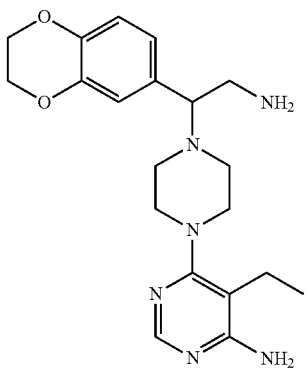 [SMILES: CCc1c(N)ncnc1N1CCN(C(CN)c2ccc3c(c2)OCCO3)CC1]

The title compound was prepared in an analogous manner as Example (153). LC-MS: (M+1=385, obsd.=385)

2-(4-(6-amino-5-(4-fluorophenyl)pyrimidin-4-yl)piperazin-1-yl)-2-(6-methoxypyridin-3-yl)acetonitrile ("182")

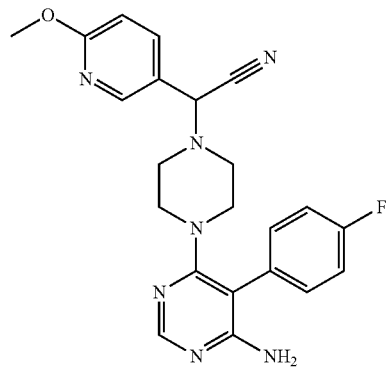 [SMILES: COc1ccc(C(C#N)N2CCN(c3ncnc(N)c3-c3ccc(F)cc3)CC2)cn1]

The title compound was prepared in an analogous manner as Example (152). LC-MS (M+1=420, obsd.=420).

6-(4-(2-amino-1-(6-methoxypyridin-3-yl)ethyl)piperazin-1-yl)-5-(4-fluorophenyl)pyrimidin-4-amine ("183")

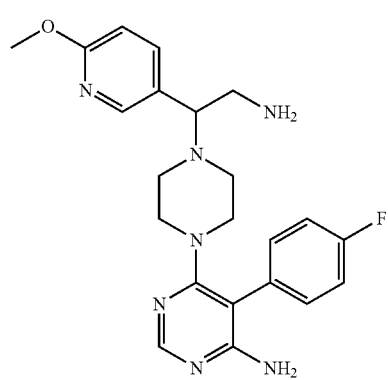 [SMILES: COc1ccc(C(CN)N2CCN(c3ncnc(N)c3-c3ccc(F)cc3)CC2)cn1]

The title compound was prepared in an analogous manner as Example (153). LC-MS (M+1=424, obsd.=424).

127

2-(4-(6-amino-5-(1H-pyrazol-4-yl)pyrimidin-4-yl)piperazin-1-yl)-2-(4-(methylsulfonyl)phenyl)acetonitrile ("184")

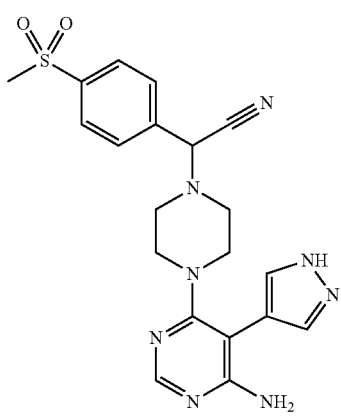 [SMILES: CS(=O)(=O)c1ccc(C(C#N)N2CCN(c3ncnc(N)c3-c3cn[nH]c3)CC2)cc1]

The title compound was prepared in an analogous manner as Example (152). LC-MS: (M+1=439, obsd.=439).

6-(4-(2-amino-1-(4-(methylsulfonyl)phenyl)ethyl)piperazin-1-yl)-5-(1H-pyrazol-4-yl)pyrimidin-4-amine ("185")

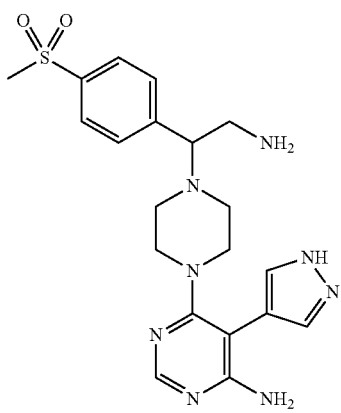 [SMILES: CS(=O)(=O)c1ccc(C(CN)N2CCN(c3ncnc(N)c3-c3cn[nH]c3)CC2)cc1]

The title compound was prepared in an analogous manner as Example (153). LC-MS (M+1=443, obsd.=443).

128

6-(4-(2-amino-1-(4-(trifluoromethoxy)phenyl)ethyl)piperazin-1-yl)-5-(1H-pyrazol-4-yl)pyrimidin-4-amine ("186")

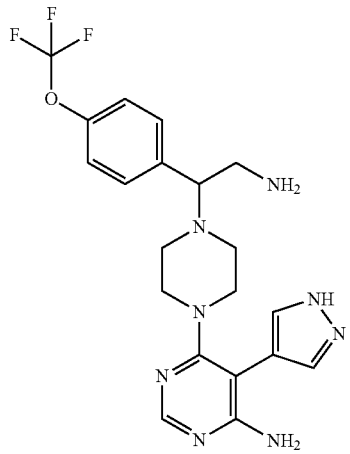 [SMILES: NCC(c1ccc(OC(F)(F)F)cc1)N1CCN(c2ncnc(N)c2-c2cn[nH]c2)CC1]

The title compound was prepared in an analogous manner as Example (153). LC-MS (M+1=449, obsd.=449).

6-(4-(2-amino-1-(4-chloro-3-fluorophenyl)ethyl)piperazin-1-yl)-5-(1H-pyrazol-4-yl)pyrimidin-4-amine ("187")

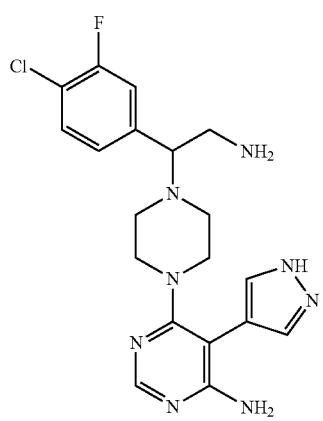 [SMILES: NCC(c1ccc(Cl)c(F)c1)N1CCN(c2ncnc(N)c2-c2cn[nH]c2)CC1]

The title compound was prepared in an analogous manner as Example (153). LC-MS (M+1=417, obsd.=417).

6-[4-(2-Amino-1-cyclohexyl-ethyl)-piperazin-1-yl]-5-ethyl-pyrimidin-4-ylamine ("188")

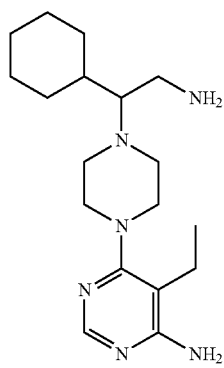 [SMILES: CCc1c(N)ncnc1N1CCN(C(CN)C2CCCCC2)CC1]

To a solution of [4-(6-Amino-5-ethyl-pyrimidin-4-yl)-piperazin-1-yl]-cyclohexyl-acetonitrile (28.00 mg; 0.09 mmol; 1.00 eq.) in THF (4.00 ml; 49.37 mmol; 579.16 eq.), lithium 9-bbn hydride (0.38 ml; 0.38 mmol; 4.50 eq.) in THF was added, and the mixture stirred at 50° C. for four hours. LC-MS analysis indicated the reaction is incomplete, starting material still present. Add 0.1 ml more of lithium 9-bbn hydride solution and stir the reaction mixture overnight at 60° C. LC-MS analysis indicated the reaction was complete. The reaction mixture was filtered through a glass membrane syringe filter unit and evaporated to dryness. The residue was dissolved in DMSO (3 ml) and purified by reverse phase HPLC (Waters, basic buffer) to afford the title compound (13.9 mg; 0.04 mmol) as a white glass in 47.2% yield. LC-MS: (M+1=333.4, obsd.=333.3).

{4-[6-Amino-5-(4-fluoro-phenyl)-pyrimidin-4-yl]-piperazin-1-yl}-(6-trifluoromethyl-pyridin-3-yl)-acetonitrile ("189")

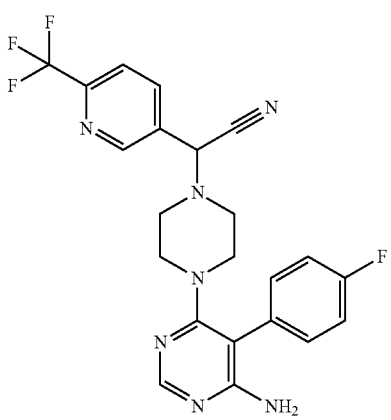 [SMILES: N#CC(c1ccc(C(F)(F)F)nc1)N1CCN(c2ncnc(N)c2-c2ccc(F)cc2)CC1]

The title compound was prepared in an analogous manner as Example (152). LC-MS: (M+1=458.4, obsd.=458.2).

{4-[6-Amino-5-(4-fluoro-phenyl)-pyrimidin-4-yl]-piperazin-1-yl}-pyridin-3-yl-acetonitrile ("190")

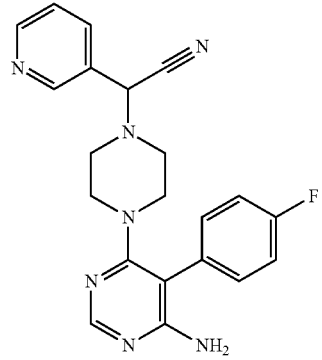 [SMILES: N#CC(c1cccnc1)N1CCN(c2ncnc(N)c2-c2ccc(F)cc2)CC1]

The title compound was prepared in an analogous manner as Example (152). LC-MS: (M+1=390.4, obsd.=390.2).

{4-[6-Amino-5-(4-fluoro-phenyl)-pyrimidin-4-yl]-piperazin-1-yl}-cyclohexyl-acetonitrile ("191")

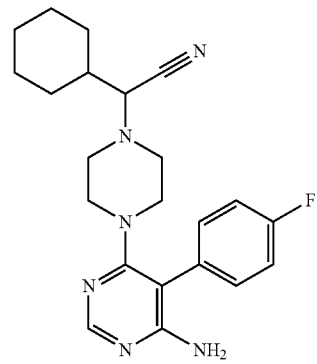 [SMILES: N#CC(C1CCCCC1)N1CCN(c2ncnc(N)c2-c2ccc(F)cc2)CC1]

The title compound was prepared in an analogous manner as Example (152). LC-MS: (M+1=395.5, obsd.=395.3).

6-{4-[2-Amino-1-(2-fluoro-5-trifluoromethyl-phenyl)-ethyl]-piperazin-1-yl}-5-(4-fluoro-phenyl)-pyrimidin-4-ylamine ("192")

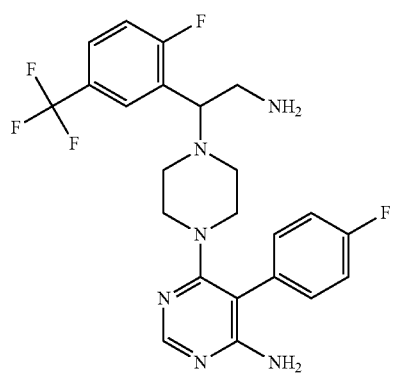 [SMILES: NCC(c1cc(C(F)(F)F)ccc1F)N1CCN(c2ncnc(N)c2-c2ccc(F)cc2)CC1]

The title compound was prepared in an analogous manner as Example (153). LC-MS: (M+1=479.4, obsd.=479.3).

6-[4-(2-Amino-1-pyridin-3-yl-ethyl)-piperazin-1-yl]-5-(4-fluoro-phenyl)-pyrimidin-4-ylamine ("193")

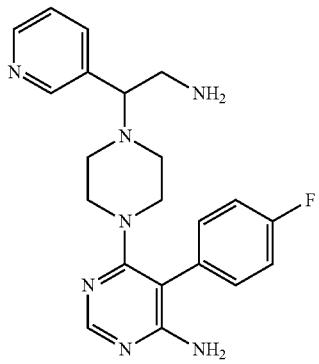 [SMILES: NCC(c1cccnc1)N1CCN(c2ncnc(N)c2-c2ccc(F)cc2)CC1]

The title compound was prepared in an analogous manner as Example (153). LC-MS: (M+1=394.4, obsd.=394.2).

6-{4-[2-Amino-1-(6-trifluoromethyl-pyridin-3-yl)-ethyl]-piperazin-1-yl}-5-(4-fluoro-phenyl)-pyrimidin-4-ylamine ("194")

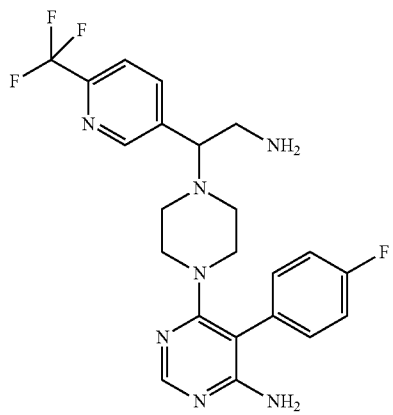 [SMILES: NCC(c1ccc(C(F)(F)F)nc1)N1CCN(c2ncnc(N)c2-c2ccc(F)cc2)CC1]

The title compound was obtained by the hydrogenation of {4-[6-Amino-5-(4-fluoro-phenyl)-pyrimidin-4-yl]-piperazin-1-yl}-(6-trifluoromethyl-pyridin-3-yl)-acetonitrile (20.00 mg; 0.04 mmol; 1.00 eq.) in 15 ml of Methanol and 50 mg of Pd/C 10% stirring in a Parr shaker overnight at room temperature and purified by reverse phase low pressure chromatography (Yamazen, basic buffer). LC-MS: (M+1=462.4, obsd.=462.5).

Examples (195) to (208) were prepared according to Synthetic Scheme 9.

N-[3-Amino-1-(6-amino-5-bromo-pyrimidin-4-yl)-pyrrolidin-3-ylmethyl]-2,4-difluoro-benzamide ("195")

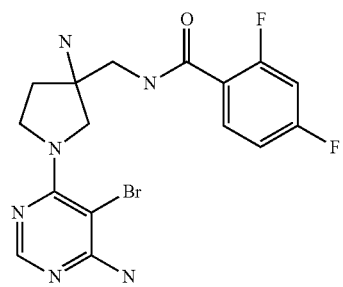 [SMILES: Nc1ncnc(N2CCC(N)(CNC(=O)c3ccc(F)cc3F)C2)c1Br]

A mixture of 5-bromo-6-chloropyrimidin-4-amine (272.7 mg; 1.24 mmol; 1.02 eq.), N-[(3-aminopyrrolidin-3-yl)-methyl]-2,4-difluorobenzamide dihydrochloride (400.0 mg; 1.22 mmol; 1.0 eq.), potassium carbonate (336.8 mg; 2.44 mmol; 2.0 eq.) in DMSO (5.00 ml) was stirred at 60° C. overnight. The react ion mixture was workup and the crude was purified by reverse phase pre-HPLC (Waters, basic condition) to afford the title compound in 76% yield. LC-MS: (M+1=427, obsd.=427).

N-[3-Amino-1-(6-amino-5-cyano-pyrimidin-4-yl)-pyrrolidin-3-ylmethyl]-2,4-difluoro-benzamide ("196")

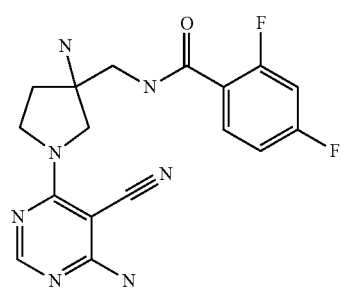 [SMILES: N#Cc1c(N)ncnc1N1CCC(N)(CNC(=O)c2ccc(F)cc2F)C1]

A mixture of 4-amino-6-chloropyrimidine-5-carbonitrile (72.0 mg; 0.47 mmol; 1.02 eq.), N-[(3-aminopyrrolidin-3-yl)methyl]-2,4-difluorobenzamide dihydrochloride (150.0 mg; 0.46 mmol; 1.0 eq.), potassium carbonate (126.3 mg; 0.91 mmol; 2.0 eq.) in DMSO (2.00 ml) was stirred at 60° C. for 2 h. The re action mixture was workup and the crude was purified by reverse phase pre-HPLC (Waters, acetonitrile/0.1% NH4OH in water) to afford the title compound in 70% yield. LC-MS: (M+1=374, obsd.=374).

4-Amino-6-{3-amino-3-[(2,4-difluoro-benzoylamino)-methyl]-pyrrolidin-1-yl}-pyrimidine-5-carboxamide ("197")

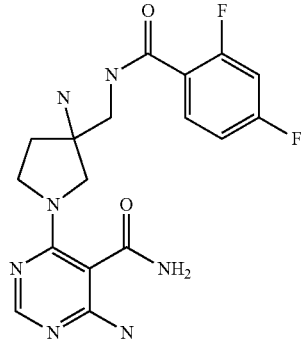 [SMILES: NC(=O)c1c(N)ncnc1N1CCC(N)(CNC(=O)c2ccc(F)cc2F)C1]

Hydrogen peroxide (0.38 ml; 4.29 mmol; 40.0 eq.) was added dropwise to the mixture of N-{[3-amino-1-(6-amino-5-cyanopyrimidin-4-yl)pyrrolidin-3-yl]methyl}-2,4-difluorobenzamide (40.0 mg; 0.11 mmol; 1.0 eq.) and potassium carbonate (118.45 mg; 0.86 mmol; 8.0 eq.) in DMSO (3.0 ml) at room temperature. The resulting mixture was then stirred at 40° C. for 2 hours. The reaction mixture was workup and the crude was purified by reverse phase chromatography (Yamazen, acetonitrile/0.1% NH4OH in water) to yield the title compound in 40% yield. LC-MS: (M+1=392, obsd.=392).

N-{3-Amino-1-[6-amino-5-(4-fluoro-phenyl)-pyrimidin-4-yl]-pyrrolidin-3-ylmethyl}-2,4-difluorobenzamide ("198")

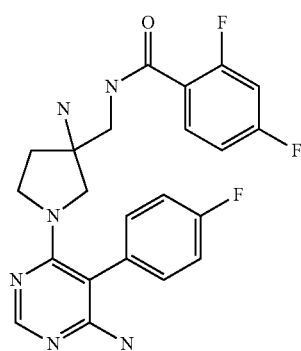 [SMILES: Nc1ncnc(N2CCC(N)(CNC(=O)c3ccc(F)cc3F)C2)c1-c1ccc(F)cc1]

A mixture of N-{[3-amino-1-(6-amino-5-bromopyrimidin-4-yl)pyrrolidin-3-yl]methyl}-2,4-difluorobenzamide (70.0 mg; 0.16 mmol; 1.0 eq.), 4-fluorophenylboronic acid (45.8 mg; 0.33 mmol; 2.0 eq.), palladium acetate (1.8 mg; 0.01 mmol; 0.05 eq.), dicyclohexyl(2',6'-dimethoxybiphenyl-2-yl)phosphine (6.7 mg; 0.02 mmol; 0.10 eq.) and cesium carbonate (160.1 mg; 0.49 mmol; 3.0 eq.) in dioxane (4 ml) and water (0.5 ml) in the microwave vial was heated at 100° C. for 30 min. The reaction mixture was workup and the crude was purified by pre-HPLC (Waters, acetonitrile/0.1% NH4OH in water) to afford the title compound in 61% yield. LC-MS: (M+1=443, obsd.=443).

N-{3-Amino-1-[6-amino-5-(4-cyano-phenyl)-pyrimidin-4-yl]-pyrrolidin-3-ylmethyl}-2,4-difluorobenzamide ("199")

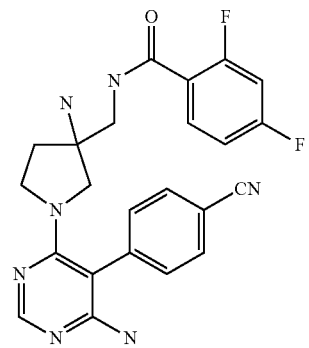 [SMILES: N#Cc1ccc(-c2c(N)ncnc2N2CCC(N)(CNC(=O)c3ccc(F)cc3F)C2)cc1]

The title compound was prepared in an analogous manner as Example (198). LC-MS: (M+1=450, obsd.=450).

N-{3-Amino-1-[6-amino-5-(4-phenoxy-phenyl)-pyrimidin-4-yl]-pyrrolidin-3-ylmethyl}-2,4-difluorobenzamide ("200")

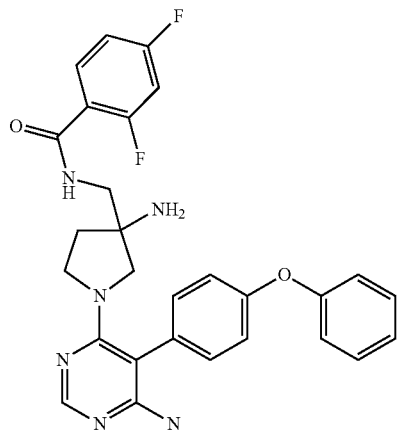 [SMILES: Nc1ncnc(N2CCC(N)(CNC(=O)c3ccc(F)cc3F)C2)c1-c1ccc(Oc2ccccc2)cc1]

The title compound was prepared in an analogous manner as Example (198). LC-MS: (M+1=517, obsd.=517).

135

N-{3-Amino-1-[6-amino-5-(6-methoxy-pyridin-3-yl)-pyrimidin-4-yl]-pyrrolidin-3-ylmethyl}-2,4-difluoro-benzamide ("201")

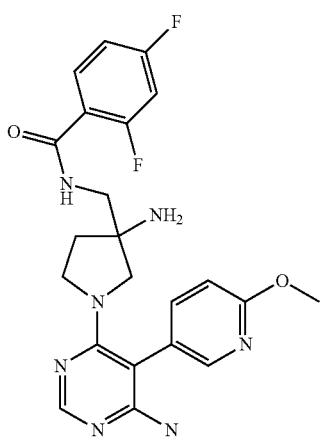 [SMILES: COc1ccc(-c2c(N)ncnc2N2CCC(N)(CNC(=O)c3ccc(F)cc3F)C2)cn1]

The title compound was prepared in an analogous manner as Example (198). LC-MS: (M+1=456, obsd.=456).

N-{3-Amino-1-[6-amino-5-(4-trifluoromethyl-phenyl)-pyrimidin-4-yl]-pyrrolidin-3-ylmethyl}-2,4-difluoro-benzamide ("202")

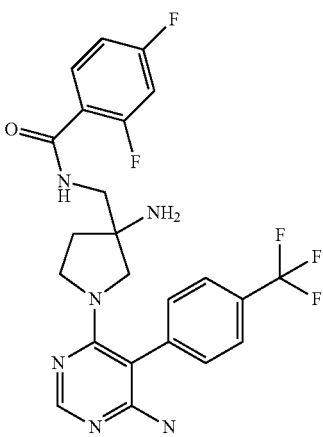 [SMILES: Nc1ncnc(N2CCC(N)(CNC(=O)c3ccc(F)cc3F)C2)c1-c1ccc(C(F)(F)F)cc1]

The title compound was prepared in an analogous manner as Example (198). LC-MS: (M+1=493, obsd.=493).

136

N-[3-Amino-1-(6-amino-5-phenyl-pyrimidin-4-yl)-pyrrolidin-3-ylmethyl]-2,4-difluoro-benzamide ("203")

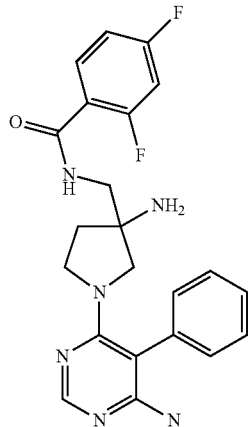 [SMILES: Nc1ncnc(N2CCC(N)(CNC(=O)c3ccc(F)cc3F)C2)c1-c1ccccc1]

The title compound was prepared in an analogous manner as Example (198). LC-MS: (M+1=425, obsd.=425).

N-{3-Amino-1-[6-amino-5-(3-fluoro-phenyl)-pyrimidin-4-yl]-pyrrolidin-3-ylmethyl}-2,4-difluoro-benzamide ("204")

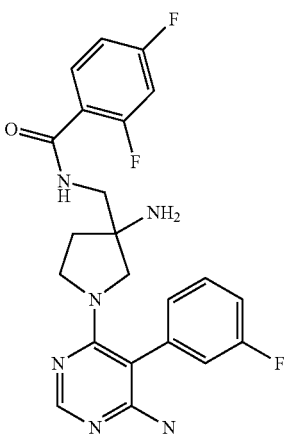 [SMILES: Nc1ncnc(N2CCC(N)(CNC(=O)c3ccc(F)cc3F)C2)c1-c1cccc(F)c1]

The title compound was prepared in an analogous manner as Example (198). LC-MS: (M+1=443, obsd.=443).

137

N-[3-Amino-1-(6-amino-5-pyridin-4-yl-pyrimidin-4-yl)-pyrrolidin-3-ylmethyl]-2,4-difluoro-benzamide ("205")

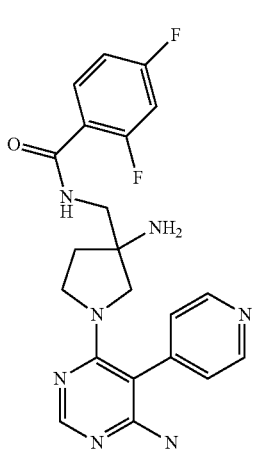 [SMILES: Nc1ncnc(N2CCC(N)(CNC(=O)c3ccc(F)cc3F)C2)c1-c1ccncc1]

The title compound was prepared in an analogous manner as Example (198). LC-MS: (M+1=426, obsd.=426).

N-{3-Amino-1-[6-amino-5-(6-piperazin-1-yl-pyridin-3-yl]-pyrimidin-4-yl]-pyrrolidin-3-ylmethyl}-2,4-difluoro-benzamide ("206")

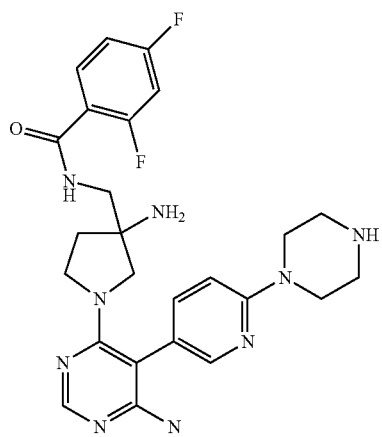 [SMILES: Nc1ncnc(N2CCC(N)(CNC(=O)c3ccc(F)cc3F)C2)c1-c1ccc(N2CCNCC2)nc1]

The title compound was prepared in an analogous manner as Example (198). LC-MS: (M+1=510, obsd.=510).

138

N-[4-Amino-1-(6-amino-5-bromo-pyrimidin-4-yl)-piperidin-4-ylmethyl]-2,4-difluoro-benzamide ("207")

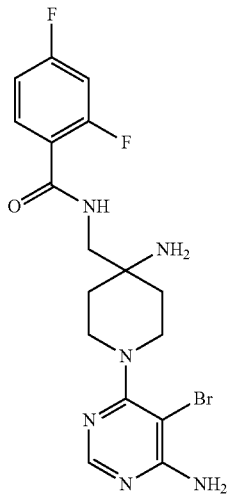 [SMILES: Nc1ncnc(N2CCC(N)(CNC(=O)c3ccc(F)cc3F)CC2)c1Br]

Intermediate 207.1: N-(4-Amino-piperidin-4-ylmethyl)-2,4-difluoro-benzamide dihydrochloride To a solution of 4-Amino-4-aminomethyl-piperidine-1-carboxylic acid tert-butyl ester (250 mg; 1.1 mmol; 1.0 eq.) in pyridine (12 ml) at room temperature, a 0.1 M DCM solution of 2,4-difluoro-benzoyl chloride (182.8 mg; 1.04 mmol; 0.95 eq.) was added slowly. The reaction mixture was quenched by adding 0.5 mL of methanol when LC-MS showing no starting material remaining. The reaction mixture and concentrated to dryness to afford 4-Amino-4-[(2,4-difluoro-benzoylamino)-methyl]-piperidine-1-carboxylic acid tert-butyl ester.

A mixture of the crude 4-amino-4-[(2,4-difluoro-benzoylamino)-methyl]-piperidine-1-carboxylic acid tert-butyl ester (300 mg; 0.82 mmol; 1.0 eq.) and 4M hydrogen chloride in 1,4-dioxane (2.0 ml; 8.1 mmol; 10 eq.) in methanol (2 ml) was stirred at room temperature for 2 h. LC-MS showed the reaction is done. Ether was added. The precipitate was filtered, washed with ether and dried to yield the Intermediate (207.1) as an off-white solid in 68% yield.

Example (207) was prepared in an analogous manner as Example (195) using the Intermediate (207.1) instead of N-[(3-aminopyrrolidin-3-yl)-methyl]-2,4-difluorobenzamide dihydrochloride. LC-MS: (M+1=441, obsd.=441).

N-{4-Amino-1-[6-amino-5-(4-fluoro-phenyl)-pyrimidin-4-yl]-piperidin-4-ylmethyl}-2,4-difluoro-benzamide ("208")

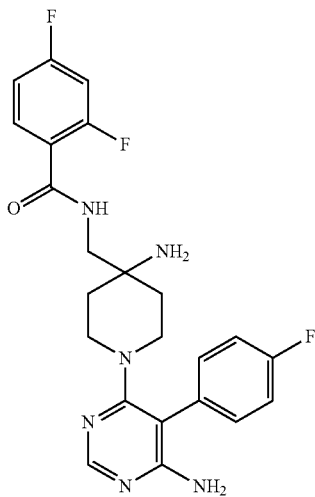 [SMILES: Nc1ncnc(N2CCC(N)(CNC(=O)c3ccc(F)cc3F)CC2)c1-c1ccc(F)cc1]

The title compound was prepared in an analogous manner as Example (198). LC-MS: (M+1=457, obsd.=457).

Examples (214) to (247) were prepared according to Synthetic Scheme 10.

4-Amino-1-(6-amino-5-ethyl-pyrimidin-4-yl)-piperidine-4-carboxylic acid [(S)-1-(4-chloro-phenyl)-3-hydroxy-propyl]-amide ("214")

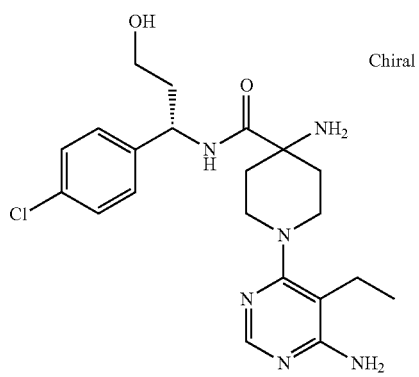 [SMILES: CCc1c(N)ncnc1N1CCC(N)(C(=O)N[C@@H](CCO)c2ccc(Cl)cc2)CC1]

Intermediate 214.1: (S)-4-amino-N-(1-(4-chlorophenyl)-3-hydroxypropyl)piperidine-4-carboxamide To 4-tert-Butoxycarbonylamino-piperidine-1,4-dicarboxylic acid mono-tert-butyl ester (1350.00 mg; 3.92 mmol; 1.00 eq.) in DMF (10 ml) was added HATU (1639.48 mg; 4.31 mmol; 1.10 eq.) and stirred at RT for 40 mins. DIEA (1.48 ml; 8.23 mmol; 2.10 eq.) was added, followed by (S)-3-amino-3-(4-chloro-phenyl)-propan-1-ol (1013.56 mg; 3.92 mmol; 1.00 eq.). The reaction mixture was stirred for another 3 h. The reaction solution was poured into water (100 ml) and extracted with ethylacetate. The separated organic layer was washed with brine, dried and concentrated. The residue was treated with ether to afford the a white solid, which was added 5 ml of methanol, 10 ml of 4.0 MHCl in dioxane and stirred at RT overnight. The precipitate was filtered and was washed with ether to yield Intermediate (214.1) as white solid.

The reaction mixture of 6-chloro-5-ethyl-pyrimidin-4-ylamine (50.0 mg; 0.32 mmol; 1.0 eq.), Intermediate (214.1) (140.3 mg; 0.33 mmol; 1.05 eq.) and DIEA (131.54 mg; 0.95 mmol; 3.00 eq.) in DMSO (1.5 ml) was stirred at 120° C. for 24 h. The crude was purified by HPLC to afford the title compound (yield 31%). LC-MS (M+1=433, obsd.=433).

4-Amino-1-(6-amino-5-chloro-pyrimidin-4-yl)-piperidine-4-carboxylic acid [(S)-1-(4-chloro-phenyl)-propyl]-amide ("215")

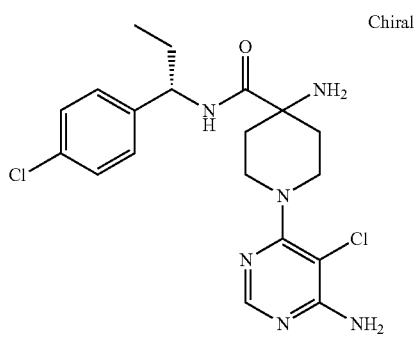 [SMILES: CC[C@H](NC(=O)C1(N)CCN(c2ncnc(N)c2Cl)CC1)c1ccc(Cl)cc1]

The title compound was prepared in an analogous manner as Example (214). LC-MS: (M+1=424, obsd.=424).

4-Amino-1-(6-amino-5-chloro-pyrimidin-4-yl)-piperidine-4-carboxylic acid [(R)-1-(4-chloro-phenyl)-2,2,2-trifluoroethyl]-amide ("216")

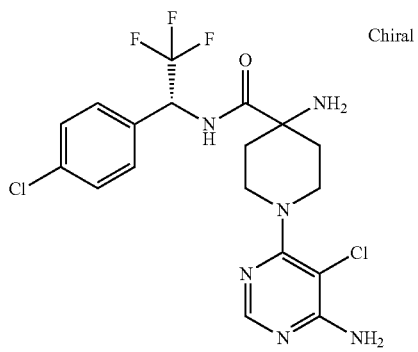 [SMILES: Nc1ncnc(N2CCC(N)(C(=O)N[C@H](c3ccc(Cl)cc3)C(F)(F)F)CC2)c1Cl]

The title compound was prepared in an analogous manner as Example (214). LC-MS: (M+1=464, obsd.=464).

4-Amino-1-(6-amino-5-chloro-pyrimidin-4-yl)-piperidine-4-carboxylic acid [(S)-2-carbamoyl-1-(4-chloro-phenyl)ethyl]-amide ("217")

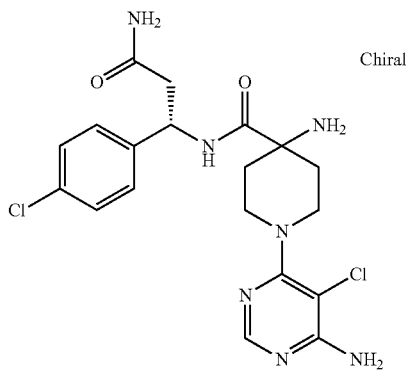 [SMILES: NC(=O)C[C@H](NC(=O)C1(N)CCN(c2ncnc(N)c2Cl)CC1)c1ccc(Cl)cc1]

The title compound was prepared in an analogous manner as Example (214). LC-MS: (M+1=453, obsd.=453).

4-Amino-1-(6-amino-5-cyano-pyrimidin-4-yl)-piperidine-4-carboxylic acid [(S)-1-(4-chloro-phenyl)-ethyl]-amide ("218")

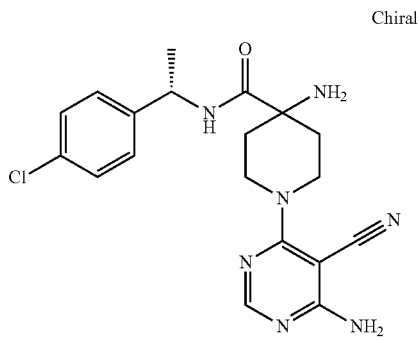 [SMILES: C[C@H](NC(=O)C1(N)CCN(c2ncnc(N)c2C#N)CC1)c1ccc(Cl)cc1]

The title compound was prepared in an analogous manner as Example (214). LC-MS: (M+1=400, obsd.=400).

4-Amino-1-(6-amino-5-cyano-pyrimidin-4-yl)-piperidine-4-carboxylic acid [(S)-1-(4-chloro-phenyl)-propyl]-amide ("219")

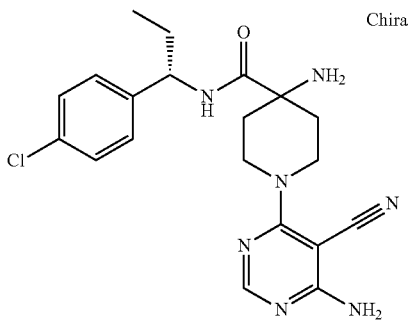 [SMILES: CC[C@H](NC(=O)C1(N)CCN(c2ncnc(N)c2C#N)CC1)c1ccc(Cl)cc1]

The title compound was prepared in an analogous manner as Example (214). LC-MS: (M+1=414, obsd.=414).

4-Amino-1-(6-amino-5-cyano-pyrimidin-4-yl)-piperidine-4-carboxylic acid [(R)-1-(4-chloro-phenyl)-2,2,2-trifluoroethyl]-amide ("220")

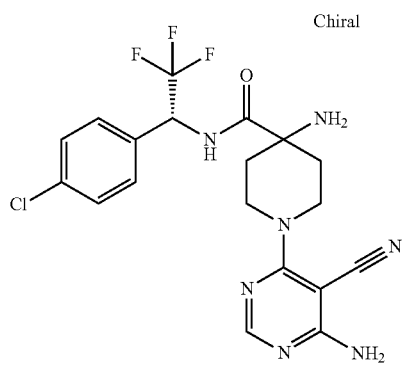 [SMILES: N#Cc1c(N)ncnc1N1CCC(N)(C(=O)N[C@H](c2ccc(Cl)cc2)C(F)(F)F)CC1]

The title compound was prepared in an analogous manner as Example (214). LC-MS: (M+1=454, obsd.=454).

4-Amino-1-(6-amino-5-cyano-pyrimidin-4-yl)-piperidine-4-carboxylic acid [(S)-2-carbamoyl-1-(4-chloro-phenyl)-ethyl]-amide ("221")

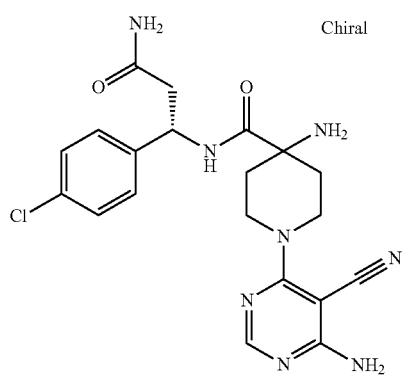 [SMILES: N#Cc1c(N)ncnc1N1CCC(N)(C(=O)N[C@@H](CC(N)=O)c2ccc(Cl)cc2)CC1 ; "Chiral"]

The title compound was prepared in an analogous manner as Example (214). LC-MS: (M+1=443, obsd.=443).

4-Amino-1-(6-amino-5-chloro-pyrimidin-4-yl)-piperidine-4-carboxylic acid [(S)-1-(4-chloro-phenyl)-ethyl]-amide ("222")

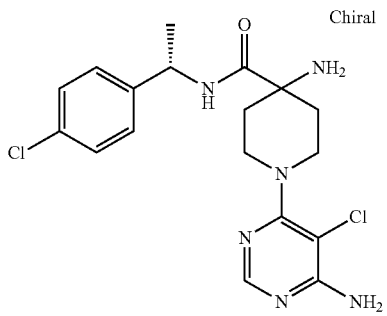 [SMILES: "Chiral" ; C[C@H](NC(=O)C1(N)CCN(c2ncnc(N)c2Cl)CC1)c1ccc(Cl)cc1]

The title compound was prepared in an analogous manner as Example (214). LC-MS: (M+1=410, obsd.=410).

4-Amino-1-(6-amino-5-chloro-pyrimidin-4-yl)-piperidine-4-carboxylic acid [(S)-3-hydroxy-1-(4-trifluoromethyl-phenyl)-propyl]-amide ("223")

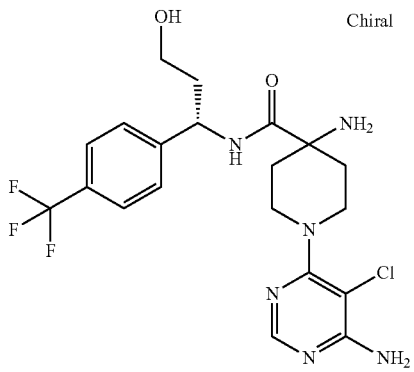 [SMILES: Nc1ncnc(N2CCC(N)(C(=O)N[C@@H](CCO)c3ccc(C(F)(F)F)cc3)CC2)c1Cl ; "Chiral"]

The title compound was prepared in an analogous manner as Example (214). LC-MS: (M+1=473, obsd.=473).

4-Amino-1-[6-amino-5-(1H-pyrazol-4-yl)-pyrimidin-4-yl]-piperidine-4-carboxylic acid [(S)-1-(4-chloro-phenyl)-ethyl]-amide ("224")

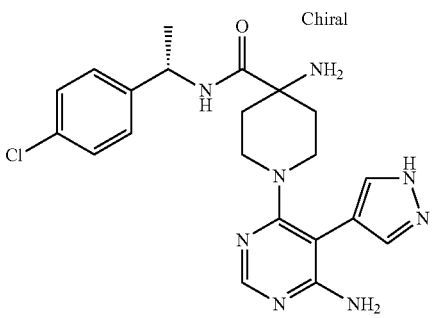

The title compound was prepared in an analogous manner as Example (214). LC-MS: (M+1=441, obsd.=441).

4-Amino-1-[6-amino-5-(1H-pyrazol-4-yl)-pyrimidin-4-yl]-piperidine-4-carboxylic acid [(S)-1-(4-chloro-phenyl)-propyl]-amide ("225")

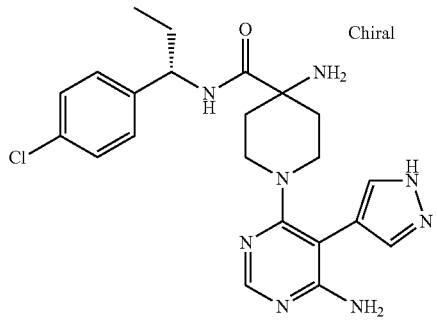 [SMILES: CC[C@H](NC(=O)C1(N)CCN(c2ncnc(N)c2-c2cn[nH]c2)CC1)c1ccc(Cl)cc1 ; "Chiral"]

The title compound was prepared in an analogous manner as Example (214). LC-MS: (M+1=455, obsd.=455).

4-Amino-1-(6-amino-5-cyano-pyrimidin-4-yl)-piperidine-4-carboxylic acid ((S)-3-hydroxy-1-phenyl-propyl)-amide ("226")

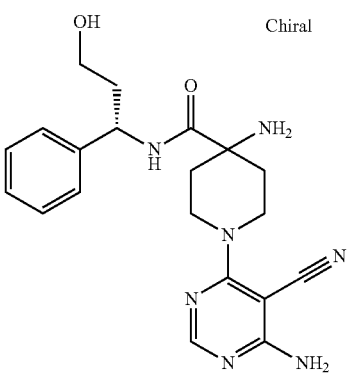 [SMILES: N#Cc1c(N)ncnc1N1CCC(N)(C(=O)N[C@@H](CCO)c2ccccc2)CC1 ; "Chiral"]

The title compound was prepared in an analogous manner as Example (214). LC-MS: (M+1=396, obsd.=396).

145

4-Amino-1-(6-amino-5-cyano-pyrimidin-4-yl)-piperidine-4-carboxylic acid ((S)-3-hydroxy-1-p-tolyl-propyl)-amide ("227")

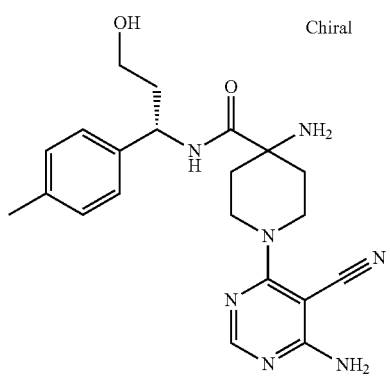 [SMILES: Cc1ccc([C@H](CCO)NC(=O)C2(N)CCN(c3ncnc(N)c3C#N)CC2)cc1 ; "Chiral"]

The title compound was prepared in an analogous manner as Example (214). LC-MS: (M+1=410, obsd.=410).

4-Amino-1-(6-amino-5-chloro-pyrimidin-4-yl)-piperidine-4-carboxylic acid ((S)-3-hydroxy-1-phenyl-propyl)-amide ("228")

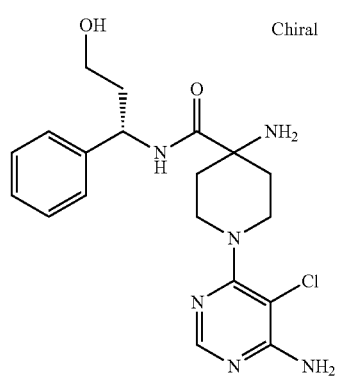 [SMILES: Nc1ncnc(N2CCC(N)(C(=O)N[C@@H](CCO)c3ccccc3)CC2)c1Cl ; "Chiral"]

The title compound was prepared in an analogous manner as Example (214). LC-MS: (M+1=405, obsd.=405).

146

4-Amino-1-(6-amino-5-cyano-pyrimidin-4-yl)-piperidine-4-carboxylic acid [(S)-3-hydroxy-1-(4-methoxy-phenyl)-propyl]-amide ("229")

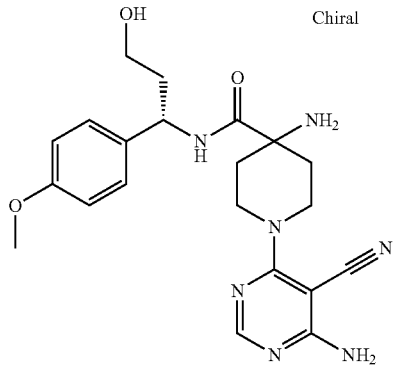 [SMILES: COc1ccc([C@H](CCO)NC(=O)C2(N)CCN(c3ncnc(N)c3C#N)CC2)cc1 ; "Chiral"]

The title compound was prepared in an analogous manner as Example (214). LC-MS: (M+1=426, obsd.=426).

4-Amino-1-(6-amino-5-cyano-pyrimidin-4-yl)-piperidine-4-carboxylic acid [(S)-3-hydroxy-1-(4-trifluoromethyl-phenyl)-propyl]-amide ("230")

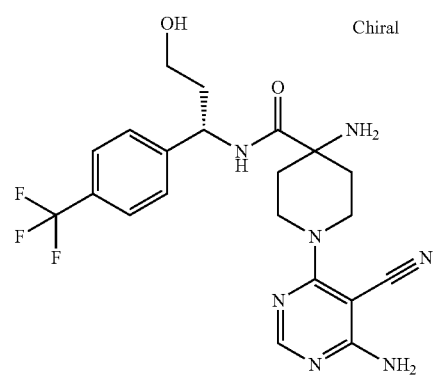 [SMILES: N#Cc1c(N)ncnc1N1CCC(N)(C(=O)N[C@@H](CCO)c2ccc(C(F)(F)F)cc2)CC1 ; "Chiral"]

The title compound was prepared in an analogous manner as Example (214). LC-MS: (M+1=464, obsd.=464).

147

4-Amino-1-(6-amino-5-cyano-pyrimidin-4-yl)-piperidine-4-carboxylic acid ((S)-3-hydroxy-1-pyridin-4-yl-propyl)-amide ("231")

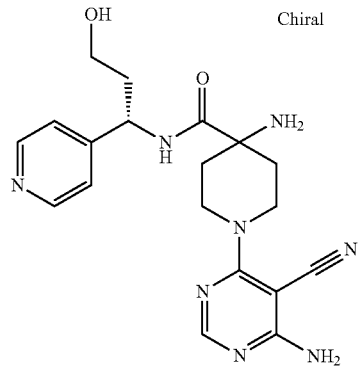 [SMILES: N#Cc1c(N)ncnc1N1CCC(N)(C(=O)N[C@@H](CCO)c2ccncc2)CC1 ; "Chiral"]

The title compound was prepared in an analogous manner as Example (214). LC-MS: (M+1=397, obsd.=397).

4-Amino-6-[4-amino-4-((S)-3-hydroxy-1-p-tolyl-propylcarbamoyl)-piperidin-1-yl]-pyrimidine-5-carboxylic acid amide ("232")

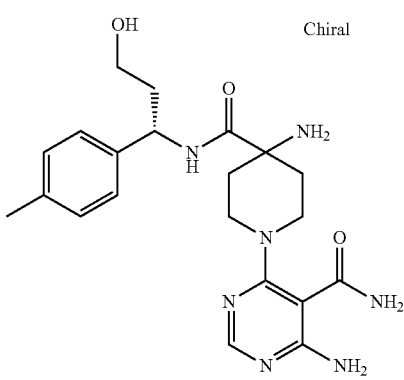 [SMILES: Cc1ccc([C@H](CCO)NC(=O)C2(N)CCN(c3ncnc(N)c3C(N)=O)CC2)cc1 ; "Chiral"]

The title compound was prepared in an analogous manner as Example (214). LC-MS: (M+1=428, obsd.=428).

148

4-Amino-6-{4-amino-4-[(S)-3-hydroxy-1-(4-trifluoromethyl-phenyl)-propylcarbamoyl]-piperidin-1-yl}-pyrimidine-5-carboxylic acid amide ("233")

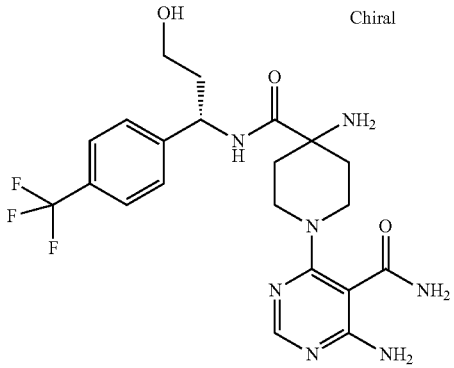 [SMILES: NC(=O)c1c(N)ncnc1N1CCC(N)(C(=O)N[C@@H](CCO)c2ccc(C(F)(F)F)cc2)CC1 ; "Chiral"]

The title compound was prepared in an analogous manner as Example (214). LC-MS: (M+1=482, obsd.=482).

4-Amino-1-(6-amino-5-chloro-pyrimidin-4-yl)-piperidine-4-carboxylic acid [(R)-1-(4-chloro-phenyl)-2-methoxy-ethyl]-amide ("234")

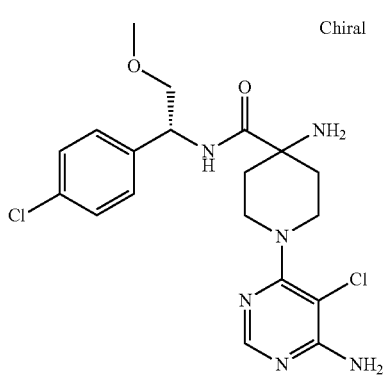 [SMILES: COC[C@H](NC(=O)C1(N)CCN(c2ncnc(N)c2Cl)CC1)c1ccc(Cl)cc1 ; "Chiral"]

The title compound was prepared in an analogous manner as Example (214). LC-MS: (M+1=440, obsd.=440).

4-Amino-1-(6-amino-5-chloro-pyrimidin-4-yl)-piperidine-4-carboxylic acid [(S)-1-(4-chloro-phenyl)-3-hydroxy-propyl]-amide ("235")

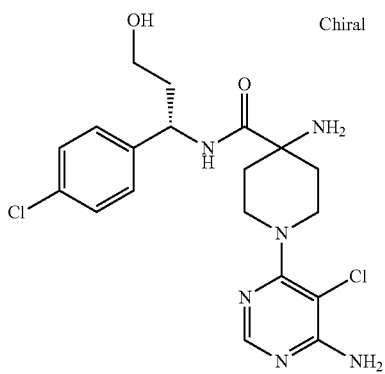 [SMILES: Nc1ncnc(N2CCC(N)(C(=O)N[C@@H](CCO)c3ccc(Cl)cc3)CC2)c1Cl ; "Chiral"]

The title compound was prepared in an analogous manner as Example (214). LC-MS: (M+1=440, obsd.=440).

4-Amino-1-(6-amino-5-chloro-pyrimidin-4-yl)-piperidine-4-carboxylic acid [(S)-1-(4-fluoro-phenyl)-3-hydroxy-propyl]-amide ("236")

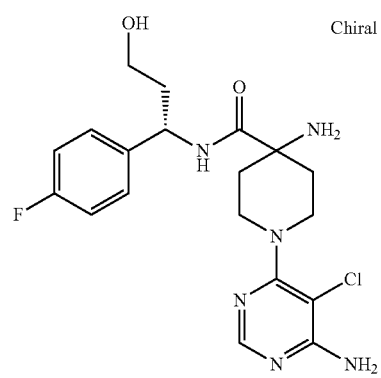 [SMILES: Nc1ncnc(N2CCC(N)(C(=O)N[C@@H](CCO)c3ccc(F)cc3)CC2)c1Cl]

The title compound was prepared in an analogous manner as Example (214). LC-MS: (M+1=423, obsd.=423).

4-Amino-1-(6-amino-5-chloro-pyrimidin-4-yl)-piperidine-4-carboxylic acid ((S)-3-hydroxy-1-p-tolyl-propyl)-amide ("237")

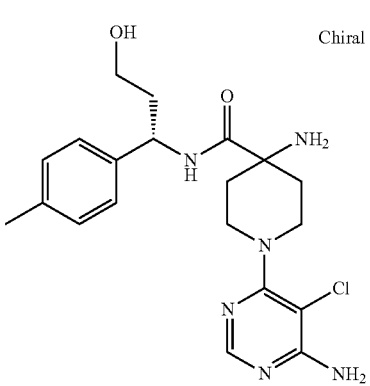 [SMILES: Cc1ccc([C@H](CCO)NC(=O)C2(N)CCN(c3ncnc(N)c3Cl)CC2)cc1]

The title compound was prepared in an analogous manner as Example (214). LC-MS: (M+1=419, obsd.=419).

4-Amino-1-(6-amino-5-chloro-pyrimidin-4-yl)-piperidine-4-carboxylic acid [(S)-3-hydroxy-1-(4-methoxy-phenyl)-propyl]-amide ("238")

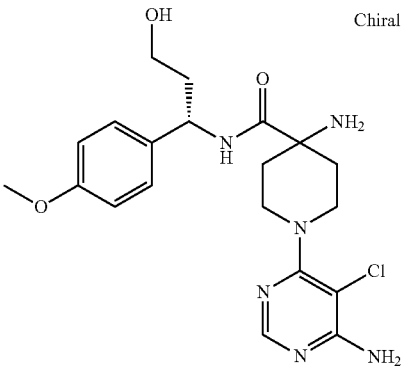 [SMILES: COc1ccc([C@H](CCO)NC(=O)C2(N)CCN(c3ncnc(N)c3Cl)CC2)cc1]

The title compound was prepared in an analogous manner as Example (214). LC-MS: (M+1=435, obsd.=435).

151

4-Amino-1-(6-amino-5-chloro-pyrimidin-4-yl)-piperidine-4-carboxylic acid ((S)-3-hydroxy-1-pyridin-4-yl-propyl)-amide ("239")

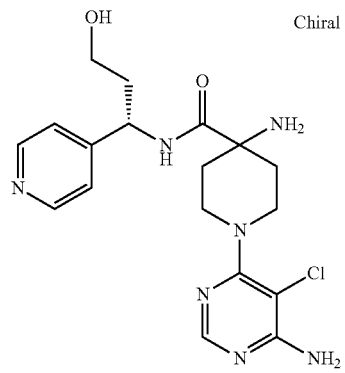 [SMILES: Nc1ncnc(N2CCC(N)(C(=O)N[C@@H](CCO)c3ccncc3)CC2)c1Cl]

The title compound was prepared in an analogous manner as Example (214). LC-MS: (M+1=406, obsd.=406).

4-Amino-1-[6-amino-5-(1H-pyrazol-4-yl)-pyrimidin-4-yl]-piperidine-4-carboxylic acid [(R)-1-(4-chloro-phenyl)-2-methoxy-ethyl]-amide ("240")

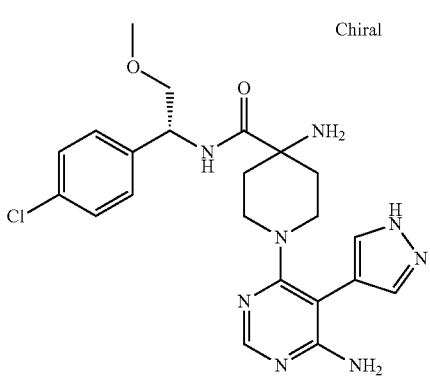 [SMILES: COC[C@H](NC(=O)C1(N)CCN(c2ncnc(N)c2-c2cn[nH]c2)CC1)c1ccc(Cl)cc1]

The title compound was prepared in an analogous manner as Example (214). LC-MS: (M+1=471, obsd.=471).

152

4-Amino-1-(6-amino-5-cyano-pyrimidin-4-yl)-piperidine-4-carboxylic acid [(R)-1-(4-chloro-phenyl)-2-methoxy-ethyl]-amide ("241")

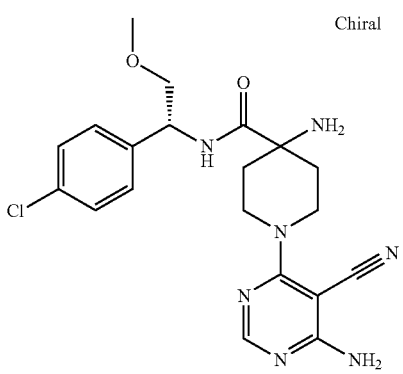 [SMILES: COC[C@H](NC(=O)C1(N)CCN(c2ncnc(N)c2C#N)CC1)c1ccc(Cl)cc1]

The title compound was prepared in an analogous manner as Example (214). LC-MS: (M+1=430, obsd.=430).

4-Amino-1-(6-amino-5-cyano-pyrimidin-4-yl)-piperidine-4-carboxylic acid [(S)-1-(4-chloro-phenyl)-3-hydroxy-propyl]-amide ("242")

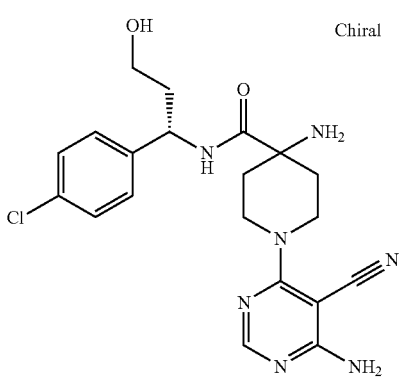 [SMILES: N#Cc1c(N)ncnc1N1CCC(N)(C(=O)N[C@@H](CCO)c2ccc(Cl)cc2)CC1]

The title compound was prepared in an analogous manner as Example (214). LC-MS: (M+1=430, obsd.=430).

153

4-Amino-1-(6-amino-5-cyano-pyrimidin-4-yl)-piperidine-4-carboxylic acid [(S)-1-(4-fluoro-phenyl-3-hydroxy-propyl]-amide ("243")

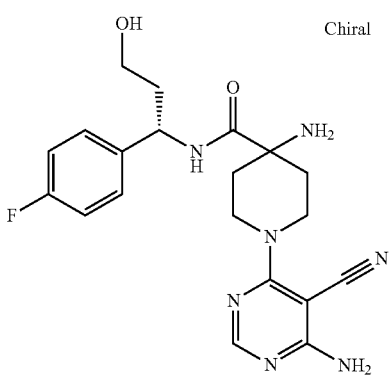 [SMILES: N#Cc1c(N)ncnc1N1CCC(N)(C(=O)N[C@@H](CCO)c2ccc(F)cc2)CC1]

The title compound was prepared in an analogous manner as Example (214). LC-MS: (M+1=414, obsd.=414).

4-Amino-6-{4-amino-4-[(S)-1-(4-chloro-phenyl)-ethylcarbamoyl]-piperidin-1-yl}-pyrimidine-5-carboxylic acid amide ("244")

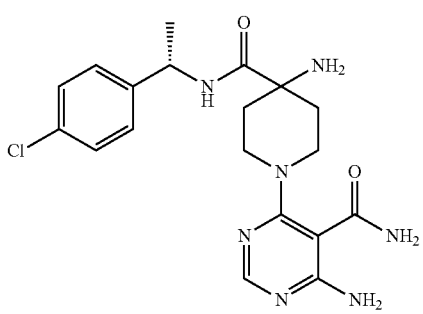

The title compound was prepared in an analogous manner as Example (214). LC-MS: (M+1=418, obsd.=418).

154

4-Amino-6-{4-amino-4-[(S)-1-(4-chloro-phenyl)-propylcarbamoyl]-piperidin-1-yl}-pyrimidine-5-carboxylic acid amide ("245")

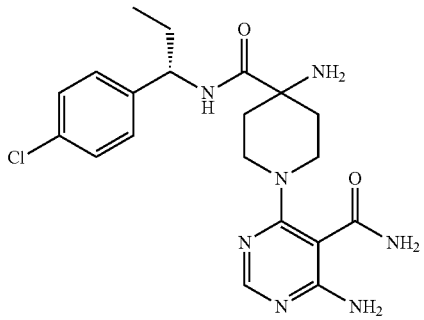

The title compound was prepared in an analogous manner as Example (214). LC-MS: (M+1=432, obsd.=432).

4-Amino-6-{4-amino-4-[(R)-1-(4-chloro-phenyl)-2-methoxy-ethylcarbamoyl]-piperidin-1-yl}-pyrimidine-5-carboxylic acid amide ("246")

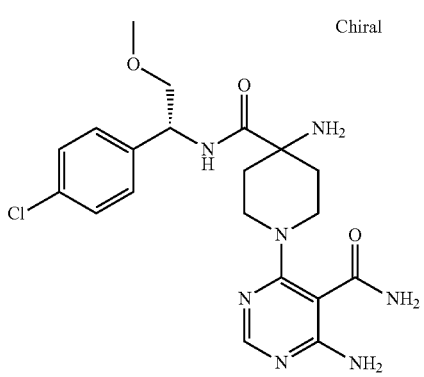 [SMILES: COC[C@H](NC(=O)C1(N)CCN(c2ncnc(N)c2C(N)=O)CC1)c1ccc(Cl)cc1]

The title compound was prepared in an analogous manner as Example (214). LC-MS: (M+1=448, obsd.=448).

4-Amino-1-(6-amino-5-chloro-pyrimidin-4-yl)-piperidine-4-carboxylic acid [(R)-1-(4-chloro-phenyl)-2-methoxy-ethyl]-amide ("247")

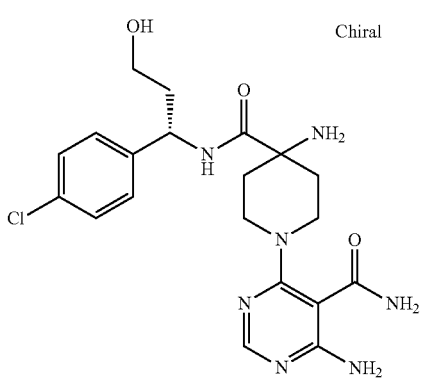 [SMILES: NC(=O)c1c(N)ncnc1N1CCC(N)(C(=O)N[C@@H](CCO)c2ccc(Cl)cc2)CC1]

The title compound was prepared in an analogous manner as Example (214). LC-MS: (M+1=448, obsd.=448).

N-{(R)-3-Amino-1-[6-amino-5-(4-fluoro-phenyl)-pyrimidin-4-yl]-pyrrolidin-3-ylmethyl}-2,4-difluoro-benzamide ("248")

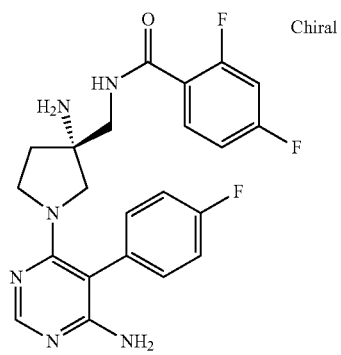 [SMILES: Nc1ncnc(N2CC[C@@](N)(CNC(=O)c3ccc(F)cc3F)C2)c1-c1ccc(F)cc1]

The title compound was isolated by the SFC chiral separation of Example (198). LC-MS: (M+1=443, obsd.=443).

N-{(S)-3-Amino-1-[6-amino-5-(4-fluoro-phenyl)-pyrimidin-4-yl]-pyrrolidin-3-ylmethyl}-2,4-difluoro-benzamide ("249")

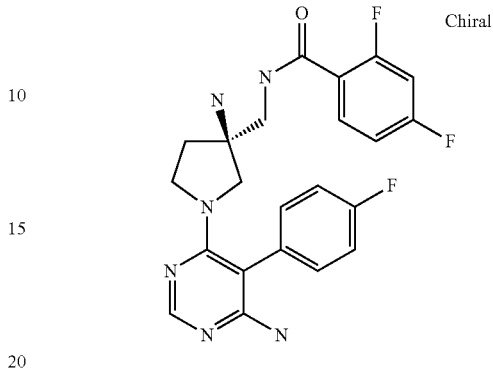

The title compound was isolated by the SFC chiral separation of Example (198). LC-MS: (M+1=443, obsd.=443).

Biological Activity

The $IC_{50}$ values reported for the compounds in the Experimental section were derived from the following protocol for the p70S6K enzyme assay.

P70S6K Enzyme Assay

P70S6K inhibitor compounds were diluted and plated in 96 well plates. A reaction mixture including the following components was then added to the compound plate to initiate the enzyme reaction; P70S6K (3 nM, T412E mutant, Millipore) was mixed with 24 µM ATP in an assay buffer containing 100 mM Hepes (pH 7.5), 5 mM MgCl2, 1 mM DTT, 0.015% Brij and 1 µM of the substrate peptide FITC-AHA-AKRRRLSSLRA-OH (derived from the S6 ribosomal protein sequence, FITC=fluorescein isothiocyanate, AHA=6-aminohexanoic acid). The reaction was incubated for 90 min at 25° C., before the addition of 10 mM EDTA to stop the reaction. The proportion of substrate and product (phosphorylated) peptide was analysed on a Caliper Life Sciences Lab Chip 3000, using a pressure of −1.4 psi, and upstream and downstream voltages of −3000 and −700 respectively. Product peaks were resolved before substrate peaks on the resulting chromatograms.

The values for the p70S6K enzyme inhibition assay for the compounds set out in the Experimental section are presented in Table 4.

TABLE 4

| p70S6K Enzyme Inhibition by Compounds Described by Formula (I) | |
|---|---|
| Compound No. | $IC_{50}$ p70S6K (nM) |
| 1 | 5.8 |
| 2 | 2.2 |
| 3 | 2.6 |
| 4 | 4.5 |
| 5 | 330 |
| 6 | 6.3 |
| 7 | 2.8 |
| 8 | 3.4 |
| 9 | 5.7 |
| 10 | 31 |
| 11 | 280 |
| 12 | 18 |
| 13 | 7.2 |

TABLE 4-continued p70S6K Enzyme Inhibition by Compounds Described by Formula (I)

| Compound No. | IC$_{50}$ p70S6K (nM) |
|---|---|
| 14 | 38 |
| 15 | 4.9 |
| 16 | 4.9 |
| 17 | 1.7 |
| 18 | 18 |
| 19 | 19 |
| 20 | 69 |
| 21 | 35 |
| 22 | 20 |
| 23 | 12 |
| 24 | 5.3 |
| 25 | 3.4 |
| 26 | 45 |
| 27 | 4.2 |
| 28 | 260 |
| 29 | >1000 |
| 30 | 34.5 |
| 31 | 40 |
| 32 | 48.5 |
| 33 | 48.5 |
| 34 | 57 |
| 35 | >1000 |
| 36 | 14 |
| 37 | 5.8 |
| 38 | 100 |
| 39 | 12 |
| 40 | 11 |
| 41 | 14 |
| 42 | 6 |
| 43 | 98 |
| 44 | 150 |
| 45 | 210 |
| 46 | 630 |
| 47 | 960 |
| 48 | 66 |
| 49 | 16 |
| 50 | 450 |
| 51 | 41 |
| 52 | 3.3 |
| 53 | 3.2 |
| 54 | 4.5 |
| 55 | 5.2 |
| 56 | 22 |
| 57 | 4.7 |
| 58 | 31 |
| 59 | 140 |
| 60 | 74 |
| 61 | 33 |
| 62 | 980 |
| 63 | 980 |
| 64 | 50 |
| 65 | 120 |
| 66 | 82 |
| 67 | 24 |
| 68 | >1000 |
| 69 | >1000 |
| 70 | >1000 |
| 71 | >1000 |
| 72 | >1000 |
| 73 | >1000 |
| 74 | 370 |
| 75 | 15 |
| 76 | >1000 |
| 77 | 640 |
| 78 | >1000 |
| 79 | >1000 |
| 80 | 79 |
| 81 | >1000 |
| 82 | 29 |
| 83 | 1000 |
| 84 | 15000 |
| 85 | 2800 |
| 86 | 6400 |
| 87 | 8700 |
| 88 | 6700 |
| 89 | 2700 |
| 90 | 600 |
| 91 | 6300 |
| 92 | 300 |
| 93 | 4300 |
| 94 | 1600 |
| 95 | 3500 |
| 96 | 140 |
| 97 | 3700 |
| 98 | 260 |
| 99 | 670 |
| 100 | 900 |
| 101 | 3800 |
| 102 | 1400 |
| 103 | 920 |
| 104 | 920 |
| 105 | 640 |
| 106 | 320 |
| 107 | 5200 |
| 108 | 3700 |
| 109 | 1900 |
| 110 | 450 |
| 111 | 190 |
| 112 | 460 |
| 113 | >1000 |
| 114 | 3300 |
| 115 | >100000 |
| 116 | 290 |
| 117 | 24000 |
| 118 | 140 |
| 119 | 22000 |
| 120 | 1100 |
| 121 | 900 |
| 122 | 950 |
| 123 | 360 |
| 124 | 3400 |
| 125 | 1200 |
| 126 | 390 |
| 127 | 550 |
| 128 | 280 |
| 129 | 610 |
| 130 | >100000 |
| 131 | 1500 |
| 132 | 1400 |
| 133 | >100000 |
| 134 | 300 |

TABLE 4-continued p70S6K Enzyme Inhibition by Compounds Described by Formula (I)

| Compound No. | IC$_{50}$ p70S6K (nM) |
|---|---|
| 135 | 3600 |
| 136 | — |
| 137 | 3100 |
| 138 | 2.5 |
| 139 | 17 |
| 140 | 4.6 |
| 141 | 1000 |
| 142 | 13 |
| 143 | 27 |
| 144 | 17 |
| 145 | 120 |
| 146 | 11 |
| 147 | 2 |
| 148 | 250 |
| 149 | 460 |
| 150 | 33 |
| 151 | 200 |
| 152 | >1000 |
| 153 | 11 |
| 154 | >1000 |
| 155 | 14 |
| 156 | 130 |
| 157 | 6 |
| 158 | 240 |
| 159 | 4.4 |
| 160 | 590 |
| 161 | 4 |
| 162 | 68 |
| 163 | 1.3 |
| 164 | 44 |
| 165 | 0.9 |
| 166 | 6100 |
| 167 | >1000 |
| 168 | 240 |
| 169 | 4.1 |
| 170 | 12 |
| 171 | 73 |
| 172 | 280 |
| 173 | 110 |
| 174 | 8.5 |
| 175 | 2.6 |
| 176 | 0.8 |
| 177 | 200 |
| 178 | 69 |
| 179 | 13 |
| 180 | 190 |
| 181 | 180 |
| 182 | 220 |
| 183 | 3.4 |
| 184 | >1000 |
| 185 | 60 |
| 186 | 1.4 |
| 187 | 6.1 |
| 188 | >1000 |
| 189 | 140 |
| 190 | 230 |
| 191 | 200 |
| 192 | 13.0 |
| 193 | 31.0 |
| 194 | 9.8 |
| 195 | 3.3 |
| 196 | 50 |
| 197 | 530 |
| 198 | 4.8 |
| 199 | 11 |
| 200 | 120 |
| 201 | 9.5 |
| 202 | 9.1 |
| 203 | 5.3 |
| 204 | 2.6 |
| 205 | 25 |
| 206 | 1000 |
| 207 | 150 |
| 208 | 46 |
| 209 | — |
| 210 | — |
| 211 | — |
| 212 | — |
| 213 | — |
| 214 | 450 |
| 215 | 190 |
| 216 | 820 |
| 217 | 820 |
| 218 | 200 |
| 219 | 140 |
| 220 | 3200 |
| 221 | 140 |
| 222 | 620 |
| 223 | 22000 |
| 224 | 87 |
| 225 | 78 |
| 226 | 820 |
| 227 | 280 |
| 228 | 2800 |
| 229 | 450 |
| 230 | 18000 |
| 231 | 3600 |
| 232 | 23000 |
| 233 | 41000 |
| 234 | 560 |
| 235 | 250 |
| 236 | 900 |
| 237 | 860 |
| 238 | 380 |
| 239 | 7200 |
| 240 | 100 |
| 241 | 210 |
| 242 | 98 |
| 243 | 390 |
| 244 | 20000 |
| 245 | 2400 |
| 246 | 5000 |
| 247 | 3600 |
| 248 | 290 |
| 249 | 5.9 |

The invention claimed is:

1. A compound of Formula (I)

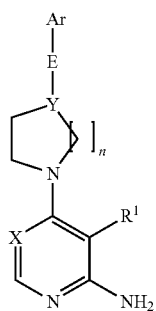

(I)

or a pharmaceutically acceptable salt, solvate, or solvate of salt thereof, wherein:
X is N or CH;
Y is N;
E is

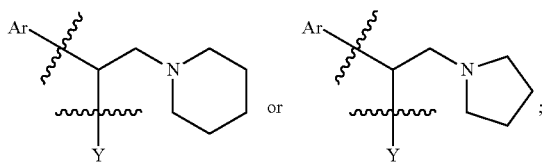

$R^1$ is H,
Hal is F, Cl, Br or I;
each LA is independently an unbranched or branched, linear saturated or partially unsaturated hydrocarbon chain having 1, 2, 3 4, 5 or 6 C atoms, wherein 1, 2 or 3 H atoms may be replaced by Hal or OH;
each Ar is independently a mono- or bicyclic aromatic homo- or heterocycle having 0, 1, 2, 3 or 4 N, O and/or S atoms and 5, 6, 7, 8, 9, or 10 skeleton atoms, which may be unsubstituted or, independently of one another, mono- or disubstituted by Hal, LA, OH, SH, O(LA), $NH_2$, NH(LA), $N(LA)_2$, $NO_2$, CN, OCN, COOH, COO(LA), $CONH_2$, CONH(LA), $CON(LA)_2$, NHCO(LA), NHCONH(LA), $NHCONH_2$, CHO and CO(LA), and/or monosubstituted by $Cyc^2$ or O-$Cyc^2$;
each $Cyc^1$ is independently a 3, 4, 5 or 6 membered monocyclic aliphatic homo- or heterocycle having 0-2 heteroatoms, selected from O, S and N, which may be mono- or disubstituted by Hal, LA, $NH_2$, NH(LA), $N(LA)_2$, HO(LA)-;

each $Cyc^2$ is independently a 5 or 6 membered monocyclic aromatic homo- or heterocycle having 0-3 heteroatoms, selected from O, S and N, which may be mono- or di-substituted by Hal or LA; and
n is 1 or 2.

2. The compound according to claim 1 wherein
X is N,
or a pharmaceutically acceptable salt, solvate, or solvate of salt thereof.

3. The compound according to claim 1, selected from:
6-{4-[1-(3-trifluoromethyl-phenyl)-2-piperidin-1-yl-ethyl]-piperazin-1-yl}-pyrimidin-4-ylamine ("71");
6-{4-[1-(3-trifluoromethyl-phenyl)-2-pyrrolidin-1-yl-ethyl]-piperazin-1-yl}-pyrimidin-4-ylamine ("73");
6-{4-[1-(3-fluorophenyl)-2-piperidin-1-yl-ethyl]-piperazin-1-yl}-pyrimidin-4-ylamine ("76");
6-{4-[1-(4-fluorophenyl)-2-pyrrolidin-1-yl-ethyl]-piperazin-1-yl}-pyrimidin-4-ylamine ("78"); and
6-{4-[1-(4-fluoro-phenyl)-2-piperidin-1-yl-ethyl]-piperazin-1-yl}-pyrimidin-4-ylamine ("79");
or a pharmaceutically acceptable salt, solvate, or solvate of salt thereof.

4. A pharmaceutical composition comprising a compound according to claim 1, or a pharmaceutically acceptable salt, solvate, or solvate of salt thereof, as active ingredient, together with a pharmaceutically acceptable carrier.

5. A method for treating cancer, comprising administering to a subject a compound of claim 1, or a pharmaceutically acceptable salt, solvate, or solvate of salt thereof.

6. W The method of claim 5, wherein said cancer is selected from the group consisting of brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma and Kaposi's sarcoma.

7. A kit consisting of separate packs of
a) an effective amount of a compound according to claim 1, or a pharmaceutically acceptable salt, solvate, or solvate of salt thereof, and
b) an effective amount of a further medicament active ingredient.

8. The compound according to claim 1, wherein Ar is phenyl or pyridyl, which is unsubstituted or mono- or disubstituted by Hal, LA or O(LA), or a pharmaceutically acceptable salt, solvate, or solvate of salt, thereof.

9. The compound according to claim 1, wherein
X is N,
Ar is phenyl or pyridyl, which is unsubstituted or mono- or disubstituted by Hal, LA or O(LA),
or a pharmaceutically acceptable salt, solvate, or solvate of salt thereof.

10. A compound selected from:
6-{4-[2-Amino-1-(4-trifluoromethyl-phenyl)-ethyl]-piperazin-1-yl}-5-bromo-pyrimidin-4-ylamine ("1")
6-{4-[2-Amino-1-(4-trifluoromethyl-phenyl)-ethyl]-piperazin-1-yl}-5-(4-fluoro-phenyl)-pyrimidin-4-ylamine ("2")
6-{4-[(R)-2-Amino-1-(4-trifluoromethyl-phenyl)-ethyl]-piperazin-1-yl}-5-(4-fluoro-phenyl)-pyrimidin-4-ylamine ("4")
6-[4-(2-Amino-1-phenyl-ethyl)-piperazin-1-yl]-5-bromo-pyrimidin-4-ylamine ("5")
6-[4-(2-Amino-1-phenyl-ethyl)-piperazin-1-yl]-5-(4-fluoro-phenyl)-pyrimidin-4-ylamine ("6")
6-{4-[2-Amino-1-(4-trifluoromethyl-phenyl)-ethyl]-piperazin-1-yl}-5-(1H-pyrazol-4-yl)-pyrimidin-4-ylamine ("7")
(R)-6-(4-(2-amino-1-(4-(trifluoromethyl)phenyl)ethyl)piperazin-1-yl)-5-(1H-pyrazol-4-yl)pyrimidin-4-amine ("9"),
5-(4-fluorophenyl)-6-(4-(2-(pyrrolidin-1-yl)-1-(4-(trifluoromethyl)-phenyl)-ethyl)-piperazin-1-yl)-pyrimidin-4-amine ("10")
5-bromo-6-(4-(2-(piperidin-1-yl)-1-(4-(trifluoromethyl)phenyl)ethyl)piperazin-1-yl)pyrimidin-4-amine ("11")
5-(4-Fluoro-phenyl)-6-{4-[2-piperidin-1-yl-1-(4-trifluoromethyl-phenyl)-ethyl]-piperazin-1-yl}-pyrimidin-4-ylamine ("12")
5-(4-Fluoro-phenyl)-6-[4-(4-trifluoromethyl-benzyl)-piperazin-1-yl]-pyrimidin-4-ylamine ("13")
5-bromo-6-(4-(2-(dimethylamino)-1-(4-(trifluoromethyl)phenyl)ethyl)piperazin-1-yl)pyrimidin-4-amine ("14")
(S)-6-(4-(2-(dimethylamino)-1-(4-(trifluoromethyl)phenyl)ethyl)piperazin-1-yl)-5-(4-fluorophenyl)pyrimidin-4-amine ("16")
(R)-6-(4-(2-(dimethylamino)-1-(4-(trifluoromethyl)phenyl)ethyl)piperazin-1-yl)-5-(4-fluorophenyl)pyrimidin-4-amine ("17")
5-(6-aminopyridin-3-yl)-6-(4-(2-(dimethylamino)-1-(4-(trifluoromethyl)-phenyl)ethyl)piperazin-1-yl)pyrimidin-4-amine ("20")
6-(4-(2-(dimethylamino)-1-(4-(trifluoromethyl)phenyl)ethyl)piperazin-1-yl)-5-vinylpyrimidin-4-amine ("21")
2-(4-(4-amino-6-(4-(2-(dimethylamino)-1-(4-(trifluoromethyl)phenyl)ethyl)-piperazin-1-yl)pyrimidin-5-yl)phenyl)propan-2-ol ("22")
Methyl 4-(4-amino-6-(4-(2-(dimethylamino)-1-(4-(trifluoromethyl)phenyl)ethyl) piperazin-1-yl)pyrimidin-5-yl)benzoate ("23")
6-(4-(2-amino-1-(4-(trifluoromethyl)phenyl)ethyl)piperazin-1-yl)-5-(cyclohex-1-en-1-yl)pyrimidin-4-amine ("24")
6-(4-(2-amino-1-(4-(trifluoromethyl)phenyl)ethyl)piperazin-1-yl)-5-(cyclopent-1-en-1-yl)pyrimidin-4-amine ("25")
4-(4-amino-6-(4-(2-(dimethylamino)-1-(4-(trifluoromethyl)phenyl)ethyl)piperazin-1-yl)pyrimidin-5-yl)benzoic acid ("26")
5-Cyclopropyl-6-(4-(2-(dimethylamino)-1-(4-(trifluoromethyl)phenyl)ethyl)piperazin-1-yl)pyrimidin-4-amine ("28")
5-Bromo-6-{4-[(1-methyl-1H-imidazol-2-yl)-phenyl-methyl]-piperazin-1-yl}-pyrimidin-4-ylamine ("29")
5-(4-Fluoro-phenyl)-6-{4-[(1-methyl-1H-imidazol-2-yl)-phenyl-methyl]-piperazin-1-yl}-pyrimidin-4-ylamine ("30")
6-(4-(2-amino-1-(4-(trifluoromethyl)phenyl)ethyl)piperazin-1-yl)-5-methoxypyrimidin-4-amine ("31")
6-(4-(2-amino-1-(4-(trifluoromethyl)phenyl)ethyl)piperazin-1-yl)-5-(2,2,2-trifluoroethoxy)pyrimidin-4-amine ("33")
6-(4-(2-amino-1-(4-(trifluoromethyl)phenyl)ethyl)piperazin-1-yl)-5-(benzyloxy)pyrimidin-4-amine ("34")
(35) 4-amino-6-(4-(2-amino-1-(4-(trifluoromethyl)phenyl)ethyl)piperazin-1-yl) pyrimidin-5-ol ("35")
4-Amino-6-{4-[2-amino-1-(4-trifluoromethyl-phenyl)-ethyl]-piperazin-1-yl}-pyrimidine-5-carbonitrile ("36")
6-(4-(2-amino-1-(4-(trifluoromethyl)phenyl)ethyl)piperazin-1-yl)-5-(1H-pyrrol-3-yl)pyrimidin-4-amine ("37")
6-(4-(2-amino-1-(4-(trifluoromethyl)phenyl)ethyl)piperazin-1-yl)-5-(isoxazol-4-yl)pyrimidin-4-amine ("38")
6-(4-(2-amino-1-(4-(trifluoromethyl)phenyl)ethyl)piperazin-1-yl)-5-(1-ethyl-1H-pyrazol-4-yl)pyrimidin-4-amine ("39")
6-{4-[2-Amino-1-(4-trifluoromethyl-phenyl)-ethyl]-piperazin-1-yl}-5-(1-methyl-1H-pyrazol-4-yl)-pyrimidin-4-ylamine ("40")
6-{4-[(S)-2-Amino-1-(4-trifluoromethyl-phenyl)-ethyl]-piperazin-1-yl}-5-(1-methyl-1H-pyrazol-4-yl)-pyrimidin-4-ylamine ("41")
6-{4-[(R)-2-Amino-1-(4-trifluoromethyl-phenyl)-ethyl]-piperazin-1-yl}-5-(1-methyl-1H-pyrazol-4-yl)-pyrimidin-4-ylamine ("42")
6-{4-[2-Amino-1-(4-trifluoromethyl-phenyl)-ethyl]-piperazin-1-yl}-5-(1-methyl-1H-pyrazol-3-yl)-pyrimidin-4-ylamine ("43")
3-[2-{4-[6-Amino-5-(1-methyl-1H-pyrazol-3-yl)-pyrimidin-4-yl]-piperazin-1-yl}-2-(4-trifluoromethyl-phenyl)-ethylamino]-2,3-dimethyl-butan-2-ol ("44")
6-(4-(2-amino-1-(4-(trifluoromethyl)phenyl)ethyl)piperazin-1-yl)-5-((3-fluoroazetidin-1-yl)methyl)pyrimidin-4-amine ("45")
5-Bromo-6{4-(4-chlorobenzyl)-piperidin-1-yl}pyrimidin-4-amine ("46")
5-Bromo-6{4-(4-trifluoromethylbenzyl)-piperidin-1-yl}pyrimidin-4-amine ("47")
5-(4-Fluorophenyl)-6{4-(4-trifluoromethylbenzyl)-piperidin-1-yl}pyrimidin-4-amine ("48")
5-(4-Fluorophenyl)-6{4-(4-chlorobenzyl)-piperidin-1-yl}pyrimidin-4-amine ("49")
5-(4-Fluorophenyl)-6{4-(4-(4-fluorophenyl)benzyl)-piperidin-1-yl}pyrimidin-4-amine ("50")
6-{4-[2-Amino-1-(4-trifluoromethyl-phenyl)-ethyl]-piperidin-1-yl}-5-bromo-pyrimidin-4-ylamine ("51")
6-{4-[2-Amino-1-(4-trifluoromethyl-phenyl)-ethyl]-piperidin-1-yl}-5-(4-fluoro-phenyl)-pyrimidin-4-ylamine ("52")
6-{4-[(R)-2-Amino-1-(4-trifluoromethyl-phenyl)-ethyl]-piperidin-1-yl}-5-(4-fluoro-phenyl)-pyrimidin-4-ylamine ("54")
(S)-6-(4-(2-amino-1-(4-(trifluoromethyl)phenyl)ethyl)piperidin-1-yl)-5-(1H-pyrazol-4-yl)pyrimidin-4-amine ("56")
(R)-6-(4-(2-amino-1-(4-(trifluoromethyl)phenyl)ethyl)piperidin-1-yl)-5-(1H-pyrazol-4-yl)pyrimidin-4-amine ("57")

6-(4-(2-amino-1-(4-(trifluoromethyl)phenyl)ethyl)piperidin-1-yl)-5-(1-methyl-1H-pyrazol-4-yl)pyrimidin-4-amine ("58")
6-(4-(2-amino-1-(4-(trifluoromethyl)phenyl)ethyl)piperidin-1-yl)-5-(isoxazol-4-yl)pyrimidin-4-amine ("59")
2-((4-(6-amino-5-(4-fluorophenyl)pyrimidin-4-yl)piperazin-1-yl)methyl)-4,5-dichlorophenol ("60")
2-(1-(4-(6-amino-5-(4-fluorophenyl)pyrimidin-4-yl)piperazin-1-yl)ethyl)-5-chlorophenol ("61")
6-(4-(2-(azetidin-3-yloxy)-4,5-dichlorobenzyl)piperazin-1-yl)-5-(4-fluorophenyl)pyrimidin-4-amine ("62")
6-(4-{1-[2-(Azetidin-3-yloxy)-4-chloro-phenyl]-ethyl}-piperazin-1-yl)-5-(4-fluoro-phenyl)-pyrimidin-4-ylamine ("63")
5-(4-Fluorophenyl)-6{4-[1-(3-fluoro-phenyl)-2-piperidin-1-yl-ethyl]-piperazin-1-yl}-pyrimidin-4-ylamine ("64")
5-(4-Fluorophenyl)-6{4-[1-(3-trifluoro-phenyl)-2-piperidin-1-yl-ethyl]-piperazin-1-yl}-pyrimidin-4-ylamine ("65")
5-(4-Fluorophenyl)-6{4-[1-(3-trifluoromethyl-phenyl)-2-pyrrolidin-1-yl-ethyl]-piperazin-1-yl}-pyrimidin-4-ylamine ("66")
5-(4-Fluorophenyl)-6{4-[1-(4-fluoro-phenyl)-2-piperidin-1-yl-ethyl]-piperazin-1-yl}-pyrimidin-4-ylamine ("67")
5-Bromo-6{4-[1-(3-fluoro-phenyl)-2-piperidin-1-yl-ethyl]-piperazin-1-yl}-pyrimidin-4-ylamine ("68")
5-Bromo-6{4-[1-(3-trifluoromethyl-phenyl)-2-pyrrolidin-1-yl-ethyl]-piperazin-1-yl}-pyrimidin-4-ylamine ("69")
5-Bromo-6{4-[1-(3-trifluoromethyl-phenyl)-2-piperidin-1-yl-ethyl]-piperazin-1-yl}-pyrimidin-4-ylamine ("70")
6-{4-[1-(3-trifluoromethyl-phenyl)-2-piperidin-1-yl-ethyl]-piperazin-1-yl}-pyrimidin-4-ylamine ("71")
5-Bromo-6{4-[1-(4-fluoro-phenyl)-2-piperidin-1-yl-ethyl]-piperazin-1-yl}-pyrimidin-4-ylamine ("72")
6-{4-[1-(3-trifluoromethyl-phenyl)-2-pyrrolidin-1-yl-ethyl]-piperazin-1-yl}-pyrimidin-4-ylamine ("73")
6-{4-[2-Amino-1-(4-trifluoromethyl-phenyl)-ethyl]-piperazin-1-yl}-5-fluoro-pyrimidin-4-ylamine ("74")
5-(4-Fluorophenyl)-6{4-[1-(4-fluorophenyl)-2-pyrrolidin-1-yl-ethyl]-piperazin-1-yl}-pyrimidin-4-ylamine ("75")
6-{4-[1-(3-fluorophenyl)-2-piperidin-1-yl-ethyl]-piperazin-1-yl}-pyrimidin-4-ylamine ("76")
5-Bromo-6{4-[1-(4-fluorophenyl)-2-pyrrolidin-1-yl-ethyl]-piperazin-1-yl}-pyrimidin-4-ylamine ("77")
6-{4-[1-(4-fluorophenyl)-2-pyrrolidin-1-yl-ethyl]-piperazin-1-yl}-pyrimidin-4-ylamine ("78")
6-{4-[1-(4-fluoro-phenyl)-2-piperidin-1-yl-ethyl]-piperazin-1-yl}-pyrimidin-4-ylamine ("79")
5-Chloro-6{4-[1-(4-fluorophenyl)-2-pyrrolidin-1-yl-ethyl]-piperazin-1-yl}-pyrimidin-4-ylamine ("81")
(R)5-(4-Fluorophenyl)-6{4-[1-(4-fluorophenyl)-2-pyrrolidin-1-yl-ethyl]-piperazin-1-yl}-pyrimidin-4-ylamine ("82")
(S)-5-(4-Fluorophenyl)-6{4-[1-(4-fluorophenyl)-2-pyrrolidin-1-yl-ethyl]-piperazin-1-yl}-pyrimidin-4-ylamine ("83")
6-{4-[2-Azetidin-1-yl-1-(3-fluoro-phenyl)-ethyl]-piperazin-1-yl}-5-(1H-pyrazol-4-yl)-pyrimidin-4-ylamine ("84")
4-(1-{4-[6-Amino-5-(1H-pyrazol-4-yl)-pyrimidin-4-yl]-piperazin-1-yl}-2-azetidin-1-yl-ethyl)-benzonitrile ("85")
4-(1-{4-[6-Amino-5-(1H-pyrazol-4-yl)-pyrimidin-4-yl]-piperazin-1-yl}-2-azetidin-1-yl-ethyl)-benzoic acid methyl ester ("86")
6-{4-[(S)-2-Azetidin-1-yl-1-(3-fluoro-phenyl)-ethyl]-piperazin-1-yl}-5-(1H-pyrazol-4-yl)-pyrimidin-4-ylamine ("87")
4-((S)-1-{4-[6-Amino-5-(1H-pyrazol-4-yl)-pyrimidin-4-yl]-piperazin-1-yl}-2-azetidin-1-yl-ethyl)-benzonitrile ("88")
4-((S)-1-{4-[6-Amino-5-(1H-pyrazol-4-yl)-pyrimidin-4-yl]-piperazin-1-yl}-2-azetidin-1-yl-ethyl)-benzoic acid methyl ester ("89")
6-{4-[2-Azetidin-1-yl-1-(3-fluoro-phenyl)-ethyl]-piperazin-1-yl}-5-(4-fluoro-phenyl)-pyrimidin-4-ylamine ("90")
3-((R)-1-{4-[6-Amino-5-(1H-pyrazol-4-yl)-pyrimidin-4-yl]-piperazin-1-yl}-2-azetidin-1-yl-ethyl)-benzonitrile ("91")
6-{4-[2-Azetidin-1-yl-1-(3-fluoro-4-methoxy-phenyl)-ethyl]-piperazin-1-yl}-5-(4-fluoro-phenyl)-pyrimidin-4-ylamine ("92")
6-{4-[(R)-2-Azetidin-1-yl-1-(4-methanesulfonyl-phenyl)-ethyl]-piperazin-1-yl}-5-(1H-pyrazol-4-yl)-pyrimidin-4-ylamine ("93")
6-{4-[(R)-2-Azetidin-1-yl-1-(2,3-dihydro-benzo[1,4]dioxin-6-yl)-ethyl]-piperazin-1-yl}-5-(4-fluoro-phenyl)-pyrimidin-4-ylamine ("94")
6-{4-[2-Azetidin-1-yl-1-(3-fluoro-4-methoxy-phenyl)-ethyl]-piperazin-1-yl}-5-(1H-pyrazol-4-yl)-pyrimidin-4-ylamine ("95")
4-(1-{4-[6-Amino-5-(4-fluoro-phenyl)-pyrimidin-4-yl]-piperazin-1-yl}-2-azetidin-1-yl-ethyl)-benzoic acid methyl ester ("96")
3-((S)-1-{4-[6-Amino-5-(1H-pyrazol-4-yl)-pyrimidin-4-yl]-piperazin-1-yl}-2-azetidin-1-yl-ethyl)-benzonitrile ("97")
6-{4-[(S)-2-Azetidin-1-yl-1-(2,3-dihydro-benzo[1,4]dioxin-6-yl)-ethyl]-piperazin-1-yl}-5-(4-fluoro-phenyl)-pyrimidin-4-ylamine ("98")
6-{4-[2-Azetidin-1-yl-1-(2-fluoro-3-trifluoromethyl-phenyl)-ethyl]-piperazin-1-yl}-5-(1H-pyrazol-4-yl)-pyrimidin-4-ylamine ("99")
6-{4-[2-Azetidin-1-yl-1-(2,3-difluoro-4-methyl-phenyl)-ethyl]-piperazin-1-yl}-5-(1H-pyrazol-4-yl)-pyrimidin-4-ylamine ("100")
6-{4-[2-Azetidin-1-yl-1-(4-fluoro-3-trifluoromethyl-phenyl)-ethyl]-piperazin-1-yl}-5-(1H-pyrazol-4-yl)-pyrimidin-4-ylamine ("101")
6-{4-[(S)-2-Azetidin-1-yl-1-(3-fluoro-phenyl)-ethyl]-piperazin-1-yl}-5-(4-fluoro-phenyl)-pyrimidin-4-ylamine ("102")
6-{4-[(R)-2-Azetidin-1-yl-1-(3-fluoro-phenyl)-ethyl]-piperazin-1-yl}-5-(4-fluoro-phenyl)-pyrimidin-4-ylamine ("103")
6-{4-[(R)-2-Azetidin-1-yl-1-(3-fluoro-4-methoxy-phenyl)-ethyl]-piperazin-1-yl}-5-(4-fluoro-phenyl)-pyrimidin-4-ylamine ("104")
6-{4-[(S)-2-Azetidin-1-yl-1-(3-fluoro-4-methoxy-phenyl)-ethyl]-piperazin-1-yl}-5-(4-fluoro-phenyl)-pyrimidin-4-ylamine ("105")
4-(1-{4-[6-Amino-5-(4-fluoro-phenyl)-pyrimidin-4-yl]-piperazin-1-yl}-2-azetidin-1-yl-ethyl)-benzonitrile ("106")
6-{4-[(R)-2-Azetidin-1-yl-1-(2,3-dihydro-benzo[1,4]dioxin-6-yl)-ethyl]-piperazin-1-yl}-5-(1H-pyrazol-4-yl)-pyrimidin-4-ylamine ("107")

6-{4-[(S)-2-Azetidin-1-yl-1-(2,3-dihydro-benzo[1,4]di-oxin-6-yl)-ethyl]-piperazin-1-yl}-5-(1H-pyrazol-4-yl)-pyrimidin-4-ylamine ("108")

6-{4-[2-Azetidin-1-yl-1-(4-chloro-3-methyl-phenyl)-ethyl]-piperazin-1-yl}-5-(1H-pyrazol-4-yl)-pyrimidin-4-ylamine ("109")

4-((S)-1-{4-[6-Amino-5-(4-fluoro-phenyl)-pyrimidin-4-yl]-piperazin-1-yl}-2-azetidin-1-yl-ethyl)-benzoic acid methyl ester ("110")

4-((R)-1-{4-[6-Amino-5-(4-fluoro-phenyl)-pyrimidin-4-yl]-piperazin-1-yl}-2-azetidin-1-yl-ethyl)-benzoic acid methyl ester ("111")

6-{4-[4-Azetidin-1-yl-1-(4-chloro-phenyl)-butyl]-piperazin-1-yl}-5-(4-fluoro-phenyl)-pyrimidin-4-ylamine ("113")

6-{4-[2-Azetidin-1-yl-1-(4-fluoro-3-trifluoromethoxy-phenyl)-ethyl]-piperazin-1-yl}-5-(1H-pyrazol-4-yl)-pyrimidin-4-ylamine ("114")

6-{4-[2-Azetidin-1-yl-1-(5,6,7,8-tetrahydro-naphthalen-2-yl)-ethyl]-piperazin-1-yl}-5-(6-piperazin-1-yl-pyridin-3-yl)-pyrimidin-4-ylamine ("115")

6-{4-[2-Azetidin-1-yl-1-(4-imidazol-1-yl-phenyl)-ethyl]-piperazin-1-yl}-5-(4-fluoro-phenyl)-pyrimidin-4-ylamine ("116")

[4-(4-Amino-6-{4-[2-azetidin-1-yl-1-(3,4-dichloro-phenyl)-ethyl]-piperazin-1-yl}-pyrimidin-5-yl)-pyrazol-1-yl]-acetic acid ethyl ester ("117")

6-(1-{4-[6-Amino-5-(4-fluoro-phenyl)-pyrimidin-4-yl]-piperazin-1-yl}-2-azetidin-1-yl-ethyl)-3H-benzothiazol-2-one ("118")

[4-(4-Amino-6-{4-[2-azetidin-1-yl-1-(5,6,7,8-tetrahydro-naphthalen-2-yl)-ethyl]-piperazin-1-yl}-pyrimidin-5-yl)-pyrazol-1-yl]-acetic acid ethyl ester ("119")

6-{4-[2-Azetidin-1-yl-1-(2-fluoro-4-trifluoromethyl-phenyl)-ethyl]-piperazin-1-yl}-5-(1H-pyrazol-4-yl)-pyrimidin-4-ylamine ("120")

6-{4-[2-Azetidin-1-yl-1-(4-chloro-3-fluoro-phenyl)-ethyl]-piperazin-1-yl}-5-(1H-pyrazol-4-yl)-pyrimidin-4-ylamine ("121")

6-{4-[2-Azetidin-1-yl-1-(5,6,7,8-tetrahydro-naphthalen-2-yl)-ethyl]-piperazin-1-yl}-5-(1H-pyrazol-4-yl)-pyrimidin-4-ylamine ("122")

6-{4-[2-Azetidin-1-yl-1-(5,6,7,8-tetrahydro-naphthalen-2-yl)-ethyl]-piperazin-1-yl}-5-(4-fluoro-phenyl)-pyrimidin-4-ylamine ("123")

6-{4-[2-Azetidin-1-yl-1-(2,3-difluoro-phenyl)-ethyl]-piperazin-1-yl}-5-(1H-pyrazol-4-yl)-pyrimidin-4-ylamine ("124")

3-((S)-1-{4-[6-Amino-5-(4-fluoro-phenyl)-pyrimidin-4-yl]-piperazin-1-yl}-2-azetidin-1-yl-ethyl)-benzonitrile ("125")

6-{4-[2-Azetidin-1-yl-1-(2,3-dichloro-phenyl)-ethyl]-piperazin-1-yl}-5-(1H-pyrazol-4-yl)-pyrimidin-4-ylamine ("126")

6-{4-[2-Azetidin-1-yl-1-(3-fluoro-4-trifluoromethyl-phenyl)-ethyl]-piperazin-1-yl}-5-(1H-pyrazol-4-yl)-pyrimidin-4-ylamine ("127")

6-{4-[2-Azetidin-1-yl-1-(4-methanesulfonyl-phenyl)-ethyl]-piperazin-1-yl}-5-(4-fluoro-phenyl)-pyrimidin-4-ylamine ("128")

3-((R)-1-{4-[6-Amino-5-(4-fluoro-phenyl)-pyrimidin-4-yl]-piperazin-1-yl}-2-azetidin-1-yl-ethyl)-benzonitrile ("129")

[4-(4-Amino-6-{4-[2-azetidin-1-yl-1-(3-cyano-phenyl)-ethyl]-piperazin-1-yl}-pyrimidin-5-yl)-pyrazol-1-yl]-acetic acid methyl ester ("130")

6-{4-[2-Azetidin-1-yl-1-(3,4-dichloro-phenyl)-ethyl]-piperazin-1-yl}-5-(1H-pyrazol-4-yl)-pyrimidin-4-ylamine ("131")

6-{4-[2-Azetidin-1-yl-1-(4-chloro-3-trifluoromethyl-phenyl)-ethyl]-piperazin-1-yl}-5-(1H-pyrazol-4-yl)-pyrimidin-4-ylamine ("132")

6-{4-[2-Azetidin-1-yl-1-(3,4-dichloro-phenyl)-ethyl]-piperazin-1-yl}-5-(6-piperazin-1-yl-pyridin-3-yl)-pyrimidin-4-ylamine ("133")

6-{4-[2-Azetidin-1-yl-1-(2-chloro-3-trifluoromethyl-phenyl)-ethyl]-piperazin-1-yl}-5-(1H-pyrazol-4-yl)-pyrimidin-4-ylamine ("134")

6-{4-[2-Azetidin-1-yl-1-(3-chloro-4-fluoro-phenyl)-ethyl]-piperazin-1-yl}-5-(1H-pyrazol-4-yl)-pyrimidin-4-ylamine ("135")

6-{4-[2-Azetidin-1-yl-1-(2-chloro-4-fluoro-phenyl)-ethyl]-piperazin-1-yl}-5-(1H-pyrazol-4-yl)-pyrimidin-4-ylamine ("137")

1-6-amino-5-(4-fluoropheny)pyrimidin-4-yl)piperidin-4-yl-4-(chlorophenyl)methanol ("138")

1-6-amino-5-(4-fluoropheny)pyrimidin-4-yl)piperidin-4-yl-4-(4-fluorophenyl)phenyl)methanol ("139")

1-6-amino-5-(4-fluoropheny)pyrimidin-4-yl)piperidin-4-yl-4-(fluorophenyl)methanol ("140")

1-6-amino-5-(vinylpyrimidin-4-yl)piperidin-4-yl-4-(fluorophenyl)methanol ("141")

5-(4-Fluorophenyl)-6{4-amino(4-chlorophenyl)methyl-piperidin-1-yl}pyrimidin-4-amine ("142")

5-(4-Fluorophenyl)-6{4-amino(4-fluorophenyl)methyl-piperidin-1-yl}pyrimidin-4-amine ("143")

5-(4-Fluorophenyl)-6{4-amino(4-(4-fluorophenyl)phenyl)methyl-piperidin-1-yl}pyrimidin-4-amine ("144")

6-(4-((cyclopentylamino)(4-fluorophenyl)methyl)piperidin-1-yl)-5-(4-fluorophenyl)pyrimidin-4-amine ("145")

5-(4-fluoropheny)6-(4-((4-fluorophenyl)(2-(pyrrolidin-1-yl)ethoxy)methyl)-piperidin-1-yl)pyrimidin-4-amine ("146")

5-(4-fluoropheny)6-(4-((4-fluorophenyl)(2-(dimethylamino) ethoxy)methyl)piperidin-1-yl)pyrimidin-4-amine ("147")

5-(4-fluoropheny)-6-(4-((4-fluorophenyl)(pyrrolidin-1-yl)methyl)piperidin-1-yl)pyrimidin-4-amine ("148")

5-(4-fluoropheny)-6-(4-((4-fluorophenyl)(3-difluoropyrrolidin-1-yl)methyl)piperidin-1-yl)pyrimidin-4-amine ("149")

1-(6-amino-5-(4-fluoropheny)pyrimidin-4-yl)(4-((4-fluorophenyl))methyl)-dimethylethane-1,2-diamine ("150")

5-(4-fluorophenyl)-(6-(4-fluoropheny)piperidin-4-ylmethyl)amino) methyl)piperidin-1-yl)pyrimidin-4-amine ("151")

{4-[6-Amino-5-(4-fluoro-phenyl)-pyrimidin-4-yl]-piperazin-1-yl}-(3-trifluoromethyl-phenyl)-acetonitrile ("152")

6-{4-[2-Amino-1-(3-trifluoromethyl-phenyl)-ethyl]-piperazin-1-yl}-5-(4-fluoro-phenyl)-pyrimidin-4-ylamine ("153")

{4-[6-Amino-5-(4-fluoro-phenyl)-pyrimidin-4-yl]-piperazin-1-yl}-(4-fluoro-3-trifluoromethyl-phenyl)-acetonitrile ("154")

6-{4-[2-Amino-1-(4-fluoro-3-trifluoromethyl-phenyl)-ethyl]-piperazin-1-yl}-5-(4-fluoro-phenyl)-pyrimidin-4-ylamine ("155")

{4-[6-Amino-5-(4-fluoro-phenyl)-pyrimidin-4-yl]-piperazin-1-yl}-(3,4-dichloro-phenyl)-acetonitrile ("156")

6-{4-[2-Amino-1-(3,4-dichloro-phenyl)-ethyl]-piperazin-1-yl}-5-(4-fluoro-phenyl)-pyrimidin-4-ylamine ("157")
{4-[6-Amino-5-(4-fluoro-phenyl)-pyrimidin-4-yl]-piperazin-1-yl}-(4-fluoro-phenyl)-acetonitrile ("158")
6-{4-[2-Amino-1-(4-fluoro-phenyl)-ethyl]-piperazin-1-yl}-5-(4-fluoro-phenyl)-pyrimidin-4-ylamine ("159")
{4-[6-Amino-5-(4-fluoro-phenyl)-pyrimidin-4-yl]-piperazin-1-yl}-(3-chloro-4-fluoro-phenyl)-acetonitrile ("160")
6-{4-[2-Amino-1-(3-chloro-4-fluoro-phenyl)-ethyl]-piperazin-1-yl}-5-(4-fluoro-phenyl)-pyrimidin-4-ylamine ("161")
{4-[6-Amino-5-(4-fluoro-phenyl)-pyrimidin-4-yl]-piperazin-1-yl}-(4-chloro-phenyl)-acetonitrile ("162")
6-{4-[2-Amino-1-(4-chloro-phenyl)-ethyl]-piperazin-1-yl}-5-(4-fluoro-phenyl)-pyrimidin-4-ylamine ("163")
{4-[6-Amino-5-(4-fluoro-phenyl)-pyrimidin-4-yl]-piperazin-1-yl}-(4-chloro-3-fluoro-phenyl)-acetonitrile ("164")
[4-(6-Amino-5-bromo-pyrimidin-4-yl)-piperazin-1-yl]-(3-trifluoromethyl-phenyl)-acetonitrile ("166")
[4-(6-Amino-5-bromo-pyrimidin-4-yl)-piperazin-1-yl]-(4-trifluoromethyl-phenyl)-acetonitrile ("167")
{4-[6-Amino-5-(4-fluoro-phenyl)-pyrimidin-4-yl]-piperazin-1-yl}-(4-trifluoromethyl-phenyl)-acetonitrile ("168")
6-{4-[2-Amino-1-(2-fluoro-4-trifluoromethyl-phenyl)-ethyl]-piperazin-1-yl}-5-(4-fluoro-phenyl)-pyrimidin-4-ylamine ("170")
6-[4-((1R,2R)-1-Aminomethyl-2-phenyl-propyl)-piperazin-1-yl]-5-(4-fluoro-phenyl)-pyrimidin-4-ylamine ("171")
6-[4-((1R,2S)-1-Aminomethyl-2-phenyl-propyl)-piperazin-1-yl]-5-(4-fluoro-phenyl)-pyrimidin-4-ylamine ("172")
{4-[6-Amino-5-(4-fluoro-phenyl)-pyrimidin-4-yl]-piperazin-1-yl}-(6-chloro-pyridin-3-yl)-acetonitrile ("173")
6-{4-[2-Amino-1-(6-chloro-pyridin-3-yl)-ethyl]-piperazin-1-yl}-5-(4-fluoro-phenyl)-pyrimidin-4-ylamine ("174")
6-{4-[(S)-2-Amino-1-(6-chloro-pyridin-3-yl)-ethyl]-piperazin-1-yl}-5-(4-fluoro-phenyl)-pyrimidin-4-ylamine ("176")
6-{4-[2-Amino-1-(6-chloro-pyridin-3-yl)-ethyl]-piperazin-1-yl}-5-ethyl-pyrimidin-4-ylamine ("177")
6-{4-[2-Amino-1-(4-chloro-phenyl)-ethyl]-piperazin-1-yl}-5-ethyl-pyrimidin-4-ylamine ("178")
6-{4-[(R)-2-Amino-1-(4-chloro-phenyl)-ethyl]-piperazin-1-yl}-5-ethyl-pyrimidin-4-ylamine ("180")
6-{4-[2-Amino-1-(2,3-dihydro-benzo[1,4]dioxin-6-yl)-ethyl]-piperazin-1-yl}-5-ethyl-pyrimidin-4-ylamine ("181")
2-(4-(6-amino-5-(4-fluorophenyl)pyrimidin-4-yl)piperazin-1-yl)-2-(6-methoxypyridin-3-yl)acetonitrile ("182")
6-(4-(2-amino-1-(6-methoxypyridin-3-yl)ethyl) piperazin-1-yl)-5-(4-fluorophenyl)pyrimidin-4-amine ("183")
2-(4-(6-amino-5-(1H-pyrazol-4-yl)pyrimidin-4-yl)piperazin-1-yl)-2-(4-(methylsulfonyl)phenyl)acetonitrile ("184")
6-(4-(2-amino-1-(4-(methylsulfonyl)phenyl)ethyl)piperazin-1-yl)-5-(1H-pyrazol-4-yl)pyrimidin-4-amine ("185")
6-(4-(2-amino-1-(4-chloro-3-fluorophenyl)ethyl)piperazin-1-yl)-5-(1H-pyrazol-4-yl)pyrimidin-4-amine ("187")
6-[4-(2-Amino-1-cyclohexyl-ethyl)-piperazin-1-yl]-5-ethyl-pyrimidin-4-ylamine ("188")
{4-[6-Amino-5-(4-fluoro-phenyl)-pyrimidin-4-yl]-piperazin-1-yl}-pyridin-3-yl-acetonitrile ("190")
{4-[6-Amino-5-(4-fluoro-phenyl)-pyrimidin-4-yl]-piperazin-1-yl}-cyclohexyl-acetonitrile ("191")
6-{4-[2-Amino-1-(2-fluoro-5-trifluoromethyl-phenyl)-ethyl]-piperazin-1-yl}-5-(4-fluoro-phenyl)-pyrimidin-4-ylamine ("192")
6-[4-(2-Amino-1-pyridin-3-yl-ethyl)-piperazin-1-yl]-5-(4-fluoro-phenyl)-pyrimidin-4-ylamine ("193")
N-[3-Amino-1-(6-amino-5-bromo-pyrimidin-4-yl)-pyrrolidin-3-ylmethyl]-2,4-difluoro-benzamide ("195")
N-[3-Amino-1-(6-amino-5-cyano-pyrimidin-4-yl)-pyrrolidin-3-ylmethyl]-2,4-difluoro-benzamide ("196")
4-Amino-6-{3-amino-3-[(2,4-difluoro-benzoylamino)-methyl]-pyrrolidin-1-yl}-pyrimidine-5-carboxamide ("197")
N-{3-Amino-1-[6-amino-5-(4-cyano-phenyl)-pyrimidin-4-yl]-pyrrolidin-3-ylmethyl}-2,4-difluoro-benzamide ("199")
N-{3-Amino-1-[6-amino-5-(4-phenoxy-phenyl)-pyrimidin-4-yl]-pyrrolidin-3-ylmethyl}-2,4-difluoro-benzamide ("200")
N-{3-Amino-1-[6-amino-5-(6-methoxy-pyridin-3-yl)-pyrimidin-4-yl]-pyrrolidin-3-ylmethyl}-2,4-difluoro-benzamide ("201")
N-{3-Amino-1-[6-amino-5-(4-trifluoromethyl-phenyl)-pyrimidin-4-yl]-pyrrolidin-3-ylmethyl}-2,4-difluoro-benzamide ("202")
N-[3-Amino-1-(6-amino-5-phenyl-pyrimidin-4-yl)-pyrrolidin-3-ylmethyl]-2,4-difluoro-benzamide ("203")
N-{3-Amino-1-[6-amino-5-(3-fluoro-phenyl)-pyrimidin-4-yl]-pyrrolidin-3-ylmethyl}-2,4-difluoro-benzamide ("204")
N-[3-Amino-1-(6-amino-5-pyridin-4-yl-pyrimidin-4-yl)-pyrrolidin-3-ylmethyl]-2,4-difluoro-benzamide ("205")
N-{3-Amino-1-[6-amino-5-(6-piperazin-1-yl-pyridin-3-yl)-pyrimidin-4-yl]-pyrrolidin-3-ylmethyl}-2,4-difluoro-benzamide ("206")
N-[4-Amino-1-(6-amino-5-bromo-pyrimidin-4-yl)-piperidin-4-ylmethyl]-2,4-difluoro-benzamide ("207")
N-{4-Amino-1-[6-amino-5-(4-fluoro-phenyl)-pyrimidin-4-yl]-piperidin-4-ylmethyl}-2,4-difluoro-benzamide ("208")
4-Amino-1-(6-amino-5-ethyl-pyrimidin-4-yl)-piperidine-4-carboxylic acid [(S)-1-(4-chloro-phenyl)-3-hydroxy-propyl]-amide ("214")
4-Amino-1-(6-amino-5-chloro-pyrimidin-4-yl)-piperidine-4-carboxylic acid [(S)-1-(4-chloro-phenyl)-propyl]-amide ("215")
4-Amino-1-(6-amino-5-chloro-pyrimidin-4-yl)-piperidine-4-carboxylic acid [(R)-1-(4-chloro-phenyl)-2,2,2-trifluoroethyl]-amide ("216")
4-Amino-1-(6-amino-5-chloro-pyrimidin-4-yl)-piperidine-4-carboxylic acid [(S)-2-carbamoyl-1-(4-chlorophenyl)ethyl]-amide ("217")
4-Amino-1-(6-amino-5-cyano-pyrimidin-4-yl)-piperidine-4-carboxylic acid [(S)-1-(4-chloro-phenyl)-ethyl]-amide ("218")
4-Amino-1-(6-amino-5-cyano-pyrimidin-4-yl)-piperidine-4-carboxylic acid [(S)-1-(4-chloro-phenyl)-propyl]-amide ("219")

4-Amino-1-(6-amino-5-cyano-pyrimidin-4-yl)-piperidine-4-carboxylic acid [(R)-1-(4-chloro-phenyl)-2,2,2-trifluoroethyl]-amide ("220")
4-Amino-1-(6-amino-5-cyano-pyrimidin-4-yl)-piperidine-4-carboxylic acid [(S)-2-carbamoyl-1-(4-chloro-phenyl)-ethyl]-amide ("221")
4-Amino-1-(6-amino-5-chloro-pyrimidin-4-yl)-piperidine-4-carboxylic acid [(S)-1-(4-chloro-phenyl)-ethyl]-amide ("222")
4-Amino-1-(6-amino-5-chloro-pyrimidin-4-yl)-piperidine-4-carboxylic acid [(S)-3-hydroxy-1-(4-trifluoromethyl-phenyl)-propyl]-amide ("223")
4-Amino-1-[6-amino-5-(1H-pyrazol-4-yl)-pyrimidin-4-yl]-piperidine-4-carboxylic acid [(S)-1-(4-chloro-phenyl)-ethyl]-amide ("224")
4-Amino-1-(6-amino-5-cyano-pyrimidin-4-yl)-piperidine-4-carboxylic acid ((S)-3-hydroxy-1-phenyl-propyl)-amide ("226")
4-Amino-1-(6-amino-5-cyano-pyrimidin-4-yl)-piperidine-4-carboxylic acid ((S)-3-hydroxy-1-p-tolyl-propyl)-amide ("227")
4-Amino-1-(6-amino-5-chloro-pyrimidin-4-yl)-piperidine-4-carboxylic acid ((S)-3-hydroxy-1-phenyl-propyl)-amide ("228")
4-Amino-1-(6-amino-5-cyano-pyrimidin-4-yl)-piperidine-4-carboxylic acid [(S)-3-hydroxy-1-(4-methoxy-phenyl)-propyl]-amide ("229")
4-Amino-1-(6-amino-5-cyano-pyrimidin-4-yl)-piperidine-4-carboxylic acid [(S)-3-hydroxy-1-(4-trifluoromethyl-phenyl)-propyl]-amide ("230")
4-Amino-1-(6-amino-5-cyano-pyrimidin-4-yl)-piperidine-4-carboxylic acid ((S)-3-hydroxy-1-pyridin-4-yl-propyl)-amide ("231")
4-Amino-6-[4-amino-4-((S)-3-hydroxy-1-p-tolyl-propylcarbamoyl)-piperidin-1-yl]-pyrimidine-5-carboxylic acid amide ("232")
4-Amino-6-{4-amino-4-[(S)-3-hydroxy-1-(4-trifluoromethyl-phenyl)-propylcarbamoyl]-piperidin-1-yl}-pyrimidine-5-carboxylic acid amide ("233")
4-Amino-1-(6-amino-5-chloro-pyrimidin-4-yl)-piperidine-4-carboxylic acid [(R)-1-(4-chloro-phenyl)-2-methoxy-ethyl]-amide ("234")
4-Amino-1-(6-amino-5-chloro-pyrimidin-4-yl)-piperidine-4-carboxylic acid [(S)-1-(4-chloro-phenyl)-3-hydroxy-propyl]-amide ("235")
4-Amino-1-(6-amino-5-chloro-pyrimidin-4-yl)-piperidine-4-carboxylic acid [(S)-1-(4-fluoro-phenyl)-3-hydroxy-propyl]-amide ("236")
4-Amino-1-(6-amino-5-chloro-pyrimidin-4-yl)-piperidine-4-carboxylic acid ((S)-3-hydroxy-1-p-tolyl-propyl)-amide ("237")
4-Amino-1-(6-amino-5-chloro-pyrimidin-4-yl)-piperidine-4-carboxylic acid [(S)-3-hydroxy-1-(4-methoxy-phenyl)-propyl]-amide ("238")
4-Amino-1-(6-amino-5-chloro-pyrimidin-4-yl)-piperidine-4-carboxylic acid ((S)-3-hydroxy-1-pyridin-4-yl-propyl)-amide ("239")
4-Amino-1-[6-amino-5-(1H-pyrazol-4-yl)-pyrimidin-4-yl]-piperidine-4-carboxylic acid [(R)-1-(4-chloro-phenyl)-2-methoxy-ethyl]-amide ("240")
4-Amino-1-(6-amino-5-cyano-pyrimidin-4-yl)-piperidine-4-carboxylic acid [(R)-1-(4-chloro-phenyl)-2-methoxy-ethyl]-amide ("241")
4-Amino-1-(6-amino-5-cyano-pyrimidin-4-yl)-piperidine-4-carboxylic acid [(S)-1-(4-chloro-phenyl)-3-hydroxy-propyl]-amide ("242")
4-Amino-1-(6-amino-5-cyano-pyrimidin-4-yl)-piperidine-4-carboxylic acid [(S)-1-(4-fluoro-phenyl)-3-hydroxy-propyl]-amide ("243")
4-Amino-6-{4-amino-4-[(S)-1-(4-chloro-phenyl)-ethylcarbamoyl]-piperidin-1-yl}-pyrimidine-5-carboxylic acid amide ("244")
4-Amino-6-{4-amino-4-[(S)-1-(4-chloro-phenyl)-propylcarbamoyl]-piperidin-1-yl}-pyrimidine-5-carboxylic acid amide ("245")
4-Amino-6-{4-amino-4-[(R)-1-(4-chloro-phenyl)-2-methoxy-ethylcarbamoyl]-piperidin-1-yl}-pyrimidine-5-carboxylic acid amide ("246")
4-Amino-1-(6-amino-5-chloro-pyrimidin-4-yl)-piperidine-4-carboxylic acid [(R)-1-(4-chloro-phenyl)-2-methoxy-ethyl]-amide ("247")
N-{(R)-3-Amino-1-[6-amino-5-(4-fluoro-phenyl)-pyrimidin-4-yl]-pyrrolidin-3-ylmethyl}-2,4-difluoro-benzamide ("248") and
N-{(S)-3-Amino-1-[6-amino-5-(4-fluoro-phenyl)-pyrimidin-4-yl]-pyrrolidin-3-ylmethyl}-2,4-difluoro-benzamide ("249").

* * * * *